US011441131B2

(12) United States Patent
Chen et al.

(10) Patent No.: US 11,441,131 B2
(45) Date of Patent: Sep. 13, 2022

(54) HEPAROSAN SYNTHASES AND USE THEREOF FOR SACCHARIDE SYNTHESIS

(71) Applicant: The Regents of the University of California, Oakland, CA (US)

(72) Inventors: Xi Chen, Davis, CA (US); Lan Na, Davis, CA (US); Hai Yu, Davis, CA (US); John B. McArthur, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/906,898

(22) Filed: Jun. 19, 2020

(65) Prior Publication Data
US 2021/0040458 A1    Feb. 11, 2021

Related U.S. Application Data

(60) Provisional application No. 62/865,071, filed on Jun. 21, 2019.

(51) Int. Cl.
*C12P 19/04* (2006.01)
*C12N 9/10* (2006.01)

(52) U.S. Cl.
CPC ............ *C12N 9/1051* (2013.01); *C12P 19/04* (2013.01); *C12Y 204/01* (2013.01)

(58) Field of Classification Search
CPC ...................................................... C12N 9/24
See application file for complete search history.

(56) References Cited

U.S. PATENT DOCUMENTS

| 9,290,530 | B2 | 3/2016 | Chen et al. |
| 10,160,986 | B2 | 12/2018 | Chen et al. |
| 2008/0125393 | A1* | 5/2008 | DeAngelis ............ A61K 31/726 514/54 |

FOREIGN PATENT DOCUMENTS

WO    2013/013244 A2    1/2013

OTHER PUBLICATIONS

Chandrasekaran, E. V., et al. "Reversible Sialylation: Synthesis of Cytidine 5'-Monophospho-N-Acetylneuraminic Acid from Cytidine 5'-Monophosphate with alpha2,3-Sialyl O-Glycan-, Glycolipid-, and Macromolecule-Based Donors Yields Diverse Sialylated Products." Biochemistry 2008, 47, 320-330.
Chavaroche, A. A., et al. "Analysis of the Polymerization Initiation and Activity of Pasteurella multocida Heparosan Synthase PmHS2, An Enzyme with Glycosyltransferase and UDP-Sugar Hydrolase activity." J. Biol. Chem. 2011, 286, 1777-1785.
Chavaroche, A. A., et al. "In vitro Synthesis of Heparosan Using Recombinant Pasteurella multocida Heparosan Synthase PmHS2." Appl. Microbiol. Biotechnol. 2010, 85, 1881-1891.
Chavaroche, A. A., et al. "Synthesis of Heparosan Oligosaccharides by Pasteurella multocida PmHS2 Single-Action Tansferases." Appl. Microbiol. Biotechnol. 2012, 95, 1199-1210.
Chen, Y., et al. "One-Pot Three-Enzyme Synthesis of UDP-GlcNAc Derivatives." Chem. Commun. 2011, 47, 10815-10817.
Chen, Y., et al. "Tailored Design and Synthesis of Heparan Sulfate Oligosaccharide Analogues Using Sequential One-Pot Multienzyme Systems." Angew. Chem., Int. Ed.. 2013, 52, 11852-11856.
DeAngelis, P. L., et al. "Identification and Molecular Cloning of a Heparosan Synthase from Pasteurella multocida Type D." J. Biol. Chem. 2002, 277, 7209-7213.
DeAngelis, P. L., et al. "Identification of a Distinct, Cryptic Heparosan Synthase from Pasteurella multocida Types A, D, and F." J. Bacteriology. 2004, 186, 8529-8532.
Gantt, R. W., et al. "Using Simple Donors to Drive the Equilibria of Glycosyltransferase-Catalyzed Reactions." Nat. Chem. Biol. 2011, 7, 685-691.
Gomez, H., et al. "Retaining Glycosyltransferase Mechanism Studied by QM/MM Methods: Lipopolysaccharyl-Alpha-1,4-Galactosyltransferase C Transfers Alpha-galactose via an Oxocarbenium Ion-Like Transition State." J. Am. Chem. Soc. 2012, 134, 4743-4752.
Jamaluddin, H., et al. "Conformational Changes Induced by Binding UDP-2F-Galactose to Alpha-1,3 Galactosyltransferase—Implications for Catalysis." J. Mol. Biol. 2007, 369, 1270-1281.
Kane, T. A., et al. "Functional Characterization of PmHS1, A Pasteurella multocida Heparosan Synthase." J. Biol. Chem. 2006, 281, 33192-33197.
Lairson, L. L., et al. "Intermediate Trapping on a Mutant Retaining Alpha-Galactosyltransferase Identifies an Unexpected Aspartate Residue." J. Biol. Chem. 2004, 279, 28339-28344.
Lau, K., et al. "Highly Efficient Chemoenzymatic Synthesis of beta1-4-Linked Galactosides with Promiscuous Bacterial beta1-4-Galactosyltransferases." Chem. Commun. 2010, 46, 6066-6068.
Li, Y., et al. "Donor Substrate promiscuity of bacterial beta1-3-N-acetylglucosaminyltransferases and acceptor substrate flexibility of beta1-4-galactosyltransferases." Bioorg. Med. Chem. 2016, 24, 1696-1705.
Li, Y., et al. "Donor Substrate Promiscuity of the N-Acetylglucosaminyltransferase Activities of Pasteurella multocida Heparosan Synthase 2 (PmHS2) and Escherichia coli K5 KfiA." Appl. Microbiol. Biotechnol. 2014, 98, 1127-1134.
Li, Y., et al. "Substrate Promiscuity of N-Acetylhexosamine 1-Kinases." Molecules 2011, 16, 6396-6407.
Liu, R., et al. "Chemoenzymatic Design of Heparan Sulfate Oligosaccharides." J. Biol. Chem. 2010, 285, 34240-34249.
McArthur, J. B., et al. "Alpha2-6-Neosialidase: A Sialyltransferase Mutant as a Sialyl Linkage-Specific Sialidase." ACS Chem. Biol. 2018, 13, 1228-1234.

(Continued)

*Primary Examiner* — Tekchand Saidha
(74) *Attorney, Agent, or Firm* — Kilpatrick Townsend & Stockton LLP

(57) ABSTRACT

Heparosan synthase variants having improved expression levels, enhanced thermal stability, and/or reduced reverse glycosylation activity are provided. Methods for making oligosaccharides and polysaccharides, including heparin analogs and heparan sulfate analogs, are also described.

17 Claims, 25 Drawing Sheets

Specification includes a Sequence Listing.

(56) References Cited

OTHER PUBLICATIONS

Mehr, K., et al. "Mechanisms of the Sialidase and Trans-Sialidase Activities of Bacterial Sialyltransferases from Glycosyltransferase Family 80." Glycobiology 2016, 26, 353-359.

Muthana, M. M., et al. "Efficient One-Pot Multienzyme Synthesis of UDP-Sugars Using a Promiscuous UDP-Sugar Pyrophosphorylase from Bifidobacterium longum (BLUSP)." Chem. Commun. 2012, 48, 2728-2730.

Muthana, M. M., et al. "Improved One-Pot Multienzyme (OPME) Systems for Synthesizing UDP-Uronic Acids and Glucuronides." Chem. Commun. 2015, 51, 4595-4598.

Na, L. "Engineering GT for non-modified heparan sulfate oligosaccharide gram-scale synthesis." Conference presentation, Jan. 31, 2019.

Na, L. "Truncation and Engineering of Heparan Sulfate Biosynthetic Enzyme." Conference presentation, Jun. 1, 2019.

Na, L. "Truncation and Engineering of Heparan Sulfate Biosynthetic Enzymes." Conference presentation, Sep. 16, 2018.

Na, L. et al. "Engineering GT for gram-scale synthesis of non-modified heparan sulfate oligosaccharide." Poster presentation, Feb. 1, 2019.

Na, L. et al. "Engineering GT for gram-scale synthesis of non-modified heparan sulfate oligosaccharide." Poster presentation, Feb. 26, 2019.

Osawa, T., et al. "Crystal Structure of Chondroitin Polymerase from *Escherichia coli* K4." Biochem. Biophys. Res. Commun. 2009, 378, 10-14.

Persson, K., et al. "Crystal Structure of the Retaining Galactosyltransferase LgtC from Neisseria meningitidis in Complex with Donor and Acceptor Sugar Analogs." Nat. Struct. Biol. 2001, 8, 166-175.

Sismey-Ragatz, A. E., et al. "Chemoenzymatic Synthesis with Distinct Pasteurella heparosan Synthases: Monodisperse Polymers and Unnatural Structures." J. Biol. Chem. 2007, 282, 28321-28327.

Wu, B., et al. "Facile Chemoenzymatic Synthesis of Biotinylated Heparosan Hexasaccharide." Org. Biomol. Chem. 2015, 13, 5098-5101.

Xu, Y., et al. "Chemoenzymatic Synthesis of Homogeneous Ultralow Molecular Weight Heparins." Science 2011, 334, 498-501.

Yu, H., et al. "A Multifunctional Pasteurella multocida Sialyltransferase: A Powerful Tool for the Synthesis of Sialoside Libraries." J. Am. Chem. Soc. 2005, 127, 17618-17619.

Zhang, C., et al. "Exploiting the Reversibility of Natural Product Glycosyltransferase-Catalyzed Reactions." Science 2006, 313, 1291-1294.

* cited by examiner

MKG<sup>KKEMTQKQM</sup>TKNPPQHEKENELNTF<sup>QNKIDSLKTTLNKDIIS</sup>QQT<sup>LLAKQ</sup>DSKH
<sup>PLSES</sup>*LEN*<sup>ENKLLLKQ</sup>*LQLVLQE*FEKIY<sup>TYNQALEAKLE</sup>KDK<sup>QTTSITDLYNEVAKSD</sup>LG<sup>LVK</sup>
ETNSAN    SEQ ID NO:2

| UDP Conc | di | tri | tetra | penta | hexa | hepta | octa | nona | deca |
|---|---|---|---|---|---|---|---|---|---|
| 10 mM | 10.6 | 1.7 | 16.7 | 4.6 | 38.5 | 3 | 18.8 | 0.7 | 5.5 |
| 5 mM | 2.4 | 0 | 14.6 | 2.4 | 59.8 | 1.2 | 6.2 | 0 | 2 |
| 1 mM | 0 | 0 | 8.8 | 1.6 | 79.3 | 0 | 9.3 | 0 | 0.9 |
| 0 mM | 0 | 0 | 0 | 0 | 100 | 0 | 0 | 0 | 0 |

FIG. 5

| | GlcAβFmoc | | | Pentasaccharide βFmoc | | |
|---|---|---|---|---|---|---|
| | $k_{cat}$ (s$^{-1}$) | $K_M$ (mM) | $k_{cat}/K_M$ (s$^{-1}$ mM$^{-1}$) | $k_{cat}$ (s$^{-1}$) | $K_M$ (mM) | $k_{cat}/K_M$ (s$^{-1}$ mM$^{-1}$) |
| WT | 2.09 | 12.0 ± 5.5 | 0.17 | 2.20 | 0.11 ± 0.04 | 20 |
| Δ80 | 1.38 | 3.7 ± 1.1 | 0.34 | 1.20 | (2.0 ± 0.5) ×10$^{-2}$ | 60 |

FIG. 11

```
         10         20         30         40         50         60         70         80         90        100
MKGKKEATKQKTKPPQHEKENELNTFQNKIDSLKTTLNDISQQTLLAKVDSKHFSESLENENKLLLKQLVLQEFEKIYYKALEAKLEKDKQ
        110        120        130        140        150        160        170        180        190        200
TTSIDLYHEVAKSDLGLVKETNSANPLVSIIMTSHMTAQFIEASINSLLQTYKNIEIIVDDDSLDNFEIASRANTTSKVRVFRLASNLGTYFAAKN
        210        220        230        240        250        260        270        280        290        300
TGILKSKGDIFFQQSDDVCHERLECWHILLANKETIAVRCAYSRLAPETQHIIKVNMMQYRLGFITLGNHRKVEIGFFNCTTKGSDQEFHRIAK
        310        320        330        340        350        360        370        380        390        400
YYGKEKIKNLLPLYVNTHRENSLFTQMVELDHHIIQKMSDTRQNYATLEQANHETASHDFNHLFQFPRTYDALPVPOEHSKLSMPKIPVYINECSI
        410        420        430        440        450        460        470        480        490        500
PSRIAQLQRTIGILKMQDHFHIYLDGYVEIPDFIKNLGNKATVVHCKQKDNSIRDNGKFILLEELIENQDGYYITCDDITYPSDYTNTHIKLNEYD
        510        520        530        540        550        560        570        580        590        600
DKAVIGLHGILFPSRMTKYFSADRLVSFYKPLEKDNAVIVNLGTGTVSFRVSLFNQFSLSDFTHSGSADIYFSLLCKNNILQICISRPANMLTEDNRDS
        610        620        630        640        650
ETLYHQVRDNEERTQLINENGPNGYSIYPLVKNHPKFTDLPCLPFYFL
```

SEQ ID NO:4

FIG. 12

```
   1 ATGGGCAGCAGCCATCATCATCATCATCACAGCAGCGGCCTGGTGCCGCGCGGCAGCCATATGAAGGGAAAAAA
   1  M  G  S  S  H  H  H  H  H  H  S  S  G  L  V  P  R  G  S  H  M  K  G  K  K
  76 GAGATGACTCAAAAACAAATGACTAAAAATCCACCCCAACATGAAAAAGAAAATGAACTCAACACCTTTCAAAAT
  26  E  M  T  Q  K  Q  M  T  K  N  P  P  Q  H  E  K  E  N  E  L  N  T  F  Q  N
 151 AAAATTGATAGTCTAAAAACAACTTTAAACAAAGACATTATTTCTCAACAAACTTTATTGGCAAAACAGGACAGT
  51  K  I  D  S  L  K  T  T  L  N  K  D  I  I  S  Q  Q  T  L  L  A  K  Q  D  S
 226 AAACATCCGCTATCCGAATCCCTTGAAAACGAAAATAAACTTTTATTAAAACAACTCCAATTGGTTCTACAAGAA
  76  K  H  P  L  S  E  S  L  E  N  E  N  K  L  L  L  K  Q  L  Q  L  V  L  Q  E
 301 TTTGAAAAATATATACCTATAATCAAGCATTAGAAGCAAAGCTAGAAAAAGATAAGCAAACAACATCAATAACA
 101  F  E  K  I  Y  T  Y  N  Q  A  L  E  A  K  L  E  K  D  K  Q  T  T  S  I  T
 376 GATTTATATAATGAAGTCGCTAAAAGTGATTTAGGGTTAGTCAAAGAAACCAACAGCGCAAATCCATTAGTCAGT
 126  D  L  Y  N  E  V  A  K  S  D  L  G  L  V  K  E  T  N  S  A  N  P  L  V  S
 451 ATTATCATGACATCTCACAATACAGCGCAATTTATCGAAGCTTCTATTAATTCATTATTGTTACAAACATATAAA
 151  I  I  M  T  S  H  N  T  A  Q  F  I  E  A  S  I  N  S  L  L  Q  T  Y  K
 526 AACATAGAAATTATTATTGTAGATGATGATAGCTCGGATAATACATTTGAAATTGCCTCGAGAATAGCGAATACA
 176  N  I  E  I  I  I  V  D  D  D  S  S  D  N  T  F  E  I  A  S  R  I  A  N  T
 601 ACAAGCAAAGTCAGAGTATTTAGATTAAATTCAAACCTAGGAACTTACTTTGCGAAAAATACAGGCATATTAAAA
 201  T  S  K  V  R  V  F  R  L  N  S  N  L  G  T  Y  F  A  K  N  T  G  I  L  K
 676 TCTAAAGGTGACATTATTTTCTTTCAAGATAGTGATGATGTATGTCATCATGAAAGAATAGAAAGATGTGTAAAT
 226  S  K  G  D  I  I  F  F  Q  D  S  D  D  V  C  H  H  E  R  I  E  R  C  V  N
 751 ATATTATTAGCTAATAAAGAAACTATTGCTGTTCGTTGTGCATACTCAAGACTAGCACCAGAAACACAACATATC
 251  I  L  L  A  N  K  E  T  I  A  V  R  C  A  Y  S  R  L  A  P  E  T  Q  H  I
 826 ATTAAAGTCAATAATATGGATTATAGATTAGGTTTTATAACCTTGGGTATGCACAGAAAAGTATTTCAAGAAATT
 276  I  K  V  N  N  M  D  Y  R  L  G  F  I  T  L  G  M  H  R  K  V  F  Q  E  I
 901 GGTTTCTTCAATTGTACGACTAAAGGCTCAGATGATGAGTTTTTTCATAGAATTGCGAAATATTATGGAAAAGAA
 301  G  F  F  N  C  T  T  K  G  S  D  D  E  F  F  H  R  I  A  K  Y  Y  G  K  E
 976 AAAATAAAAAATTTACTCTTGCCGTTATACTACAACACAATGAGAGAAAACTCTTTATTTACTGATATGGTTGAA
 326  K  I  K  N  L  L  L  P  L  Y  Y  N  T  M  R  E  N  S  L  F  T  D  M  V  E
1051 TGGATAGACAATCATAACATAATACAGAAAATGTCTGATACCAGACAACATTATGCAACCCTGTTTCAAGCGATG
 351  W  I  D  N  H  N  I  I  Q  K  M  S  D  T  R  Q  H  Y  A  T  L  F  Q  A  M
1126 CATAACGAAACAGCCTCACATGATTTCAAAAATCTTTTTCAATTCCCTCGTATTTACGATGCCTTACCAGTACCA
 376  H  N  E  T  A  S  H  D  F  K  N  L  F  Q  F  P  R  I  Y  D  A  L  P  V  P
1201 CAAGAAATGAGTAAGTTGTCCAATCCTAAGATTCCTGTTTATATCAATATTTGTTCTATTCCCTCAAGAATAGCG
 401  Q  E  M  S  K  L  S  N  P  K  I  P  V  Y  I  N  I  C  S  I  P  S  R  I  A
1276 CAATTACAACGTATTATCGGCATACTAAAAAATCAATGTGATCATTTTCATATTTATCTTGATGGCTATGTAGAA
 426  Q  L  Q  R  I  I  G  I  L  K  N  Q  C  D  H  F  H  I  Y  L  D  G  Y  V  E
1351 ATCCCTGACTTCATAAAAAATTTAGGTAATAAAGCAACCGTTGTTCATTGCAAAGATAAAGATAACTCCATTAGA
 451  I  P  D  F  I  K  N  L  G  N  K  A  T  V  V  H  C  K  D  K  D  N  S  I  R
1426 GATAATGGCAAATTCATTTTACTGGAAGAGTTGATTGAAAAAAATCAAGATGGATATTATATAACCTGTGATGAT
 476  D  N  G  K  F  I  L  L  E  E  L  I  E  K  N  Q  D  G  Y  Y  I  T  C  D  D
1501 GACATTATCTATCCAAGCGATTACATCAATACGATGATCAAAAAGCTGAATGAATACGATGATAAAGCGGTTATT
 501  D  I  I  Y  P  S  D  Y  I  N  T  M  I  K  K  L  N  E  Y  D  D  K  A  V  I
1576 GGTTTACACGGCATTCTCTTTCCAAGTAGAATGACCAAATATTTTCGGCGGATAGACTGGTATATAGCTTCTAT
 526  G  L  H  G  I  L  F  P  S  R  M  T  K  Y  F  S  A  D  R  L  V  Y  S  F  Y
1651 AAACCTCTGGAAAAAGACAAAGCGGTCAATGTATTAGGTACAGGAACTGTTAGCTTTAGAGTCAGTCTCTTTAAT
 551  K  P  L  E  K  D  K  A  V  N  V  L  G  T  G  T  V  S  F  R  V  S  L  F  N
1726 CAATTTTCTCTTTCTGACTTTACCCATTCAGGCATGGCTGATATCTATTTCTCTCTTGTGTAAGAAAAATAAT
 576  Q  F  S  L  S  D  F  T  H  S  G  M  A  D  I  Y  F  S  L  L  C  K  K  N
1801 ATTCTTCAGATTTGTATTTCAAGACCAGCAAACTGGCTAACGGAAGATAATAGAGACAGCGAAACACTCTATCAT
 601  I  L  Q  I  C  I  S  R  P  A  N  W  L  T  E  D  N  R  D  S  E  T  L  Y  H
1876 CAATATCGAGACAATGATGAGCAACAAACTCAGCTGATCATGGAAAACGGTCCATGGGGATATTCAAGTATTTAT
 626  Q  Y  R  D  N  D  E  Q  Q  T  Q  L  I  M  E  N  G  P  W  G  Y  S  S  I  Y
1951 CCATTAGTCAAAAATCATCCTAAATTTACTGACCTTATCCCCTGTTTACCTTTTTATTTTTTATAA          (SEQ ID NO:5)
 651  P  L  V  K  N  H  P  K  F  T  D  L  I  P  C  L  P  F  Y  F  L  *          (SEQ ID NO:6)
```

FIG. 13

```
   1 ATGGGTAGCAGCCATCATCATCATCATCACAGCTTTGAAAAAATATATACCTATAATCAAGCATTAGAAGCAAAG
   1  M  G  S  S  H  H  H  H  H  H  S  F  E  K  I  Y  T  Y  N  Q  A  L  E  A  K
  76 CTAGAAAAAGATAAGCAAACAACATCAATAACAGATTTATATAATGAAGTCGCTAAAAGTGATTTAGGGTTAGTC
  26  L  E  K  D  K  Q  T  T  S  I  T  D  L  Y  N  E  V  A  K  S  D  L  G  L  V
 151 AAAGAAACCAACAGCGCAAATCCATTAGTCAGTATTATCATGACATCTCACAATACAGCGCAATTTATCGAAGCT
  51  K  E  T  N  S  A  N  P  L  V  S  I  I  M  T  S  H  N  T  A  Q  F  I  E  A
 226 TCTATTAATTCATTATTGTTACAAACATATAAAAACATAGAAATTATTATTGTAGATGATGATAGCTCGGATAAT
  76  S  I  N  S  L  L  Q  T  Y  K  N  I  E  I  I  V  D  D  D  S  S  D  N
 301 ACATTTGAAATTGCCTCGAGAATAGCGAATACAACAAGCAAAGTCAGAGTATTTAGATTAAAATTCAAACCTAGGA
 101  T  F  E  I  A  S  R  I  A  N  T  T  S  K  V  R  V  F  R  L  N  S  N  L  G
 376 ACTTACTTTGCGAAAAATACAGGCATATTAAAATCAAAGGTGACATTATTTTCTTTCAAGATAGTGATGATGTA
 126  T  Y  F  A  K  N  T  G  I  L  K  S  K  G  D  I  I  F  F  Q  D  S  D  D  V
 451 TGTCATCATGAAAGAATAGAAAGATGTGTAAATATATTATTAGCTAATAAAGAAACTATTGCTGTTCGTTGTGCA
 151  C  H  H  E  R  I  E  R  C  V  N  I  L  L  A  N  K  E  T  I  A  V  R  C  A
 526 TACTCAAGACTAGCACCAGAAACACAACATATCATTAAAGTCAATAATATGGATTATAGATTAGGTTTTATAACC
 176  Y  S  R  L  A  P  E  T  Q  H  I  I  K  V  N  N  M  D  Y  R  L  G  F  I  T
 601 TTGGGTATGCACAGAAAAGTATTTCAAGAAATTGGTTTCTTCAATTGTACGACTAAAGGCTCAGATGATGAGTTT
 201  L  G  M  H  R  K  V  F  Q  E  I  G  F  F  N  C  T  T  K  G  S  D  D  E  F
 676 TTTCATAGAATTGCGAAATATTATGGAAAAGAAAAAATAAAAAATTTACTCTTGCCGTTATACTACAACACAATG
 226  F  H  R  I  A  K  Y  Y  G  K  E  K  I  K  N  L  L  L  P  L  Y  Y  N  T  M
 751 AGAGAAAACTCTTTATTTACTGATATGGTTGAATGGATAGACAATCATAACATAATACAGAAAATGTCTGATACC
 251  R  E  N  S  L  F  T  D  M  V  E  W  I  D  N  H  N  I  I  Q  K  M  S  D  T
 826 AGACAACATTATGCAACCCTGTTTCAAGCGATGCATAACGAAACAGCCTCACATGATTTCAAAAATCTTTTTCAA
 276  R  Q  H  Y  A  T  L  F  Q  A  M  H  N  E  T  A  S  H  D  F  K  N  L  F  Q
 901 TTCCCTCGTATTTACGATGCCTTACCAGTACCACAAGAAATGAGTAAGTTGTCCAATCCTAAGATTCCTGTTTAT
 301  F  P  R  I  Y  D  A  L  P  V  P  Q  E  M  S  K  L  S  N  P  K  I  P  V  Y
 976 ATCAATATTTGTTCTATTCCCTCAAGAATAGCGCAATTACAACGTATTATCGGCATACTAAAAAATCAATGTGAT
 326  I  N  I  C  S  I  P  S  R  I  A  Q  L  Q  R  I  I  G  I  L  K  N  Q  C  D
1051 CATTTTCATATTTATCTTGATGGCTATGTAGAAATCCCTGACTTCATAAAAAATTTAGGTAATAAAGCAACCGTT
 351  H  F  H  I  Y  L  D  G  Y  V  E  I  P  D  F  I  K  N  L  G  N  K  A  T  V
1126 GTTCATTGCAAAGATAAAGATAACTCCATTAGAGATAATGGCAAATTCATTTTACTGGAAGAGTTGATTGAAAAA
 376  V  H  C  K  D  K  D  N  S  I  R  D  N  G  K  F  I  L  L  E  E  L  I  E  K
1201 AATCAAGATGGATATTATATAACCTGTGATGATGACATTATCTATCCAAGCGATTACATCAATACGATGATCAAA
 401  N  Q  D  G  Y  Y  I  T  C  D  D  D  I  I  Y  P  S  D  Y  I  N  T  M  I  K
1276 AAGCTGAATGAATACGATGATAAAGCGGTTATTGGTTTACACGGCATTCTCTTTCCAAGTAGAATGACCAAATAT
 426  K  L  N  E  Y  D  D  K  A  V  I  G  L  H  G  I  L  F  P  S  R  M  T  K  Y
1351 TTTTCGGCGGATAGACTGGTATATAGCTTCTATAAACCTCTGGAAAAAGACAAAGCGGTCAATGTATTAGGTACA
 451  F  S  A  D  R  L  V  Y  S  F  Y  K  P  L  E  K  D  K  A  V  N  V  L  G  T
1426 GGAACTGTTAGCTTTAGAGTCAGTCTCTTTAATCAATTTTCTCTTTCTGACTTTACCCATTCAGGCATGGCTGAT
 476  G  T  V  S  F  R  V  S  L  F  N  Q  F  S  L  S  D  F  T  H  S  G  M  A  D
1501 ATCTATTTCTCTCTCTTGTGTAAGAAAAATAATATTCTTCAGATTTGTATTTCAAGACCAGCAAACTGGCTAACG
 501  I  Y  F  S  L  L  C  K  K  N  N  I  L  Q  I  C  I  S  R  P  A  N  W  L  T
1576 GAAGATAATAGAGACAGCGAAACACTCTATCATCAATATCGAGACAATGATGAGCAACAAACTCAGCTGATCATG
 526  E  D  N  R  D  S  E  T  L  Y  H  Q  Y  R  D  N  D  E  Q  Q  T  Q  L  I  M
1651 GAAAACGGTCCATGGGGATATTCAAGTATTTATCCATTAGTCAAAAATCATCCTAAATTTACTGACCTTATCCCC
 551  E  N  G  P  W  G  Y  S  S  I  Y  P  L  V  K  N  H  P  K  F  T  D  L  I  P
1726 TGTTTACCTTTTTATTTTTTATAA (SEQ ID NO:7)
 576  C  L  P  F  Y  F  L  *  (SEQ ID NO:3)
```

Δ80PmHS2/Δ80PmHS2_D500N with O6 (20 mM) and UDP (30 mM)

Δ80PmHS2/Δ80PmHS2_D222N with O5 (20 mM) and UDP (30 mM)

SEQUENCE LISTING

<160> NUMBER OF SEQ ID NOS: 14

<210> SEQ ID NO 1
<211> LENGTH: 571
<212> TYPE: PRT
<213> ORGANISM: Pasteurella multocida

<400> SEQUENCE: 1

Phe Glu Lys Ile Tyr Thr Tyr Asn Gln Ala Leu Glu Ala Lys Leu Glu
1               5                   10                  15

Lys Asp Lys Gln Thr Thr Ser Ile Thr Asp Leu Tyr Asn Glu Val Ala
            20                  25                  30

Lys Ser Asp Leu Gly Leu Val Lys Glu Thr Asn Ser Ala Asn Pro Leu

```
                35                  40                  45
Val Ser Ile Ile Met Thr Ser His Asn Thr Ala Gln Phe Ile Glu Ala
 50                  55                  60

Ser Ile Asn Ser Leu Leu Leu Gln Thr Tyr Lys Asn Ile Glu Ile Ile
 65                  70                  75                  80

Ile Val Asp Asp Asp Ser Ser Asp Asn Thr Phe Glu Ile Ala Ser Arg
                 85                  90                  95

Ile Ala Asn Thr Thr Ser Lys Val Arg Val Phe Arg Leu Asn Ser Asn
                100                 105                 110

Leu Gly Thr Tyr Phe Ala Lys Asn Thr Gly Ile Leu Lys Ser Lys Gly
                115                 120                 125

Asp Ile Ile Phe Phe Gln Asp Ser Asp Val Cys His His Glu Arg
                130                 135                 140

Ile Glu Arg Cys Val Asn Ile Leu Leu Ala Asn Lys Glu Thr Ile Ala
145                 150                 155                 160

Val Arg Cys Ala Tyr Ser Arg Leu Ala Pro Glu Thr Gln His Ile Ile
                165                 170                 175

Lys Val Asn Asn Met Asp Tyr Arg Leu Gly Phe Ile Thr Leu Gly Met
                180                 185                 190

His Arg Lys Val Phe Gln Glu Ile Gly Phe Phe Asn Cys Thr Thr Lys
                195                 200                 205

Gly Ser Asp Asp Glu Phe Phe His Arg Ile Ala Lys Tyr Tyr Gly Lys
210                 215                 220

Glu Lys Ile Lys Asn Leu Leu Leu Pro Leu Tyr Tyr Asn Thr Met Arg
225                 230                 235                 240

Glu Asn Ser Leu Phe Thr Asp Met Val Glu Trp Ile Asp Asn His Asn
                245                 250                 255

Ile Ile Gln Lys Met Ser Asp Thr Arg Gln His Tyr Ala Thr Leu Phe
                260                 265                 270

Gln Ala Met His Asn Glu Thr Ala Ser His Asp Phe Lys Asn Leu Phe
                275                 280                 285

Gln Phe Pro Arg Ile Tyr Asp Ala Leu Pro Val Pro Gln Glu Met Ser
                290                 295                 300

Lys Leu Ser Asn Pro Lys Ile Pro Val Tyr Ile Asn Ile Cys Ser Ile
305                 310                 315                 320

Pro Ser Arg Ile Ala Gln Leu Gln Arg Ile Ile Gly Ile Leu Lys Asn
                325                 330                 335

Gln Cys Asp His Phe His Ile Tyr Leu Asp Gly Tyr Val Glu Ile Pro
                340                 345                 350

Asp Phe Ile Lys Asn Leu Gly Asn Lys Ala Thr Val His Cys Lys
                355                 360                 365

Asp Lys Asp Asn Ser Ile Arg Asp Asn Gly Lys Phe Ile Leu Leu Glu
                370                 375                 380

Glu Leu Ile Glu Lys Asn Gln Asp Gly Tyr Tyr Ile Thr Cys Asp Asp
385                 390                 395                 400

Asp Ile Ile Tyr Pro Ser Asp Tyr Ile Asn Thr Met Ile Lys Lys Leu
                405                 410                 415

Asn Glu Tyr Asp Asp Lys Ala Val Ile Gly Leu His Gly Ile Leu Phe
                420                 425                 430

Pro Ser Arg Met Thr Lys Tyr Phe Ser Ala Asp Arg Leu Val Tyr Ser
                435                 440                 445

Phe Tyr Lys Pro Leu Glu Lys Asp Lys Ala Val Asn Val Leu Gly Thr
450                 455                 460
```

Gly Thr Val Ser Phe Arg Val Ser Leu Phe Asn Gln Phe Ser Leu Ser
465                 470                 475                 480

Asp Phe Thr His Ser Gly Met Ala Asp Ile Tyr Phe Ser Leu Leu Cys
                485                 490                 495

Lys Lys Asn Asn Ile Leu Gln Ile Cys Ile Ser Arg Pro Ala Asn Trp
            500                 505                 510

Leu Thr Glu Asp Asn Arg Asp Ser Glu Thr Leu Tyr His Gln Tyr Arg
        515                 520                 525

Asp Asn Asp Glu Gln Gln Thr Gln Leu Ile Met Glu Asn Gly Pro Trp
530                 535                 540

Gly Tyr Ser Ser Ile Tyr Pro Leu Val Lys Asn His Pro Lys Phe Thr
545                 550                 555                 560

Asp Leu Ile Pro Cys Leu Pro Phe Tyr Phe Leu
                565                 570

<210> SEQ ID NO 2
<211> LENGTH: 126
<212> TYPE: PRT
<213> ORGANISM: Pasteurella multocida

<400> SEQUENCE: 2

Met Lys G

```
Leu Leu Gln Thr Tyr Lys Asn Ile Glu Ile Ile Val Asp Asp Asp
            85                  90                  95

Ser Ser Asp Asn Thr Phe Glu Ile Ala Ser Arg Ile Ala Asn Thr Thr
            100                 105                 110

Ser Lys Val Arg Val Phe Arg Leu Asn Ser Asn Leu Gly Thr Tyr Phe
            115                 120                 125

Ala Lys Asn Thr Gly Ile Leu Lys Ser Lys Gly Asp Ile Ile Phe Phe
    130                 135                 140

Gln Asp Ser Asp Asp Val Cys His His Glu Arg Ile Glu Arg Cys Val
145                 150                 155                 160

Asn Ile Leu Leu Ala Asn Lys Glu Thr Ile Ala Val Arg Cys Ala Tyr
                165                 170                 175

Ser Arg Leu Ala Pro Glu Thr Gln His Ile Ile Lys Val Asn Asn Met
            180                 185                 190

Asp Tyr Arg Leu Gly Phe Ile Thr Leu Gly Met His Arg Lys Val Phe
        195                 200                 205

Gln Glu Ile Gly Phe Phe Asn Cys Thr Thr Lys Gly Ser Asp Asp Glu
    210                 215                 220

Phe Phe His Arg Ile Ala Lys Tyr Tyr Gly Lys Glu Lys Ile Lys Asn
225                 230                 235                 240

Leu Leu Leu Pro Leu Tyr Tyr Asn Thr Met Arg Glu Asn Ser Leu Phe
            245                 250                 255

Thr Asp Met Val Glu Trp Ile Asp Asn His Asn Ile Ile Gln Lys Met
            260                 265                 270

Ser Asp Thr Arg Gln His Tyr Ala Thr Leu Phe Gln Ala Met His Asn
        275                 280                 285

Glu Thr Ala Ser His Asp Phe Lys Asn Leu Phe Gln Phe Pro Arg Ile
    290                 295                 300

Tyr Asp Ala Leu Pro Val Pro Gln Glu Met Ser Lys Leu Ser Asn Pro
305                 310                 315                 320

Lys Ile Pro Val Tyr Ile Asn Ile Cys Ser Ile Pro Ser Arg Ile Ala
                325                 330                 335

Gln Leu Gln Arg Ile Ile Gly Ile Leu Lys Asn Gln Cys Asp His Phe
            340                 345                 350

His Ile Tyr Leu Asp Gly Tyr Val Glu Ile Pro Asp Phe Ile Lys Asn
        355                 360                 365

Leu Gly Asn Lys Ala Thr Val Val His Cys Lys Asp Lys Asp Asn Ser
    370                 375                 380

Ile Arg Asp Asn Gly Lys Phe Ile Leu Leu Glu Leu Ile Glu Lys
385                 390                 395                 400

Asn Gln Asp Gly Tyr Tyr Ile Thr Cys Asp Asp Ile Ile Tyr Pro
            405                 410                 415

Ser Asp Tyr Ile Asn Thr Met Ile Lys Lys Leu Asn Glu Tyr Asp Asp
        420                 425                 430

Lys Ala Val Ile Gly Leu His Gly Ile Leu Phe Pro Ser Arg Met Thr
    435                 440                 445

Lys Tyr Phe Ser Ala Asp Arg Leu Val Tyr Ser Phe Tyr Lys Pro Leu
    450                 455                 460

Glu Lys Asp Lys Ala Val Asn Val Leu Gly Thr Gly Thr Val Ser Phe
465                 470                 475                 480

Arg Val Ser Leu Phe Asn Gln Phe Ser Leu Ser Asp Phe Thr His Ser
            485                 490                 495
```

Gly Met Ala Asp Ile Tyr Phe Ser Leu Leu Cys Lys Lys Asn Asn Ile
                500                 505                 510

Leu Gln Ile Cys Ile Ser Arg Pro Ala Asn Trp Leu Thr Glu Asp Asn
            515                 520                 525

Arg Asp Ser Glu Thr Leu Tyr His Gln Tyr Arg Asp Asn Asp Glu Gln
        530                 535                 540

Gln Thr Gln Leu Ile Met Glu Asn Gly Pro Trp Gly Tyr Ser Ser Ile
545                 550                 555                 560

Tyr Pro Leu Val Lys Asn His Pro Lys Phe Thr Asp Leu Ile Pro Cys
                565                 570                 575

Leu Pro Phe Tyr Phe Leu
            580

<210> SEQ ID NO 4
<211> LENGTH: 651
<212> TYPE: PRT
<213> ORGANISM: Pasteurella multocida

<400> SEQUENCE: 4

Met Lys Gly Lys Lys Glu Met Thr Gln Lys Gln Met Thr Lys Asn Pro
1               5                   10                  15

Pro Gln His Glu Lys Glu Asn Glu Leu Asn Thr Phe Gln Asn Lys Ile
            20                  25                  30

Asp Ser Leu Lys Thr Thr Leu Asn Lys Asp Ile Ile Ser Gln Gln Thr
        35                  40                  45

Leu Leu Ala Lys Gln Asp Ser Lys His Pro Leu Ser Glu Ser Leu Glu
    50                  55                  60

Asn Glu Asn Lys Leu Leu Leu Lys Gln Leu Gln Val Leu Gln Glu
65                  70                  75                  80

Phe Glu Lys Ile Tyr Thr Tyr Asn Gln Ala Leu Glu Ala Lys Leu Glu
                85                  90                  95

Lys Asp Lys Gln Thr Thr Ser Ile Thr Asp Leu Tyr Asn Glu Val Ala
            100                 105                 110

Lys Ser Asp Leu Gly Leu Val Lys Glu Thr Asn Ser Ala Asn Pro Leu
        115                 120                 125

Val Ser Ile Ile Met Thr Ser His Asn Thr Ala Gln Phe Ile Glu Ala
    130                 135                 140

Ser Ile Asn Ser Leu Leu Leu Gln Thr Tyr Lys Asn Ile Glu Ile Ile
145                 150                 155                 160

Ile Val Asp Asp Asp Ser Ser Asp Asn Thr Phe Glu Ile Ala Ser Arg
                165                 170                 175

Ile Ala Asn Thr Thr Ser Lys Val Arg Val Phe Arg Leu Asn Ser Asn
            180                 185                 190

Leu Gly Thr Tyr Phe Ala Lys Asn Thr Gly Ile Leu Lys Ser Lys Gly
        195                 200                 205

Asp Ile Ile Phe Phe Gln Asp Ser Asp Asp Val Cys His His Glu Arg
    210                 215                 220

Ile Glu Arg Cys Val Asn Ile Leu Leu Ala Asn Lys Glu Thr Ile Ala
225                 230                 235                 240

Val Arg Cys Ala Tyr Ser Arg Leu Ala Pro Glu Thr Gln His Ile Ile
                245                 250                 255

Lys Val Asn Asn Met Asp Tyr Arg Leu Gly Phe Ile Thr Leu Gly Met
            260                 265                 270

His Arg Lys Val Phe Gln Glu Ile Gly Phe Phe Asn Cys Thr Thr Lys
        275                 280                 285

Gly Ser Asp Asp Glu Phe Phe His Arg Ile Ala Lys Tyr Tyr Gly Lys
290                 295                 300

Glu Lys Ile Lys Asn Leu Leu Leu Pro Leu Tyr Tyr Asn Thr Met Arg
305                 310                 315                 320

Glu Asn Ser Leu Phe Thr Asp Met Val Glu Trp Ile Asp Asn His Asn
            325                 330                 335

Ile Ile Gln Lys Met Ser Asp Thr Arg Gln His Tyr Ala Thr Leu Phe
            340                 345                 350

Gln Ala Met His Asn Glu Thr Ala Ser His Asp Phe Lys Asn Leu Phe
            355                 360                 365

Gln Phe Pro Arg Ile Tyr Asp Ala Leu Pro Val Pro Gln Glu Met Ser
            370                 375                 380

Lys Leu Ser Asn Pro Lys Ile Pro Val Tyr Ile Asn Ile Cys Ser Ile
385                 390                 395                 400

Pro Ser Arg Ile Ala Gln Leu Gln Arg Ile Ile Gly Ile Leu Lys Asn
            405                 410                 415

Gln Cys Asp His Phe His Ile Tyr Leu Asp Gly Tyr Val Glu Ile Pro
            420                 425                 430

Asp Phe Ile Lys Asn Leu Gly Asn Lys Ala Thr Val Val His Cys Lys
            435                 440                 445

Asp Lys Asp Asn Ser Ile Arg Asp Asn Gly Lys Phe Ile Leu Leu Glu
450                 455                 460

Glu Leu Ile Glu Lys Asn Gln Asp Gly Tyr Tyr Ile Thr Cys Asp Asp
465                 470                 475                 480

Asp Ile Ile Tyr Pro Ser Asp Tyr Ile Asn Thr Met Ile Lys Lys Leu
            485                 490                 495

Asn Glu Tyr Asp Asp Lys Ala Val Ile Gly Leu His Gly Ile Leu Phe
            500                 505                 510

Pro Ser Arg Met Thr Lys Tyr Phe Ser Ala Asp Arg Leu Val Tyr Ser
            515                 520                 525

Phe Tyr Lys Pro Leu Glu Lys Asp Lys Ala Val Asn Val Leu Gly Thr
            530                 535                 540

Gly Thr Val Ser Phe Arg Val Ser Leu Phe Asn Gln Phe Ser Leu Ser
545                 550                 555                 560

Asp Phe Thr His Ser Gly Met Ala Asp Ile Tyr Phe Ser Leu Leu Cys
            565                 570                 575

Lys Lys Asn Asn Ile Leu Gln Ile Cys Ile Ser Arg Pro Ala Asn Trp
            580                 585                 590

Leu Thr Glu Asp Asn Arg Asp Ser Glu Thr Leu Tyr His Gln Tyr Arg
            595                 600                 605

Asp Asn Asp Glu Gln Gln Thr Gln Leu Ile Met Glu Asn Gly Pro Trp
            610                 615                 620

Gly Tyr Ser Ser Ile Tyr Pro Leu Val Lys Asn His Pro Lys Phe Thr
625                 630                 635                 640

Asp Leu Ile Pro Cys Leu Pro Phe Tyr Phe Leu
            645                 650

<210> SEQ ID NO 5
<211> LENGTH: 2016
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
atgggcagca gccatcatca tcatcatcac agcagcggcc tggtgccgcg cggcagccat    60
atgaagggaa aaaagagat gactcaaaaa caaatgacta aaaatccacc ccaacatgaa    120
aagaaaatg aactcaacac cttttcaaaat aaaattgata gtctaaaaac aactttaaac   180
aaagacatta tttctcaaca aactttattg gcaaaacagg acagtaaaca tccgctatcc   240
gaatcccttg aaaacgaaaa taaacttttta ttaaaacaac tccaattggt tctacaagaa   300
tttgaaaaaa tatatacccta taatcaagca ttagaagcaa agctagaaaa agataagcaa   360
acaacatcaa taacagattt atataatgaa gtcgctaaaa gtgatttagg gttagtcaaa   420
gaaaccaaca gcgcaaatcc attagtcagt attatcatga catctcacaa tacagcgcaa   480
tttatcgaag cttctattaa ttcattattg ttacaaacat ataaaaacat agaaattatt   540
attgtagatg atgatagctc ggataataca tttgaaattg cctcgagaat agcgaataca   600
acaagcaaag tcagagtatt tagattaaat tcaaacctag gaacttactt tgcgaaaaat   660
acaggcatat taaaatctaa aggtgacatt attttctttc aagatagtga tgatgtatgt   720
catcatgaaa gaatagaaag atgtgtaaat atattattag ctaataaaga aactattgct   780
gttcgttgtg catactcaag actagcacca gaaacacaac atatcattaa agtcaataat   840
atggattata gattaggttt tataaccttg ggtatgcaca gaaaagtatt tcaagaaatt   900
ggtttcttca attgtacgac taaaggctca gatgatgagt tttttcatag aattgcgaaa   960
tattatggaa aagaaaaaat aaaaaattta ctcttgccgt tatactacaa cacaatgaga   1020
gaaaactctt tatttactga tatggttgaa tggatagaca atcataacat aatacagaaa   1080
atgtctgata ccagacaaca ttatgcaacc ctgtttcaag cgatgcataa cgaaacagcc   1140
tcacatgatt tcaaaaatct tttttcaattc cctcgtattt acgatgcctt accagtacca   1200
caagaaatga gtaagttgtc caatcctaag attcctgttt atatcaatat ttgttctatt   1260
ccctcaagaa tagcgcaatt acaacgtatt atcggcatac taaaaaatca atgtgatcat   1320
tttcatattt atcttgatgg ctatgtagaa atccctgact tcataaaaaa tttaggtaat   1380
aaagcaaccg ttgttcattg caaagataaa gataactcca ttagagataa tggcaaattc   1440
attttactgg aagagttgat tgaaaaaaat caagatggat attatataac ctgtgatgat   1500
gacattatct atccaagcga ttacatcaat acgatgatca aaaagctgaa tgaatacgat   1560
gataaagcgg ttattggttt acacggcatt ctcttttccaa gtagaatgac caaatatttt   1620
tcggcggata gactggtata tagcttctat aaacctctgg aaaaagacaa agcggtcaat   1680
gtattaggta caggaactgt tagctttaga gtcagtctct ttaatcaatt ttctctttct   1740
gactttaccc attcaggcat ggctgatatc tatttctctc tcttgtgtaa gaaaaataat   1800
attcttcaga tttgtatttc aagaccagca aactggctaa cggaagataa tagagacagc   1860
gaaacactct atcatcaata tcgagacaat gatgagcaac aaactcagct gatcatggaa   1920
aacggtccat ggggatattc aagtatttat ccattagtca aaaatcatcc taaatttact   1980
gaccttatcc cctgtttacc ttttttatttt ttataa                             2016
```

<210> SEQ ID NO 6
<211> LENGTH: 671
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 6

Met Gly Ser Ser His His His His His His Ser Ser Gly Leu Val Pro
1               5                   10                  15

Arg Gly Ser His Met Lys Gly Lys Lys Glu Met Thr Gln Lys Gln Met
            20                  25                  30

Thr Lys Asn Pro Pro Gln His Glu Lys Glu Asn Glu Leu Asn Thr Phe
        35                  40                  45

Gln Asn Lys Ile Asp Ser Leu Lys Thr Thr Leu Asn Lys Asp Ile Ile
    50                  55                  60

Ser Gln Gln Thr Leu Leu Ala Lys Gln Asp Ser Lys His Pro Leu Ser
65                  70                  75                  80

Glu Ser Leu Glu Asn Glu Asn Lys Leu Leu Leu Lys Gln Leu Gln Leu
                85                  90                  95

Val Leu Gln Glu Phe Glu Lys Ile Tyr Thr Tyr Asn Gln Ala Leu Glu
            100                 105                 110

Ala Lys Leu Glu Lys Asp Lys Gln Thr Thr Ser Ile Thr Asp Leu Tyr
        115                 120                 125

Asn Glu Val Ala Lys Ser Asp Leu Gly Leu Val Lys Glu Thr Asn Ser
130                 135                 140

Ala Asn Pro Leu Val Ser Ile Ile Met Thr Ser His Asn Thr Ala Gln
145                 150                 155                 160

Phe Ile Glu Ala Ser Ile Asn Ser Leu Leu Leu Gln Thr Tyr Lys Asn
                165                 170                 175

Ile Glu Ile Ile Ile Val Asp Asp Ser Ser Asp Asn Thr Phe Glu
            180                 185                 190

Ile Ala Ser Arg Ile Ala Asn Thr Thr Ser Lys Val Arg Val Phe Arg
        195                 200                 205

Leu Asn Ser Asn Leu Gly Thr Tyr Phe Ala Lys Asn Thr Gly Ile Leu
210                 215                 220

Lys Ser Lys Gly Asp Ile Ile Phe Phe Gln Asp Ser Asp Asp Val Cys
225                 230                 235                 240

His His Glu Arg Ile Glu Arg Cys Val Asn Ile Leu Leu Ala Asn Lys
                245                 250                 255

Glu Thr Ile Ala Val Arg Cys Ala Tyr Ser Arg Leu Ala Pro Glu Thr
            260                 265                 270

Gln His Ile Ile Lys Val Asn Asn Met Asp Tyr Arg Leu Gly Phe Ile
        275                 280                 285

Thr Leu Gly Met His Arg Lys Val Phe Gln Glu Ile Gly Phe Phe Asn
290                 295                 300

Cys Thr Thr Lys Gly Ser Asp Asp Glu Phe Phe His Arg Ile Ala Lys
305                 310                 315                 320

Tyr Tyr Gly Lys Glu Lys Ile Lys Asn Leu Leu Leu Pro Leu Tyr Tyr
                325                 330                 335

Asn Thr Met Arg Glu Asn Ser Leu Phe Thr Asp Met Val Glu Trp Ile
            340                 345                 350

Asp Asn His Asn Ile Ile Gln Lys Met Ser Asp Thr Arg Gln His Tyr
        355                 360                 365

Ala Thr Leu Phe Gln Ala Met His Asn Glu Thr Ala Ser His Asp Phe
370                 375                 380

Lys Asn Leu Phe Gln Phe Pro Arg Ile Tyr Asp Ala Leu Pro Val Pro
385                 390                 395                 400

Gln Glu Met Ser Lys Leu Ser Asn Pro Lys Ile Pro Val Tyr Ile Asn
                405                 410                 415
```

Ile Cys Ser Ile Pro Ser Arg Ile Ala Gln Leu Gln Arg Ile Ile Gly
                420                 425                 430

Ile Leu Lys Asn Gln Cys Asp His Phe His Ile Tyr Leu Asp Gly Tyr
            435                 440                 445

Val Glu Ile Pro Asp Phe Ile Lys Asn Leu Gly Asn Lys Ala Thr Val
        450                 455                 460

Val His Cys Lys Asp Lys Asp Asn Ser Ile Arg Asp Asn Gly Lys Phe
465                 470                 475                 480

Ile Leu Leu Glu Glu Leu Ile Glu Lys Asn Gln Asp Gly Tyr Tyr Ile
                485                 490                 495

Thr Cys Asp Asp Asp Ile Ile Tyr Pro Ser Asp Tyr Ile Asn Thr Met
            500                 505                 510

Ile Lys Lys Leu Asn Glu Tyr Asp Asp Lys Ala Val Ile Gly Leu His
        515                 520                 525

Gly Ile Leu Phe Pro Ser Arg Met Thr Lys Tyr Phe Ser Ala Asp Arg
530                 535                 540

Leu Val Tyr Ser Phe Tyr Lys Pro Leu Glu Lys Asp Lys Ala Val Asn
545                 550                 555                 560

Val Leu Gly Thr Gly Thr Val Ser Phe Arg Val Ser Leu Phe Asn Gln
                565                 570                 575

Phe Ser Leu Ser Asp Phe Thr His Ser Gly Met Ala Asp Ile Tyr Phe
            580                 585                 590

Ser Leu Leu Cys Lys Lys Asn Asn Ile Leu Gln Ile Cys Ile Ser Arg
        595                 600                 605

Pro Ala Asn Trp Leu Thr Glu Asp Asn Arg Asp Ser Glu Thr Leu Tyr
610                 615                 620

His Gln Tyr Arg Asp Asn Asp Glu Gln Gln Thr Gln Leu Ile Met Glu
625                 630                 635                 640

Asn Gly Pro Trp Gly Tyr Ser Ser Ile Tyr Pro Leu Val Lys Asn His
                645                 650                 655

Pro Lys Phe Thr Asp Leu Ile Pro Cys Leu Pro Phe Tyr Phe Leu
            660                 665                 670

<210> SEQ ID NO 7
<211> LENGTH: 1749
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
atgggtagca gccatcatca tcatcatcac agctttgaaa aaatatatac ctataatcaa      60
gcattagaag caaagctaga aaagataag caaacaacat caataacaga tttatataat     120
gaagtcgcta aaagtgattt agggttagtc aaagaaacca acagcgcaaa tccattagtc     180
agtattatca tgacatctca caatacagcg caatttatcg aagcttctat taattcatta     240
ttgttacaaa catataaaaa catagaaatt attattgtag atgatgatag ctcggataat     300
acatttgaaa ttgcctcgag aatagcgaat acaacaagca aagtcagagt atttagatta     360
aattcaaacc taggaactta ctttgcgaaa atacaggca tattaaaatc taaaggtgac     420
attattttct ttcaagatag tgatgatgta tgtcatcatg aaagaataga agatgtgta     480 aatatattat tagctaataa agaaactatt gctgttcgtt gtgcatactc aagactagca     540
ccagaaacac aacatatcat taaagtcaat aatatggatt atagattagg tttataacc     600

```
ttgggtatgc acagaaaagt atttcaagaa attggtttct tcaattgtac gactaaaggc      660
tcagatgatg agttttttca tagaattgcg aaatattatg gaaaagaaaa aataaaaaat      720
ttactcttgc cgttatacta caacacaatg agagaaaact ctttatttac tgatatggtt      780
gaatggatag acaatcataa cataatacag aaaatgtctg ataccagaca acattatgca      840
accctgtttc aagcgatgca taacgaaaca gcctcacatg atttcaaaaa tcttttttcaa     900 ttccctcgta tttacgatgc cttaccagta ccacaagaaa tgagtaagtt gtccaatcct     960
aagattcctg tttatatcaa tatttgttct attccctcaa gaatagcgca attacaacgt     1020
attatcggca tactaaaaaa tcaatgtgat cattttcata tttatcttga tggctatgta     1080
gaaatccctg acttcataaa aaatttaggt aataaagcaa ccgttgttca ttgcaaagat     1140
aaagataact ccattagaga taatggcaaa ttcattttac tggaagagtt gattgaaaaa     1200
aatcaagatg atattatat aacctgtgat gatgacatta tctatccaag cgattacatc     1260
aatacgatga tcaaaaagct gaatgaatac gatgataaag cggttattgg tttacacggc     1320
attctctttc caagtagaat gaccaaatat ttttcggcgg atagactggt atatagcttc     1380
tataaacctc tggaaaaaga caaagcggtc aatgtattag gtacaggaac tgttagcttt     1440
agagtcagtc tctttaatca attttctctt tctgacttta cccattcagg catggctgat     1500
atctatttct ctctcttgtg taagaaaaat aatattcttc agatttgtat ttcaagacca     1560
gcaaactggc taacggaaga taatagagac agcgaaacac tctatcatca atatcgagac     1620
aatgatgagc aacaaactca gctgatcatg gaaaacggtc catggggata ttcaagtatt     1680
tatccattag tcaaaaatca tcctaaattt actgaccta tccctgttt acctttttat     1740 tttttataa                                                             1749
```

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
atcacagctt tgaaaaaata tacctata atcaagcatt agaagc                      46
```

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
gatgatgatg atggctgcta ccc                                             23
```

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

```
taaaggctca aacgatgagt tttttc                                          26
```

```
<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtcgtacaat tgaagaaac                                              19

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tcaggcatgg ctaatatcta tttctctctc ttgtg                            35

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atgggtaaag tcagaaagag aaaattgatt aaagagac                         38

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5
```

HEPAROSAN SYNTHASES AND USE THEREOF FOR SACCHARIDE SYNTHESIS

CROSS-REFERENCES TO RELATED APPLICATIONS

This application claims priority to U.S. Provisional Application No. 62/865,071, filed Jun. 21, 2019, the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant Nos. R01GM094523 and U01GM125288 awarded by the National Institutes of Health. The government has certain rights in the invention.

REFERENCE TO SUBMISSION OF A SEQUENCE LISTING AS A TEXT FILE

The Sequence Listing written in file 076916-231910US-1199136_SL.txt created on Oct. 6, 2020, 29,823 bytes, machine format IBM-PC, MS-Windows operating system, is hereby incorporated by reference in its entirety for all purposes.

BACKGROUND OF THE INVENTION

*Pasteurella multocida* heparosan synthase 2 (PmHS2) is the most commonly used glycosyltransferase/polysaccharide polymerase for producing heparosan, the capsular polysaccharide structure of some *Pasteurella multocida* and the backbone of mammalian heparan sulfate (HS) and heparin. PmHS2 is a bifunctional glycosyltransferase that catalyzes the transfer of both N-acetylglucosamine (GlcNAc) and glucuronic acid (GlcA) from their corresponding sugar nucleotides uridine 5'-diphosphate (UDP)-GlcNAc and UDP-GlcA, respectively.

Heparin is a clinically used anticoagulant and heparan sulfate (HS), a dynamic multifunctional cell regulator, is an important component of extracellular matrix. HS modulates cell migration, adhesion, proliferation, differentiation, and signaling. On cell surfaces, more than 100 proteins are known to bind with HS (e.g., chemokines, cytokines, growth factors, and morphogens). Individual heterogeneous HS structures function as epitopes for different HS binding proteins. Understanding of the relationship between the chemical structure and biological functions of HS is an important goal. However, challenges in synthesizing HS-like oligosaccharides and polysaccharides limits the current understanding of the biological role of HS and therapeutic possibilities. Synthetic challenges include the diverse chemical space of heparan sulfate, low synthetic efficiency which prevents large scale synthesis, and the difficulty of obtaining homogenous, structurally defined HS.

SUMMARY

In one aspect, the disclosure features a truncated heparosan synthase variant.

In another aspect, the disclosure features a *Pasteurella multocida* heparosan synthase 2 (PmHS2) variant comprising a polypeptide having at least 70% identity to the amino acid sequence set forth in SEQ ID NO:1.

In some embodiments, the PmHS2 variant consists of the polypeptide having at least 70% identity to the amino acid sequence set forth in SEQ ID NO:1.

In some embodiments, the PmHS2 variant comprises a mutation at one or more positions corresponding to Y165, R184, L185, F187, I188, T189, D211, N237, K379, L462, T464, T466, V467, S485, G486, M487, and D489 in SEQ ID NO:1.

In another aspect, the disclosure features a *Pasteurella multocida* heparosan synthase 2 (PmHS2) variant comprising a polypeptide having at least 70% identity to the amino acid sequence set forth in SEQ ID NO:3.

In some embodiments, the PmHS2 variant consists of the polypeptide having at least 70% identity to the amino acid sequence set forth in SEQ ID NO:3.

In some embodiments, the PmHS2 variant comprises a mutation at one or more positions corresponding to Y176, R195, L196, F198, I199, T200, D222, N248, K390, L473, T475, T477, V478, S496, G497, M498, and D500 in SEQ ID NO:3.

In some embodiments, the PmHS2 variant comprises one or more mutations corresponding to Y176A, R195A, L196A, F198A, I199A, T200A, D222N, N248A, K390A, L473A, T475A, T477A, V478A, S496N, S496A, G497 deletion, M498A, and D500N in SEQ ID NO:3.

In particular embodiments, the PmHS2 variant comprises the mutation D222N or D500N in SEQ ID NO:3. In particular embodiments, the PmHS2 variant comprises the mutations D410N, D412N, and D500N in SEQ ID NO:3. In particular embodiments, the PmHS2 variant comprises the mutation with deletion of G497 in SEQ ID NO:3. In particular embodiments, the PmHS2 variant comprises the mutations Y176A, R195A, L196A, F198A, I199A, T200A, and/or N248A in SEQ ID NO:3. In particular embodiments, the PmHS2 variant comprises the mutations K390A, L473A, T475A, T477A, and/or V478A in SEQ ID NO:3. In particular embodiments, the PmHS2 variant comprises the mutations S496N, S496A, and/or M498A in SEQ ID NO:3. In particular embodiments, the PmHS2 variant comprises the mutations S496A, M498A, S496 deletion, and/or M498 deletion in SEQ ID NO:3.

In another aspect, the disclosure features a method of preparing an oligosaccharide, the method comprising: forming a mixture comprising (i) a heparosan synthase variant described herein or a PmHS2 variant described herein, (ii) an acceptor sugar, and (iii) a nucleotide sugar comprising a nucleotide moiety and a donor sugar moiety, and maintaining the mixture under conditions sufficient to transfer the donor sugar moiety to the acceptor sugar.

In some embodiments, the nucleotide sugar in the mixture is formed by converting a sugar starting material to the nucleotide sugar.

In some embodiments, the acceptor sugar is selected from the group consisting of a monosaccharide, a disaccharide, a trisaccharide, a tetrasaccharide, a pentasaccharide, a hexasaccharide, a heptasaccharide, an octasaccharide, and a nonasaccharide.

BRIEF DESCRIPTION OF THE DRAWINGS

FIG. 5 shows a summary of heparosan synthase kinetics.

FIG. 11 shows XTalPredRF analysis of PmHS2 protein sequence (SEQ ID NO:4).

FIG. 12 shows the gene (SEQ ID NO:5) and protein (SEQ ID NO:6) sequences of $His_6$-PmHS2. The DNA sequence and the corresponding amino acid residues that come from the vector including an N-terminal $His_6$-tag (SEQ ID NO: 14) are italicized.

FIG. 13 shows the gene (SEQ ID NO:7) and protein (SEQ ID NO:3) sequences of $His_6$-Δ80PmHS2. The DNA sequence and the corresponding amino acid residues that come from the vector including an N-terminal $His_6$-tag (SEQ ID NO: 14) are italicized.

DETAILED DESCRIPTION OF THE INVENTION

Figures 1, 2:
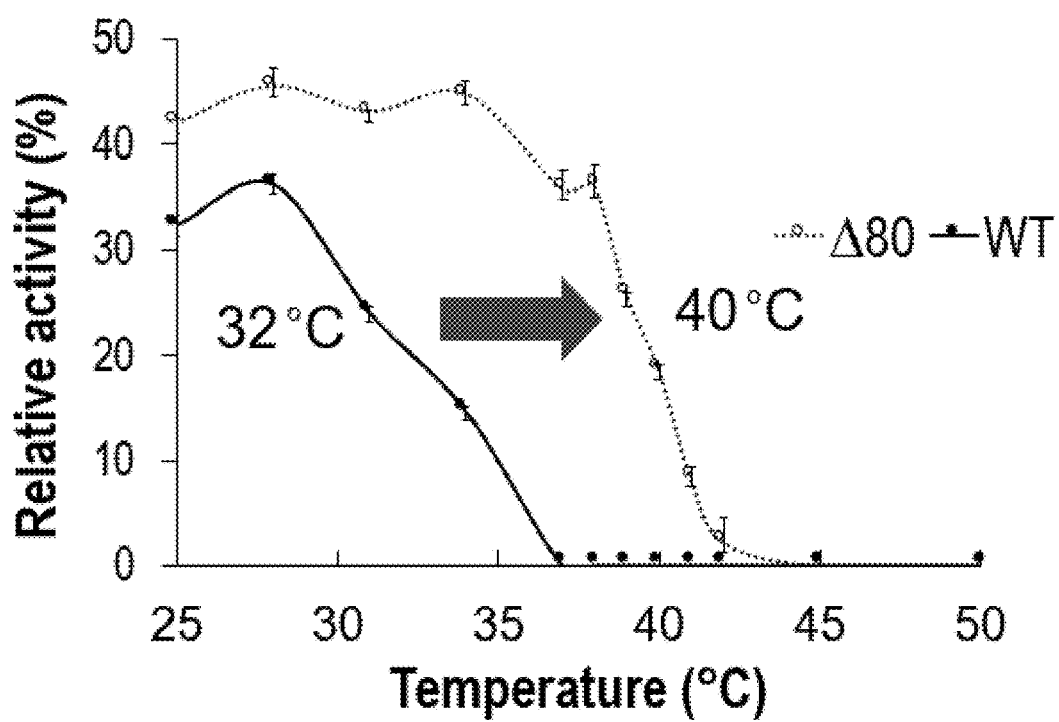
FIG. 1 shows a bioinformatics analysis showed that N-terminal sequence includes coiled coils and longest disordered region (SEQ ID NO:2; bold: coiled coils; underlined: disordered; superscript: helix; italic: low complexity; black: loop).
FIG. 2 shows the results of a thermal stability assay, indicated that $His_6$-Δ80PmHS2 has an increased Tso (temperature is required to 50% maximum activity) with respect to wild-type.
Figures 3, 4:
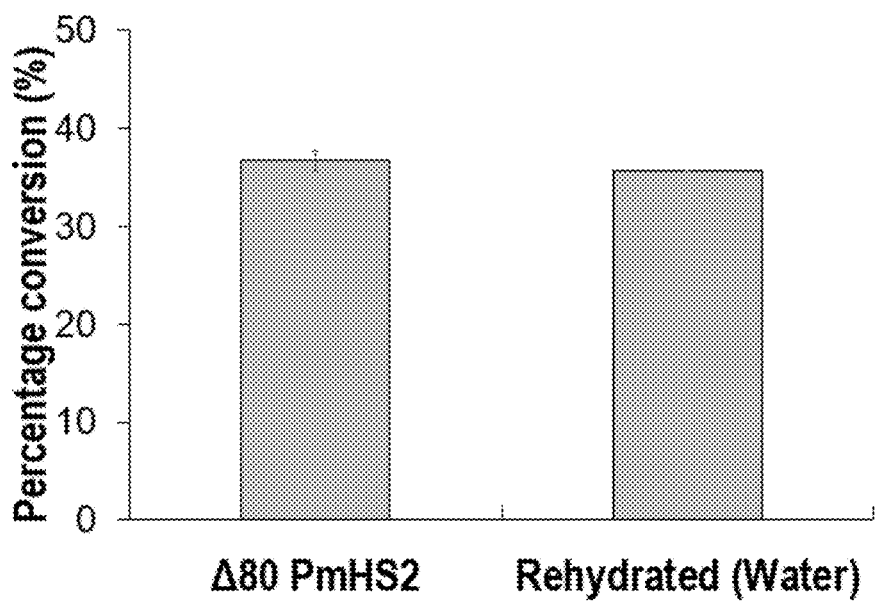
FIG. 3 shows the activity of $His_6$-Δ80PmHS2 after dialysis followed by lyophilization (right column) showed similar activity compared to freshly prepared $His_6$-Δ80PmHS2
FIG. 4 shows the effect of UDP concentration on reverse glycosylation.
Figure 6:
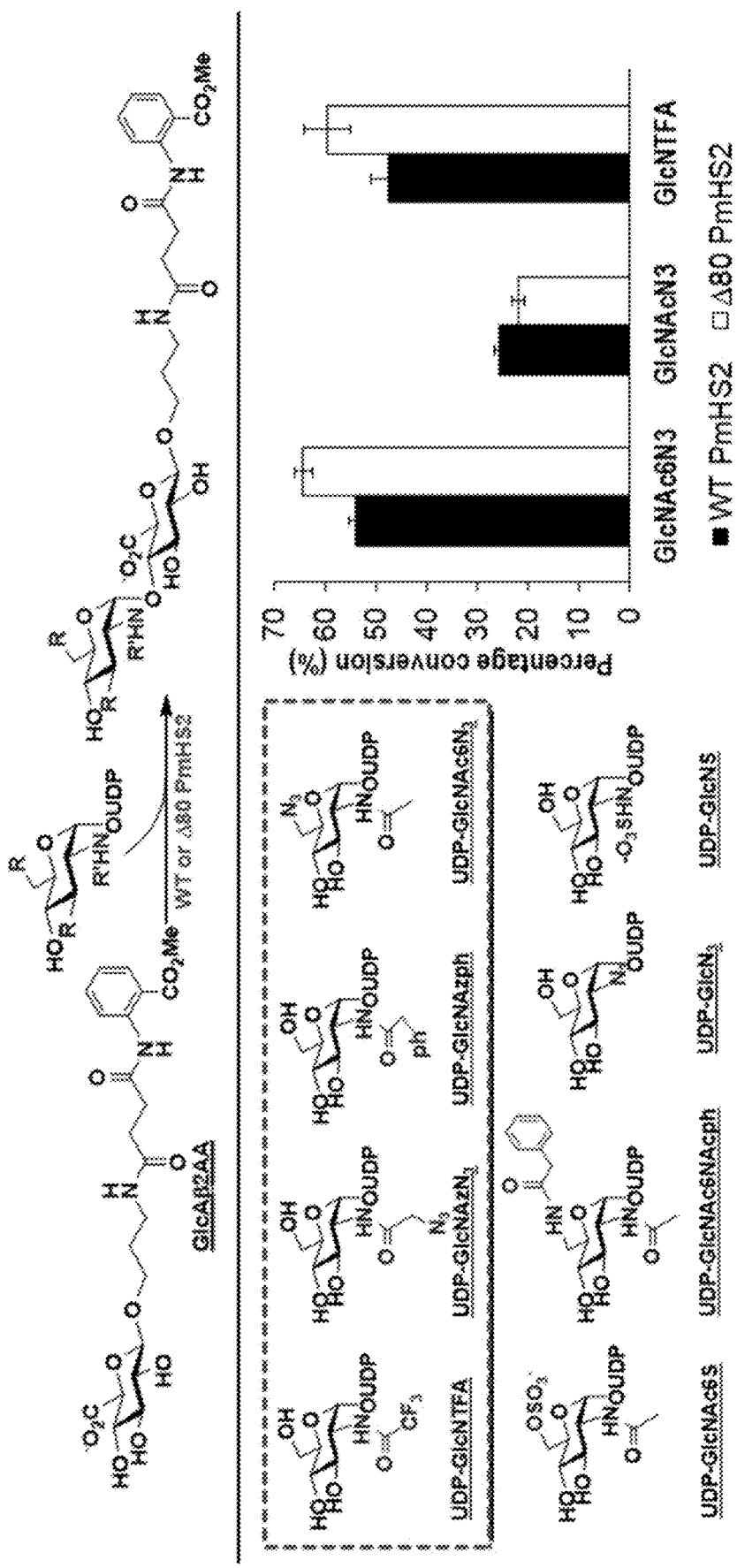
FIG. 6 shows a summary of heparosan synthase substrate tolerance.
Figure 7:
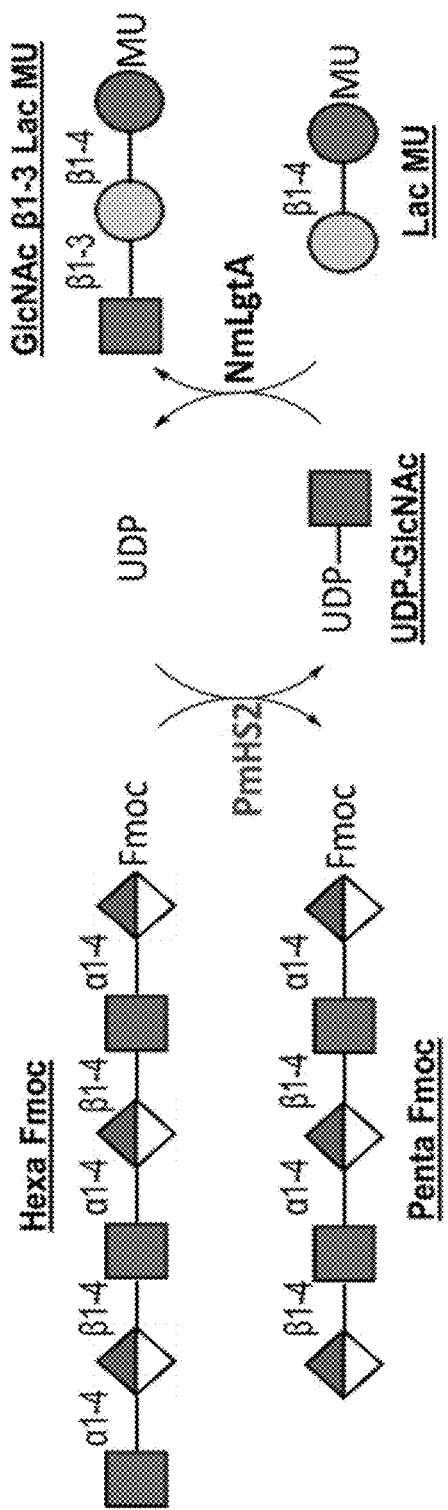
FIG. 7 shows a schematic of a couple enzyme assay for detection of UDP-GlcNAc.
Figure 8:
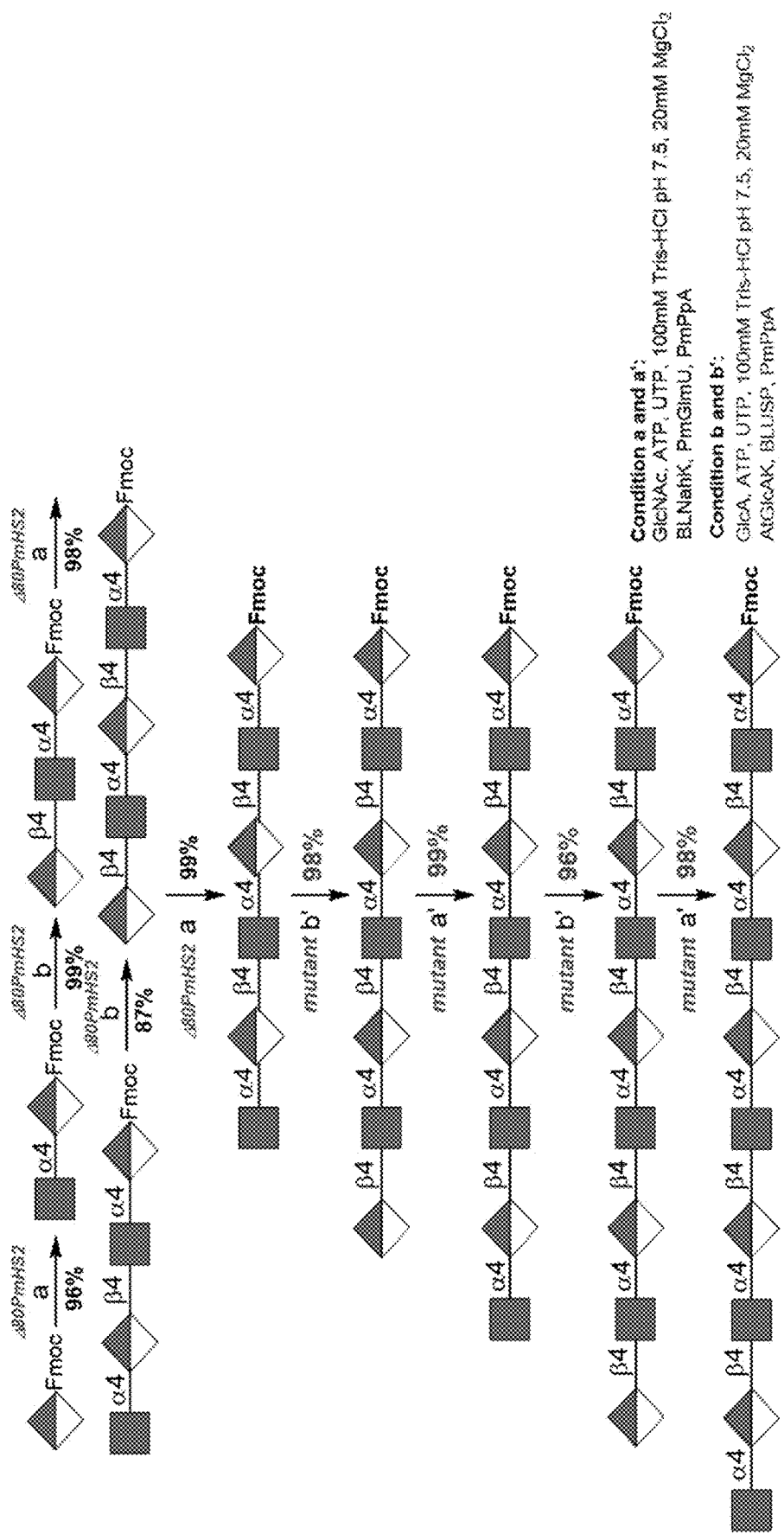
FIG. 8 shows a schematic of mutant driven efficient size-controlled synthesis of non-modified heparan sulfate.
Figure 9:
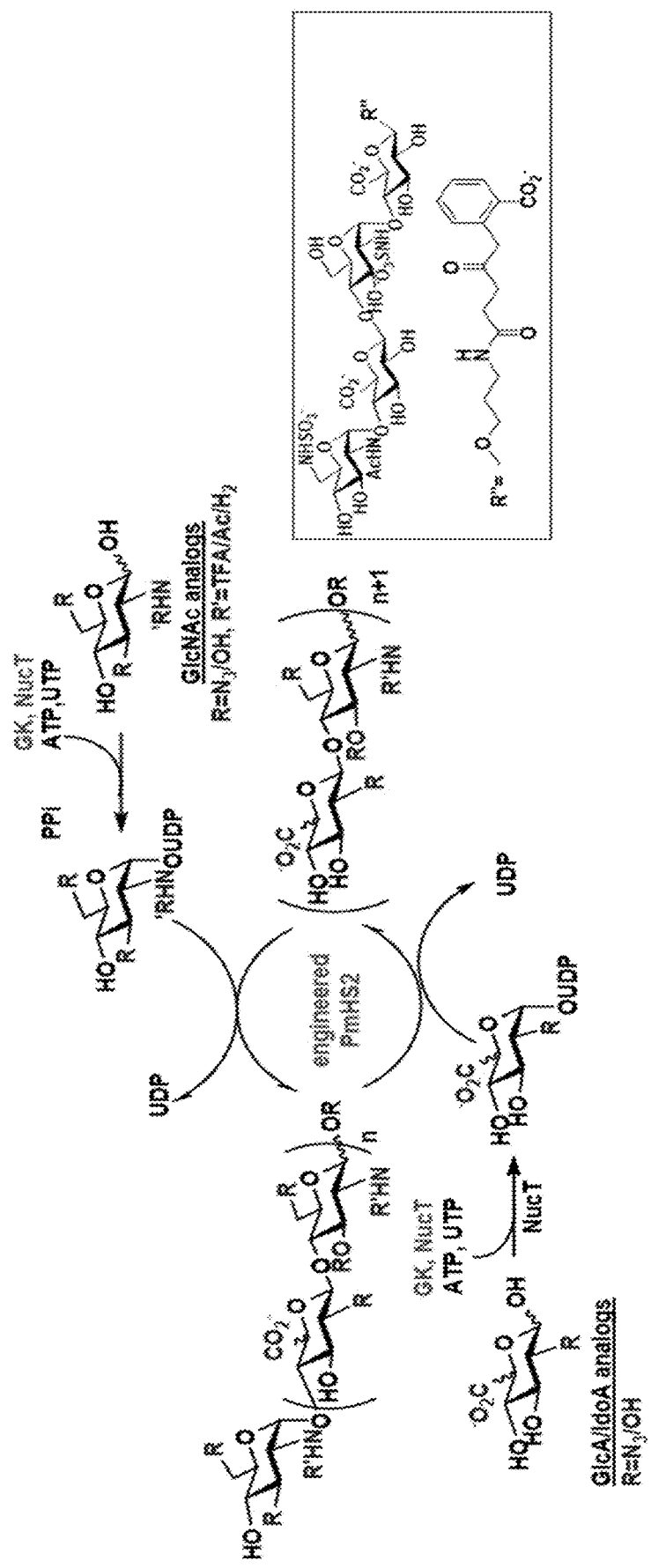
FIG. 9 shows a schematic of one-pot multi enzyme (OPME) synthesis of heparan sulfate analogs.
Figure 10:
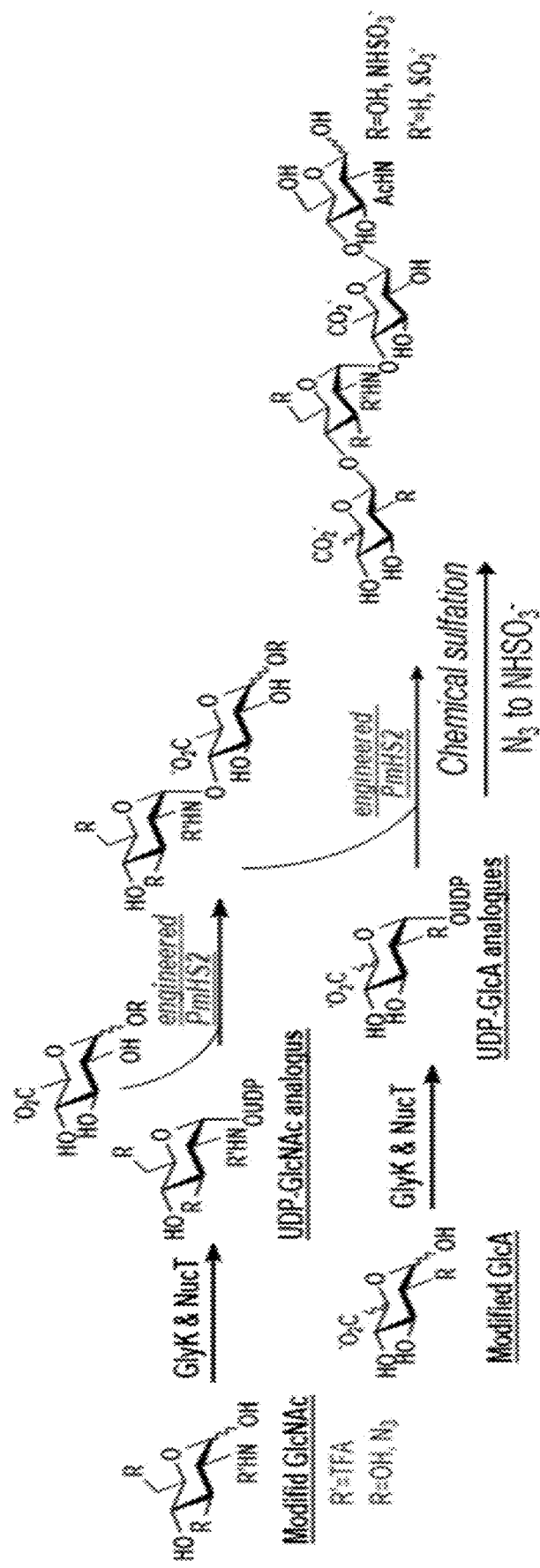
FIG. 10 shows a schematic of one-pot multi enzyme (OPME) synthesis of heparan sulfate analogs.

Provided herein are *Pasteurella multocida* heparosan synthase 2 (PmHS2) variants having improved functional properties. We disclose here the identification of PmHS2 mutants with desired improved functions.

An N-terminal His$_6$-tagged (SEQ ID NO: 14) and N-terminal 80 amino acid-truncated PmHS2 (His$_6$-Δ80PmHS2) was initially designed. This truncated enzyme was found to possess enhanced thermal stability and expression level compared to WT His$_6$-PmHS2. His$_6$-Δ80PmHS2 showed a 3-4 fold increase in expression level (60-80 mg/L) compared to WT (17-20 mg/L). The Tso (the temperature at which the enzyme retains 50% of maximum activity) was increased by approximately 7° C. for His$_6$-Δ80PmHS2 compared to WT, indicating a high likelihood for improved stability. The efficacy of His$_6$-Δ80PmHS2 was demonstrated by gram-scale synthesis of heparosan oligosaccharides ranging from disaccharides to hexasaccharides.

Similar to WT His$_6$-PmHS2, His$_6$-Δ80PmHS2 retained significant reverse glycosylation activity, especially when the size of the heparosan oligosaccharide acceptor has length equal to or larger than hexasaccharide, which contributed to lower yields of oligosaccharides with a lengths longer than heptasaccharides. To minimize byproduct formation during enzymatic and chemoenzymatic synthesis of heparosan oligosaccharides, Asp291 and Asp569 were identified as the key catalytic residues associated with the transfer of GlcA and GlcNAc, respectively. Furthermore, His$_6$-Δ80PmHS2_D222N and His$_6$-Δ80PmHS2_D500N mutants were designed as mono-functional GlcNAc transferase and GlcA transferase, respectively. The mutants remarkably reduced the reverse glycosylation while retaining the substrate promiscuity of His$_6$-PmHS2 for the synthesis of longer heparosan oligosaccharides, heparin, and heparan sulfate oligosaccharide analogs.

To increase the substrate promiscuity of His$_6$-PmHS2 and His$_6$-Δ80PmHS2, Y176, R195, L196, F198, I199, T200, and/or N248 were identified as hot spot amino acid residues for tolerating UDP-GlcA2N3 as a donor substrate. More specifically, Y176A, R195A, L196A, F198A, I199A, T200A, and/or N248A were proposed for tolerating UDP-GlcA2N3 as a donor substrate.

In addition, K390, L473, T475, T477, and V478 were identified as hot spot amino acid residues for incorporating GlcNAc3N3. It is believed that mutations of one or more of these residue to a smaller amino acid residue such as Alanine (A) would lead to the tolerance of UDP-GlcNAc3N$_3$ as a donor substrate.

Lastly, S496, G497, and M498 were identified as hot spots for tolerating UDP-GlcNAc6S as a donor substrate. S496N, S496A, G497 deletion mutations, and M498A would lead to the tolerance of UDP-GlcNAc6S as a donor substrate.

"Identical" and "identity," in the context of two or more nucleic acids or polypeptide sequences, refer to two or more sequences or subsequences that are the same. Sequences are "substantially identical" to each other if they have a specified percentage of nucleotides or amino acid residues that are the same (e.g., at least 75%, at least 80%, at least 85%, at least 90%, at least 95%, or at least 99% identical over a specified region), when compared and aligned for maximum correspondence over a comparison window, or designated region as measured using one of the following sequence comparison algorithms or by manual alignment and visual inspection. These definitions also refer to the complement of a nucleic acid test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below can be used. The BLAST and BLAST 2.0 algorithms are described in Altschul et al., (1990) *J Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

In certain embodiments, a Δ80PmHS2 variant according to the present disclosure will comprise a polypeptide having at least about 70%, e.g., at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to the amino acid sequence set forth in SEQ ID NO:1.

```
(Δ80PmHS2)
                                                     SEQ ID NO: 1
         10         20         30         40
FEKIYTYNQA LEAKLEKDKQ TTSITDLYNE VAKSDLGLVK 50         60         70         80
ETNSANPLVS IIMTSHNTAQ FIEASINSLL LQTYKNIEII 90        100        110        120
IVDDDSSDNT FEIASRIANT TSKVRVFRLN SNLGTYFAKN 130        140        150        160
TGILKSKGDI IFFQDSDDVC HHERIERCVN ILLANKETIA 170        180        190        200
VRCAYSRLAP ETQHIIKVNN MDYRLGFITL GMHRKVFQEI 210        220        230        240
GFFNCTTKGS DDEFFHRIAK YYGKEKIKNL LLPLYYNTMR 250        260        270        280
ENSLFTDMVE WIDNHNIIQK MSDTRQHYAT LFQAMHNETA 290        300        310        320
SHDFKNLFQF PRIYDALPVP QEMSKLSNPK IPVYINICSI 330        340        350        360
PSRIAQLQRI IGILKNQCDH FHIYLDGYVE IPDFIKNLGN
```

-continued

```
       370        380        390        400
KATVVHCKDK DNSIRDNGKF ILLEELIEKN QDGYYITCDD 410        420        430        440
DIIYPSDYIN TMIKKLNEYD DKAVIGLHGI LFPSRMTKYF 450        460        470        480
SADRLVYSFY KPLEKDKAVN VLGTGTVSFR VSLFNQFSLS 490        500        510        520
DFTHSGMADI YFSLLCKKNN ILQICISRPA NWLTEDNRDS 530        540        550        560
ETLYHQYRDN DEQQTQLIME NGPWGYSSIY PLVKNHPKFT 570        571
DLIPCLPFYF L
```

Also provided herein are N-terminal $His_6$-tagged (SEQ ID NO: 14) N-terminal 80 amino acid truncated *Pasteurella multocida* heparosan synthase 2 ($His_6$-Δ80PmHS2) variants comprising a polypeptide having at least 70% identity to the amino acid sequence set forth in SEQ ID NO:3.

In some embodiments, the $His_6$-Δ80PmHS2 variant consists of the polypeptide having at least 70% identity to the amino acid sequence set forth in SEQ ID NO:3. In certain embodiments, the $His_6$-Δ80PmHS2 variant comprises a mutation at one or more positions corresponding to Y176, R195, L196, F198, I199, T200, D222, N248, K390, L473, T475, T477, V478, S496, G497, M498, and D500 in SEQ ID NO:3. In certain embodiments, the $His_6$-Δ80PmHS2 variant comprises one or more mutations corresponding to Y176A, R195A, L196A, F198A, I199A, T200A, D222N, N248A, K390A, L473A, T475A, T477A, V478A, S496N, S496A, G497 deletion, M498A, and D500N in SEQ ID NO:3.

In particular embodiments, the PmHS2 variant comprises the mutation D222N or D500N in SEQ ID NO:3. In particular embodiments, the $His_6$-Δ80PmHS2 variant comprises the mutations D410N, D412N, and D500N in SEQ ID NO:3. In particular embodiments, the PmHS2 variant comprises the mutation with G497 deletion in SEQ ID NO:3. In particular embodiments, the $His_6$-Δ80PmHS2 variant comprises the mutations Y176A, R195A, L196A, F198A, I199A, T200A, and/or N248A in SEQ ID NO:3. In particular embodiments, the $His_6$-Δ80PmHS2 variant comprises the mutations K390A, L473A, T475A, T477A, and/or V478A in SEQ ID NO:3. In particular embodiments, the PmHS2 variant comprises the mutations S496N, S496A, and/or M498A in SEQ ID NO:3.

Also provided herein are methods for preparing oligosaccharides and polysaccharides, including heparin analogs and heparan sulfate analogs. In some embodiments, the methods include: forming a mixture containing (i) a heparosan synthase variant as described herein, (ii) an acceptor sugar, and (iii) a nucleotide sugar comprising a nucleotide moiety and a donor sugar moiety; and maintaining the mixture under conditions sufficient to transfer the donor sugar moiety to the acceptor sugar.

In some embodiments, the nucleotide sugar in the mixture is formed by converting a sugar starting material to the nucleotide sugar. One or more additional enzymes can be used to convert a sugar starting material (e.g., a monosaccharide) to a nucleotide sugar or another sugar intermediate useful in the preparation of the desired end product. Such enzymes may include, but are not limited to, glycosyltransferases, nucleotide-sugar pyrophosphorylases, kinases, and dehydrogenases, examples of which are described in WO 2013/013244. Such enzymes can be used in conjunction with the heparosan synthase variants of the present disclosure in one-pot, multi-enzyme reactions.

In some embodiments, the sugar starting material is selected from:

In some embodiments, the acceptor sugar is selected from the group consisting of a monosaccharide, a disaccharide, a trisaccharide, a tetrasaccharide, a pentasaccharide, a hexasaccharide, a heptasaccharide, an octasaccharide, and a nonasaccharide.

In some embodiments, the sugar starting material is selected from substituted or unsubstituted glucose (Glc), substituted or unsubstituted glucose-1-phosphate (Glc-1-P), substituted or unsubstituted glucuronic acid (GlcA), substituted or unsubstituted glucuronic acid-1-phosphate (GlcA-1-P), substituted or unsubstituted iduronic acid (IdoA), substituted or unsubstituted iduronic acid-1-phosphate (IdoA-1-P), substituted or unsubstituted N-acetylglucosamine (GlcNAc), substituted or unsubstituted N-acetylglucosamine-1-phosphate (GlcNAc-1-P), substituted or unsubstituted glucosamine ($GlcNH_2$), substituted or unsubstituted glucosamine-1-phosphate ($GlcNH_2$-1-P), substituted or unsubstituted galactose (Gal), substituted or unsubstituted galactose-1-phosphate (Gal-1-P), substituted or unsubstituted galacturonic acid (GalA), substituted or unsubstituted galacturonic acid-1-phosphate (GalA-1-P), substituted or unsubstituted N-acetylgalactosamine (GalNAc), substituted or unsubstituted N-acetylgalactosamine-1-phosphate (GalNAc-1-P), substituted or unsubstituted galactosamine ($GalNH_2$), substituted or unsubstituted galactosamine-1-phosphate ($GalNH_2$-1-P), substituted or unsubstituted mannose (Man), substituted or unsubstituted mannose-1-phosphate (Man-1-P), and substituted or unsubstituted N-acetylmannosamine (ManNAc), substituted or unsubstituted N-acetylmannosamine-1-phosphate (ManNAc-1-P), substituted or unsubstituted mannosamine (ManNH2), and substituted or unsubstituted mannosamine-1-phosphate (ManNH2-1-P).

In some embodiments, the sugar starting material is GlcNAc, a GlcNAc analog, GlcA, or a GcA analog.

In some embodiments, the sugar starting material is a GlcNAc analog having a formula:

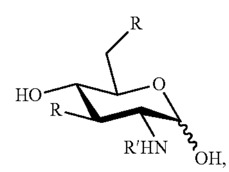

wherein R' is selected from the group consisting of acetyl and trifluoroacetyl, and each R is independently selected from —OH and —$N_3$.

In some embodiments, the sugar starting material is a GlcA analog having a formula:

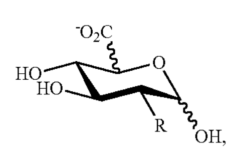

wherein R is selected from —OH and —$N_3$.

In some embodiments, the sugar starting material is selected from

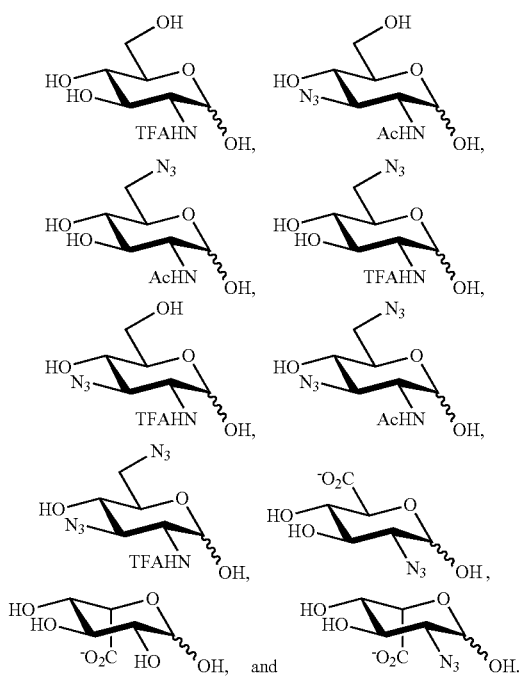

In some embodiments, preparing the saccharide end product includes converting an —$N_3$ group in a sugar starting material or a sugar intermediate to an $NHSO_3^-$ group.

EXAMPLES

Example 1 Generation of $His_6$-$\Delta$80PmHS2

Figure 14A:
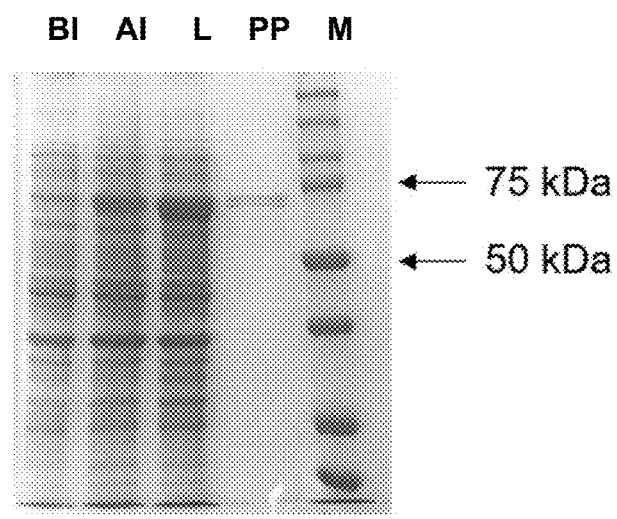
FIGS. 14A and 14B show protein expression and purification of $His_6$-PmHS2 (14A) and $His_6$-Δ80PmHS2 (14B). Lanes: BI, whole cell extract before induction; AI, whole cell extract after induction; L, lysate after induction; PP, Ni2+-NTA column purified protein; M, protein markers (Bio-Rad precision Plus Protein Standards, 10-250 kDa).
Figure 14B:
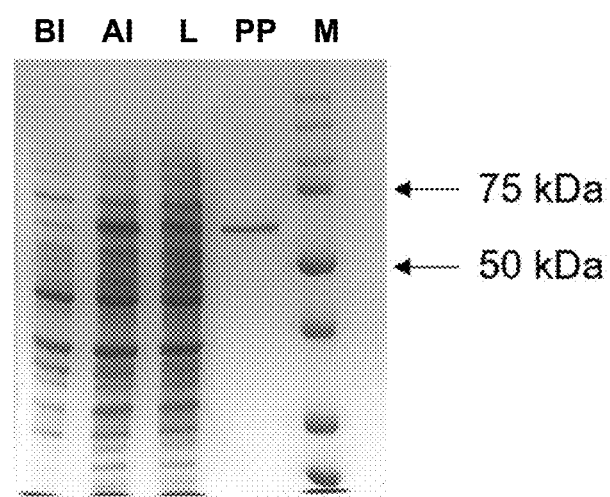
Figure 15:
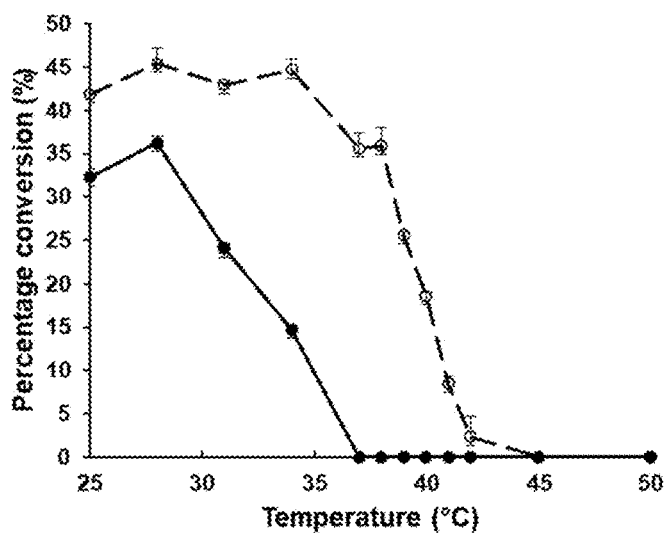
FIG. 15 shows the thermal stability assays of $His_6$-PmHS2 (filled circles with solid line) and $His_6$-Δ80PmHS2 (open circle with dashed line).
Figure 16:
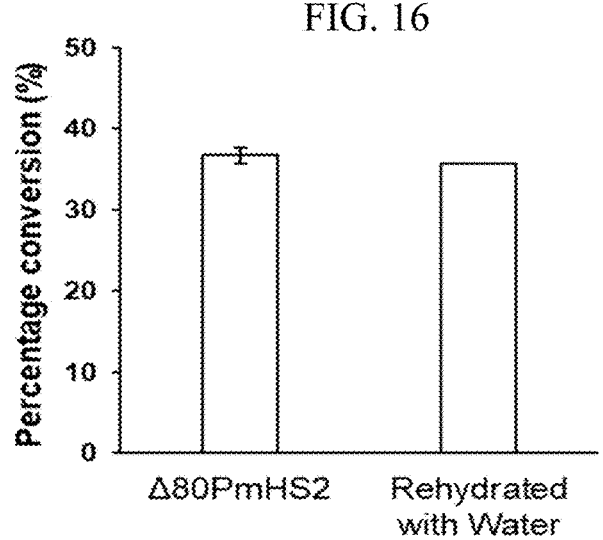
FIG. 16 shows the activity comparison of freshly purified $His_6$-Δ80PmHS2 and the sample after lyophilization and rehydration with ddH2O (4° C.).
Figure 17:
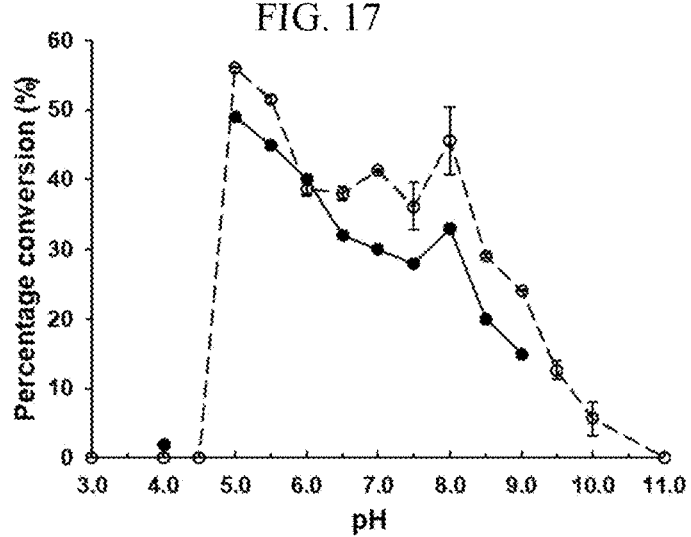
FIG. 17 shows the pH profiles of the GlcNAc transferase activities of $His_6$-PmHS2 (filled circles with solid line)' and $His_6$-Δ80PmHS2 (open circles with dashed line). Buffers used: citrate, pH 3.0-4.0; NaOAc/HOAc, pH 4.5; MES, pH 5.0-6.0; Tris-HCl, pH 7.0-9.0; N-cyclohexyl-3-aminopropanesulfonic acid (CAPS), pH 10.0-11.0.
Figure 18:
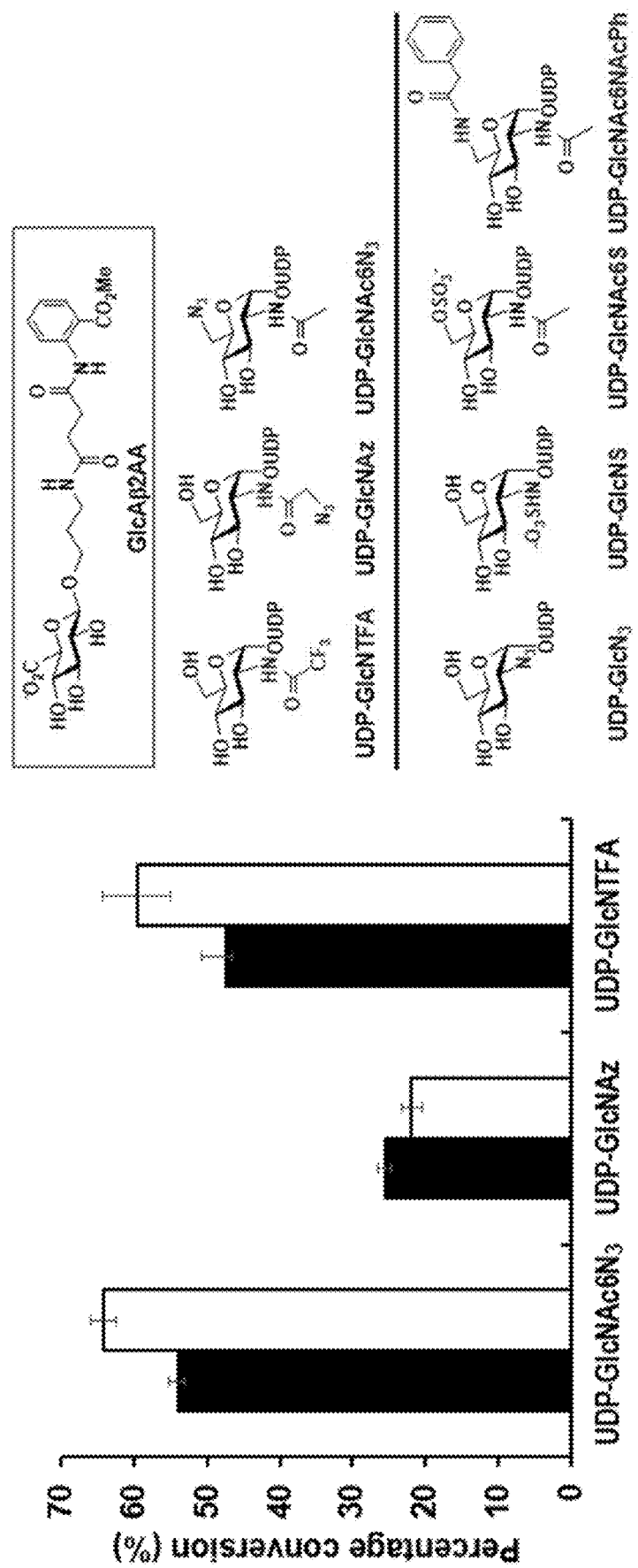
FIG. 18 shows HPLC-based donor substrate specificity comparison of the N-acetylglucosaminyltransferase (GlcNAcT) activities of $His_6$-PmHS2 (black columns) and $His_6$-Δ80PmHS2 (white columns). The list of seven different UDP-GlcNAc analogs tested is shown together with the structure of the acceptor used (GlcAβ2AA). While UDP-GlcNTFA, UDP-GlcNAz, and UDP-GlcNAc6N3 were suitable donor substrates for both enzymes, UDP-GlcN3, UDP-GlcNS, UDP-GlcNAc6S, and UDP-GlcNAc6NAcPh were not suitable donor substrates for either enzymes under the reaction conditions tested.

Analyzing PmHS2 protein sequence using XtalPredRF[31] (FIG. 11) and BLAST predicted that its N-terminal 80 amino acid residues might be nonessential to its glycosyltransferase activities and unfavorable for its crystallizability and stability. Indeed, removing the N-terminal 80 amino acid residues of $His_6$-PmHS2 (FIG. 12) (17-20 mg/L culture) resulted in $His_6$-$\Delta$80PmHS2 (FIG. 13) (60-80 mg/L) with a 3-4-fold improved expression level (FIGS. 14A and 14B) and an improved thermal stability (FIG. 15). In contrast to $His_6$-PmHS2 which precipitated easily during dialysis, $His_6$-$\Delta$80PmHS2 remained soluble. $His_6$-$\Delta$80PmHS2 could also survive lyophilization without loss of activity (FIG. 16). On the other hand, $His_6$-$\Delta$80PmHS2 (pI 6.61) and $His_6$-PmHS2[32] (pI 6.83) share similar pH profiles (FIG. 17) and donor substrate promiscuities (FIG. 18). A previously synthesized stable GlcAf32AA[18] was used as a fluorescent-labeled acceptor substrate in these assays to allow easy product detection by high-performance liquid chromatography (HPLC) with a diode array or UV/Vis detector.

Example 2 Substrate Testing

To facilitate reaction monitoring, product purification, and allow easy removal from the products for downstream conjugation with proteins or other molecules, a fluorophore tag was introduced to two possible monosaccharide substrates. GlcAr3ProNHFmoc (O1) and GlcNAcaProNHFmoc were synthesized from the corresponding glycosylpropylazides GlcAflProN$_3$[18] and GlcNAcaProN3[33] by catalytic hydrogenation followed by coupling with N-(9-fluorenylmethoxycarbonyloxy)succinimide (Fmoc-Suc) (see ESI).

Activity comparison (Table 1) showed that GlcAflProNHFmoc (O1) was a more efficient substrate than GlcNAcaProNHFmoc for both $His_6$-PmHS2 (157-fold) and $His_6$-$\Delta$80PmHS2 (130-fold) in disaccharide production. Apparent kinetics studies with GlcAPAA (Table 2) showed that $His_6$-PmHS2 (3.4±0.2 s-1) and $His_6$-$\Delta$80PmHS2 (3.5±0.2 s-1) have similar kcat values while $His_6$-PmHS2 (4.0±0.6 mM) has a lower KM value than $His_6$-$\Delta$80PmHS2 (5.3±0.7 mM), resulting in a slightly higher catalytic efficiency for $His_6$-PmHS2 (0.9 s-1 mM-1) than $His_6$-$\Delta$80PmHS2 (0.7 s-1 mM-1). Comparision of $His_6$-PmHS2 and $His_6$-$\Delta$80PmHS2 activities using GlcAflProNHFmoc (O1) or GlcNAcaProNHFmoc as an acceptor to form the corresponding disaccharide product GlcNAcal-4GlcAPProNHFmoc or GlcA$\beta$1-4GlcNAcaProNHFmoc (Percentage conversions for 30 min reactions determined by HPLC with an diode array detector are shown). Table 2 shows apparent kinetic parameters for $His_6$-PmHS2 and $His_6$-$\Delta$80PmHS2 using GlcAPAA as the acceptor. Data for repeated experiments of triplicates are shown.

TABLE 1

| Enzyme concentration | Enzyme | GlcNAcα1-4GlcAβProNHFmoc (%) | GlcAβ1-4GlcNAcαProNHFmoc (%) |
| --- | --- | --- | --- |
| 0.06 mg/mL | $His_6$-PmHS2 | 64.5 ± 1.0 | ND |
|  | $His_6$-$\Delta$80PmHS2 | 50.8 ± 6.0 | ND |
| 1.5 mg/mL | $His_6$-PmHS2 | 100 | 10.3 ± 0.3 |
|  | $His_6$-$\Delta$80PmHS2 | 100 | 9.8 ± 0.4 |

TABLE 2

|  | $k_{cat}$ (s$^{-1}$) | $K_M$ (mM) | $k_{cat}/K_M$ (s$^{-1}$ mM$^{-1}$) |
| --- | --- | --- | --- |
| $His_6$-PmHS2 | 3.4 ± 0.2 | 4.0 ± 0.6 | 0.9 |
| $His_6$-$\Delta$80PmHS2 | 3.5 ± 0.2 | 5.3 ± 0.7 | 0.7 |

Example 3 Oligosaccharide Synthesis

Starting from GlcAflProNHFmoc (O1), $His_6$-$\Delta$80PmHS2 with improved expression and stability permitted size-controlled gram-scale synthesis of heparosan oligosaccharides ranging from disaccharide (O2) to hexasaccharide (O6) in excellent yields using a sequential one-pot multienzyme (OPME) platform. In this platform (FIG. 19), GlcNAc-activation/transfer (OPME1) and GlcA-activation/transfer (OPME2) systems (each contains $His_6$-$\Delta$80PmHS2, a kinase, a nucleotidyltransferase, and an inorganic pyrophosphatase) were used alternately to extend the acceptor substrate chain one monosaccharide at a time. Each OPME reaction was carried out for 1-2 days, the product was purified and used as the acceptor substrate for the next OPME reaction.

Figure 19:
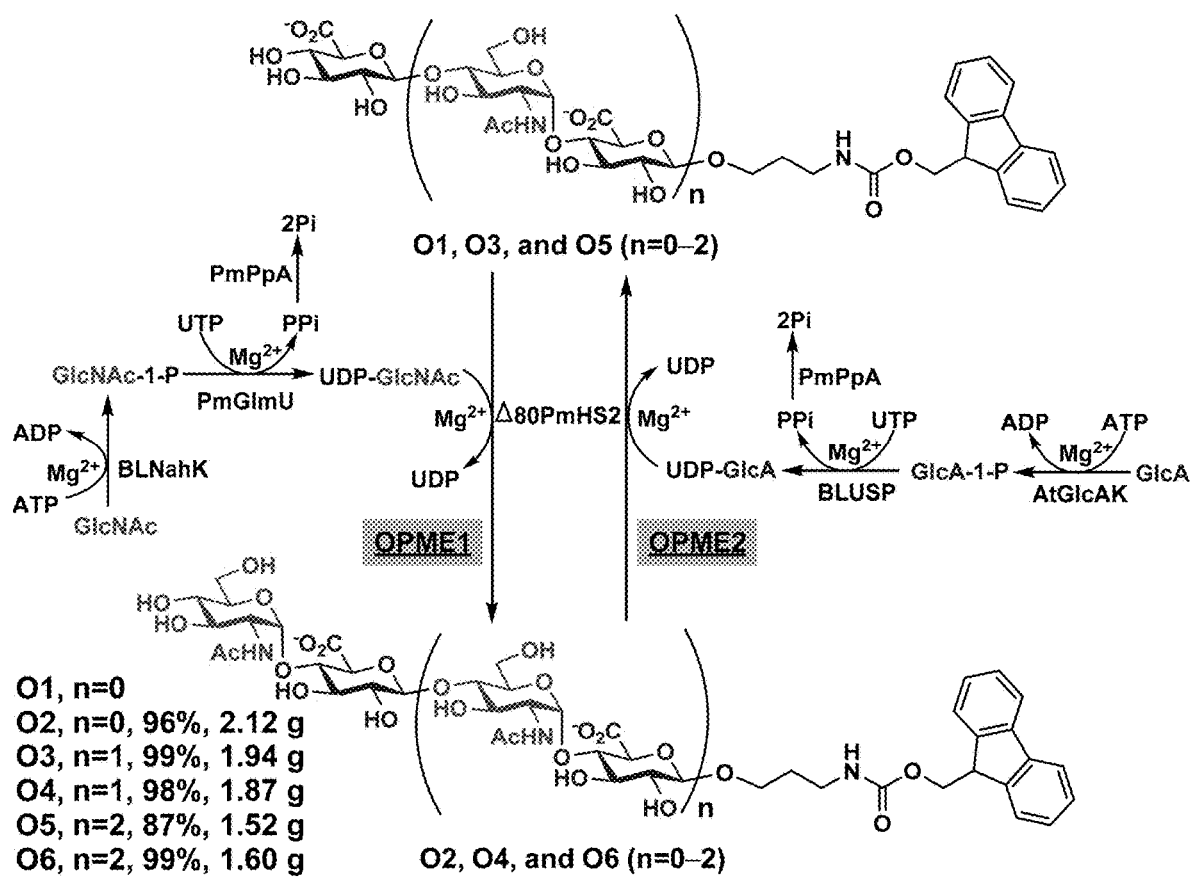
FIG. 19 shows $His_6$-Δ80PmHS2-dependent sequential one-pot multienzyme (OPME) synthesis of heparosan oligosaccharides O2-O6.

As shown in FIG. 19, disaccharide GlcNAcα1-4GlcAP-ProNHFmoc (O2) was enzymatically synthesized from O1 using a one-pot four-enzyme GlcNAc-activation and transfer system (OPME1) containing *Bifidobacterium longum* N-acetylhexosamine-1-kinase (BLNahK),[34] *Pasteurella multocida* N-acetylglucosamine-1-phosphate uridylyltransferase (PmGlmU),[35] *Pasteurella multocida* inorganic pyrophosphatase (PmPpA),[33] and His$_6$-Δ80PmHS2. The reaction went to completion and the product was readily purified by passing the reaction mixture through a C18 cartridge and eluting with a gradient solution of CH3CN in water. Purified disaccharide O2 (2.12 g) was obtained in an excellent 96% yield. Trisaccharide GlcAβ1-4GlcNAcα1-4GlcAP-ProNHFmoc (O3) (1.94 g) was synthesized from purified disaccharide O2 using a one-pot four-enzyme GlcA-activation and transfer system (OPME2) containing *Arabidopsis thaliana* glucuronokinase (AtGlcAK),[36] *Bifidobacterium longum* UDP-sugar pyrophosphorylase (BLUSP),[37] PmPpA, and His$_6$-Δ80PmHS2 with a purified yield of 99%. Repeating the alternate OPME1 and OPME2 reactions with C18-cartridge-based product purification after each OPME reaction led to the formation of tetrasaccharide O4 (1.87 g, 98%), pentasaccharide O5 (1.52 g, 87%), and hexasaccharide O6 (1.60 g, 99%).

OPME reactions of GlcNAc activation and transfer to glucuronides O1, O3, and O5 (OPME1) were highly efficient and N-acetylglucosaminides O2, O4, and O6 were obtained in nearly quantitative yields (96-99%). In the case of OPME reactions of GlcA activation and transfer to N-acetylglucosaminides O2 and O4 (OPME2) for the formation of glucuronides O3 and O5, the reaction with O2 went well and O3 was obtained in an excellent 99% yield. However, when tetrasaccharide O4 (an N-acetylglucosaminide longer than O2) was used as an acceptor for the formation of O5, the presence of O3 byproduct was observed, indicating that the terminal GlcNAc in the acceptor O4 was removed in the reaction. The side product formation was minimized by monitoring the reaction progress carefully and stopping the reaction promptly to obtain O5 in 87% yield.

Figure 20:
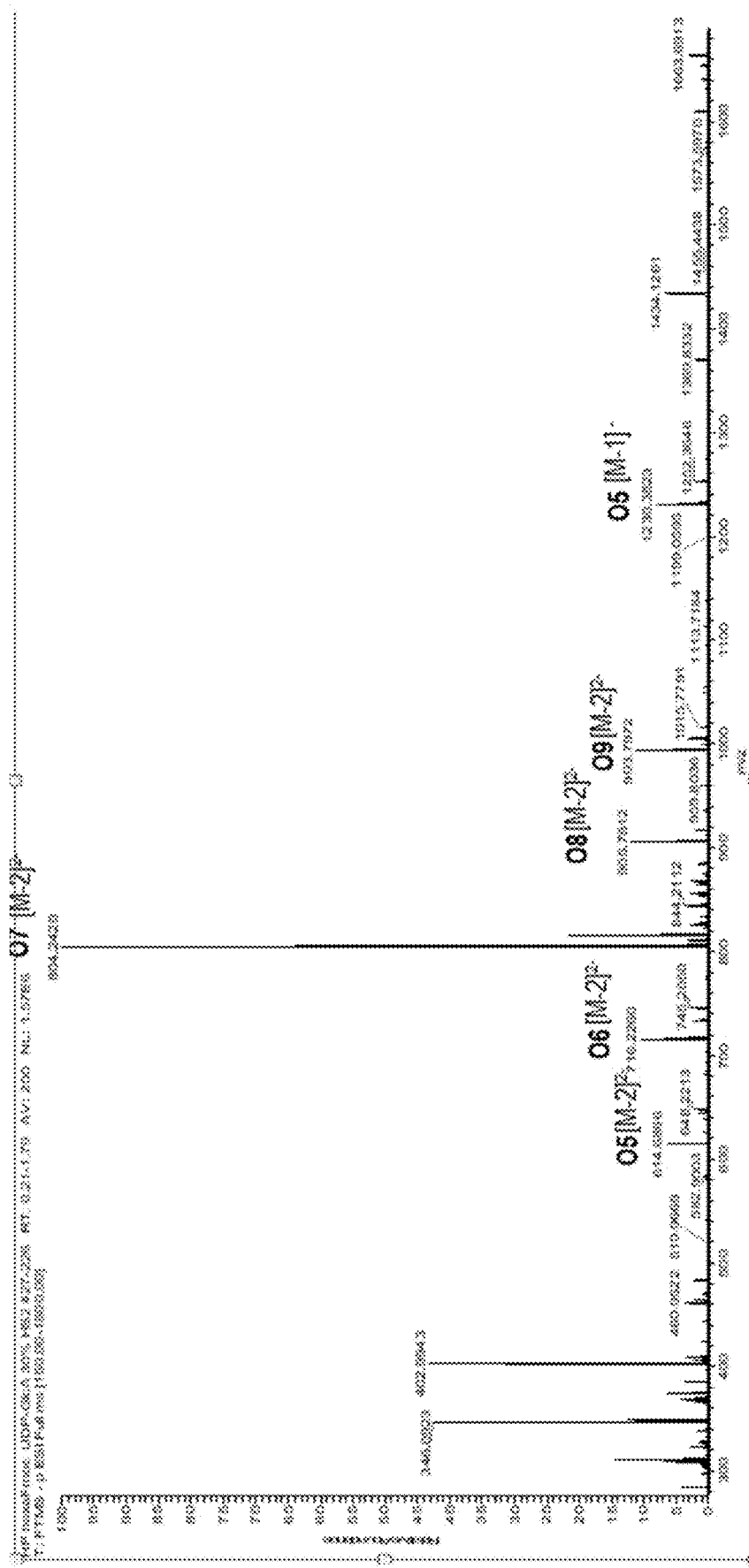
FIG. 20 shows a representative HRMS result for a reaction mixture of OPME synthesis of heptasaccharide O7 from hexasaccharide O6. Signals for M-1 molecular ions are labelled.

Overall, the sequential OPME platform containing His$_6$-Δ80PmHS2 was efficient in gram-scale synthesis of heparosan oligosaccharides up to hexasaccharide O6 from monosaccharide O1. When hexasaccharide O6 (an N-acetylglucosaminide even longer than O4) was used as the acceptor substrate for the β1-4-GlcAT activity of His$_6$-Δ80PmHS2, the formation of both longer and shorter oligosaccharide byproducts (FIG. 20) was observed, which complicated product purification and lowered synthetic yields.

Example 4 Reverse Glycosylation Activity of His$_6$-Δ80PmHS2

Figure 21:
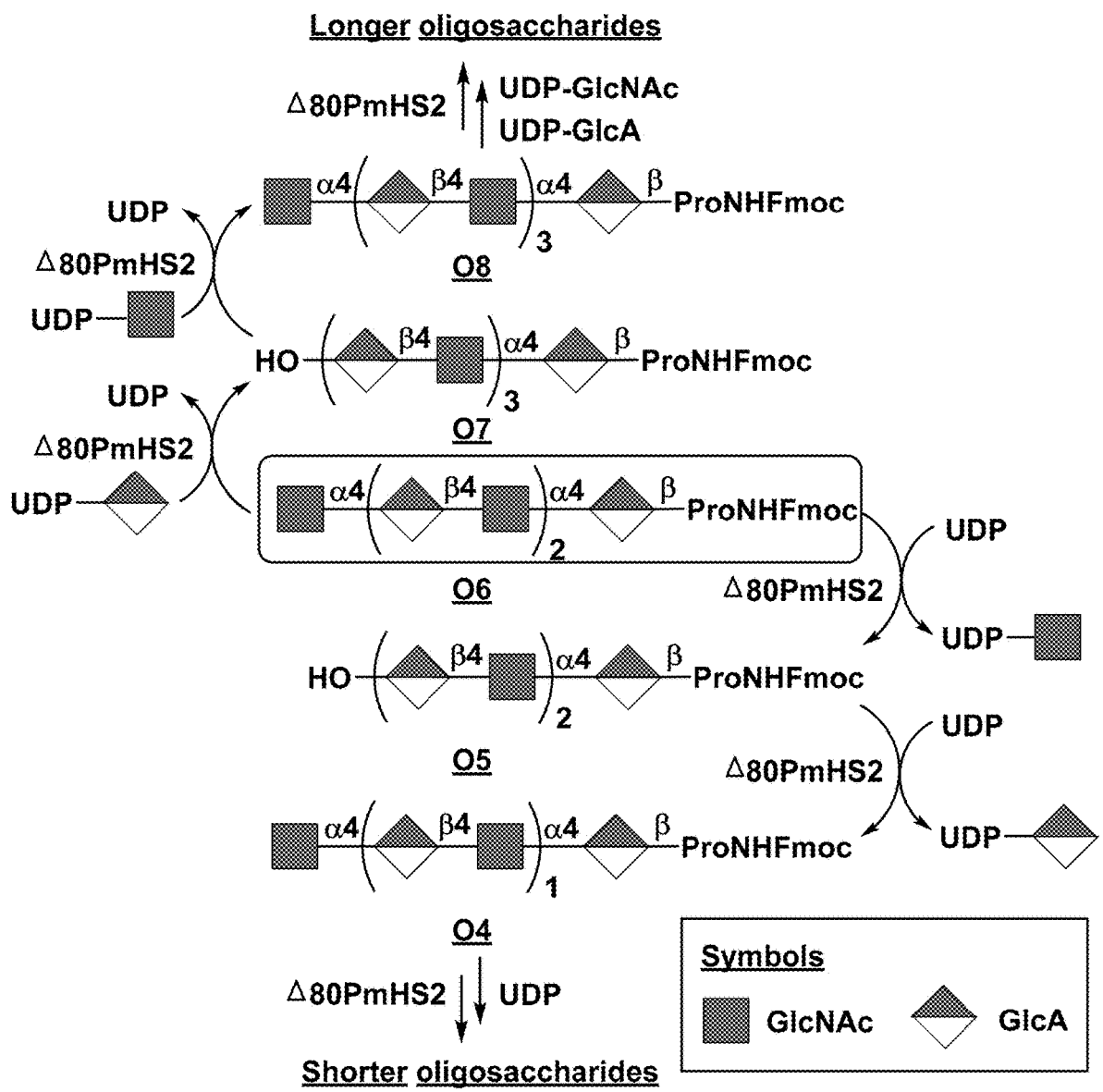
FIG. 21 shows a schematic illustration of the chain reactions caused by forward and reverse glycosylation activities of $His_6$-Δ80PmHS2 in the presence of hexasaccharide O6 and UDP.

It was hypothesized that the formation of longer and shorter oligosaccharide byproducts in the OPME reaction for the synthesis of O7 from O6 was due to the reverse glycosylation activity of His$_6$-Δ80PmHS2. Such activity was reported for some glycosyltransferases involved in natural product glycosylation,[38-39] mammalian sialyltransferases,[40] and bacterial sialyltransferases *Pasteurella multocida* sialyltransferase 1 (PmST1) and *Photobacterium damselae* α2-6-sialyltransferase (Pd2,6ST),[41-42] but was not observed for others.[40] Such activity, however, has never been shown for polysaccharide synthases. To test the hypothesis, hexasaccharide O6 was incubated with His$_6$-Δ80PmHS2 in the absence or the presence of different concentrations of uridine 5'-diphosphate (UDP). As shown in Table 3, the amounts of His$_6$-Δ80PmHS2 reverse glycosylation products (oligosaccharides of various sizes ranging from mono- to dodecasaccharide) increased and the concentration of O6 decreased significantly with the increase of UDP concentration. The same effects were observed for His$_6$-PmHS2 (Table 3), demonstrating that the reverse glycosylation property was not introduced by the N-terminal protein sequence truncation in His$_6$-Δ80PmHS2. The chain reactions caused by the forward and reverse glycosylation reactions of His$_6$-Δ80PmHS2 in the presence of O6 and UDP are illustrated in FIG. 21. Starting from O6, the reverse α1-4-GlcNAcT activity of His$_6$-Δ80PmHS2 produces O5 and UDP-GlcNAc. The resulting O5 is used by the reverse β1-4-GlcAT activity of His$_6$-Δ80PmHS2 to produce O4 and UDP-GlcA. On the other hand, the UDP-GlcA obtained is used together with O6 by the β1-4-GlcAT activity of His$_6$-Δ80PmHS2 to produce O7 and UDP. The α1-4-GlcNAcT activity of His$_6$-Δ80PmHS2 uses O7 and UDP-GlcNAc to produce O8 and UDP. Similarly, the newly formed longer and shorter oligosaccharides in the reaction mixture are used as the substrates in combined His$_6$-Δ80PmHS2-catalyzed forward and reverse glycosylation reactions for the formation of additional oligosaccharides of longer and shorter lengths. Table 3 shows the effect of UDP concentration (0-10 mM) on the reverse glycosylation activities of His$_6$-Δ80PmHS2 and His$_6$-PmHS2 (15 μM) by HPLC analyses when hexasaccharide O6 (1 mM) was used as the substrate.

TABLE 3

|  | UDP (nM) | O1 (%) | O2 (%) | O3 (%) | O4 (%) | O5 (%) | O6 (%) | O7 (%) | O8 (%) | O9 (%) | O10 (%) | O11 (%) | O12 (%) |
|---|---|---|---|---|---|---|---|---|---|---|---|---|---|
| His$_6$-Δ80PmHS2 | 0 | ND | ND | ND | ND | ND | 100 | ND | ND | ND | ND | ND | ND |
|  | 1 | ND | ND | ND | 6.7 ± 0.1 | 2.6 ± 0.4 | 81.6 ± 0.1 | ND | 7.9 ± 0.1 | ND | 0.8 ± 0.1 | ND | ND |
|  | 5 | 3.4 ± 0.4 | 1.5 ± 0.5 | 0.6 ± 0.1 | 16.9 ± 1.7 | 4.2 ± 1.0 | 58.0 ± 2.7 | 0.4 ± 0.1 | 12.8 ± 1.2 | ND | 1.9 ± 0.1 | ND | 0.2 ± 0.1 |
|  | 10 | 3.4 ± 0.2 | 7.8 ± 1.5 | 1.5 ± 0.5 | 18.9 ± 0.5 | 3.8 ± 0.1 | 38.0 ± 1.6 | 1.8 ± 0.2 | 18.6 ± 1.3 | 0.7 ± 0.1 | 4.2 ± 1.0 | ND | 1.1 ± 0.1 |
| His$_6$-PmHS2 | 0 | ND | ND | ND | ND | ND | 100 | ND | ND | ND | ND | ND | ND |
|  | 1 | 3.3 ± 0.2 | 2.7 ± 0.2 | 1.4 ± 0.1 | 9.6 ± 0.4 | 3.0 ± 0.6 | 64.2 ± 0.2 | ND | 13.5 ± 0.3 | ND | 1.9 ± 0.1 | ND | ND |
|  | 5 | 3.9 ± 0.2 | 5.5 ± 0.7 | 1.1 ± 0.2 | 8.8 ± 0.6 | 4.8 ± 2.4 | 52.3 ± 0.1 | 0.4 ± 0.1 | 16.0 ± 0.4 | ND | 5.7 ± 0.8 | ND | 0.7 ± 0.2 |
|  | 10 | 3.1 ± 0.1 | 9.0 ± 0.3 | 0.6 ± 0.1 | 17.7 ± 0.7 | 9.1 ± 0.1 | 36.2 ± 0.4 | 1.1 ± 0.2 | 16.3 ± 0.3 | 0.4 ± 0.1 | 4.6 ± 0.4 | ND | 1.3 ± 0.1 |

ND: not detected.

Figure 22:
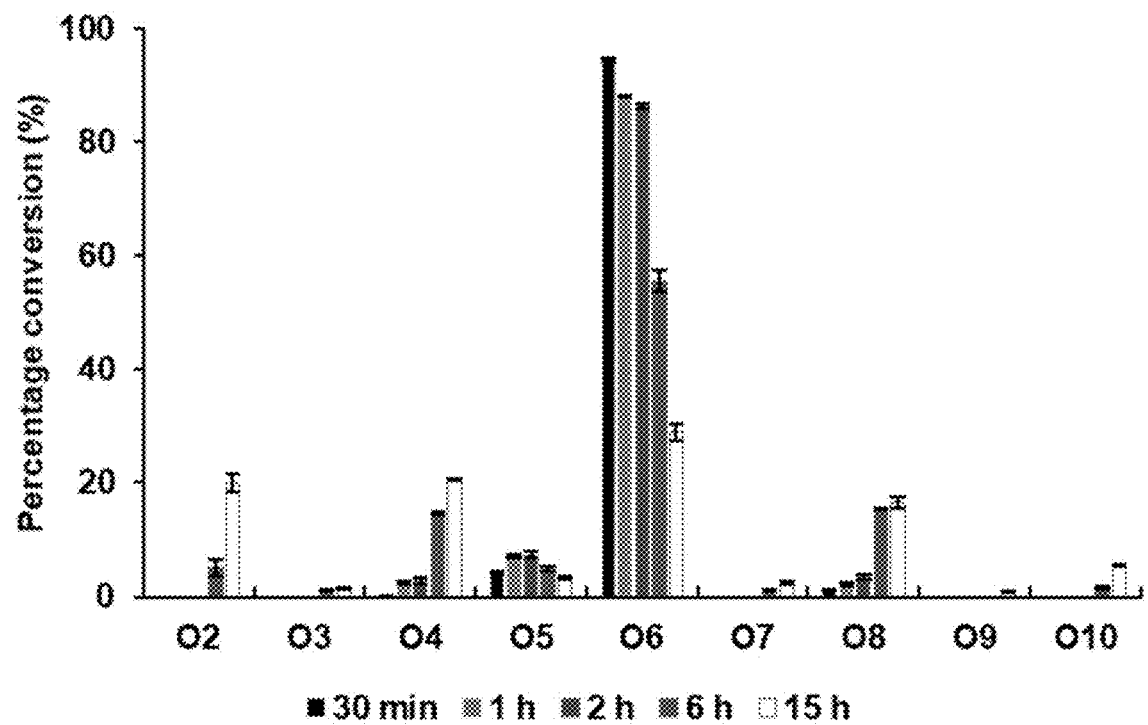
FIG. 22 shows time-course study results for the reverse glycosylation activity of $His_6$-Δ80PmHS2 (15 µM) in the presence of hexasaccharide O6 (1 mM) and UDP (10 mM) at 37° C. in MES buffer (100 mM, pH 6.5).
Figure 23:
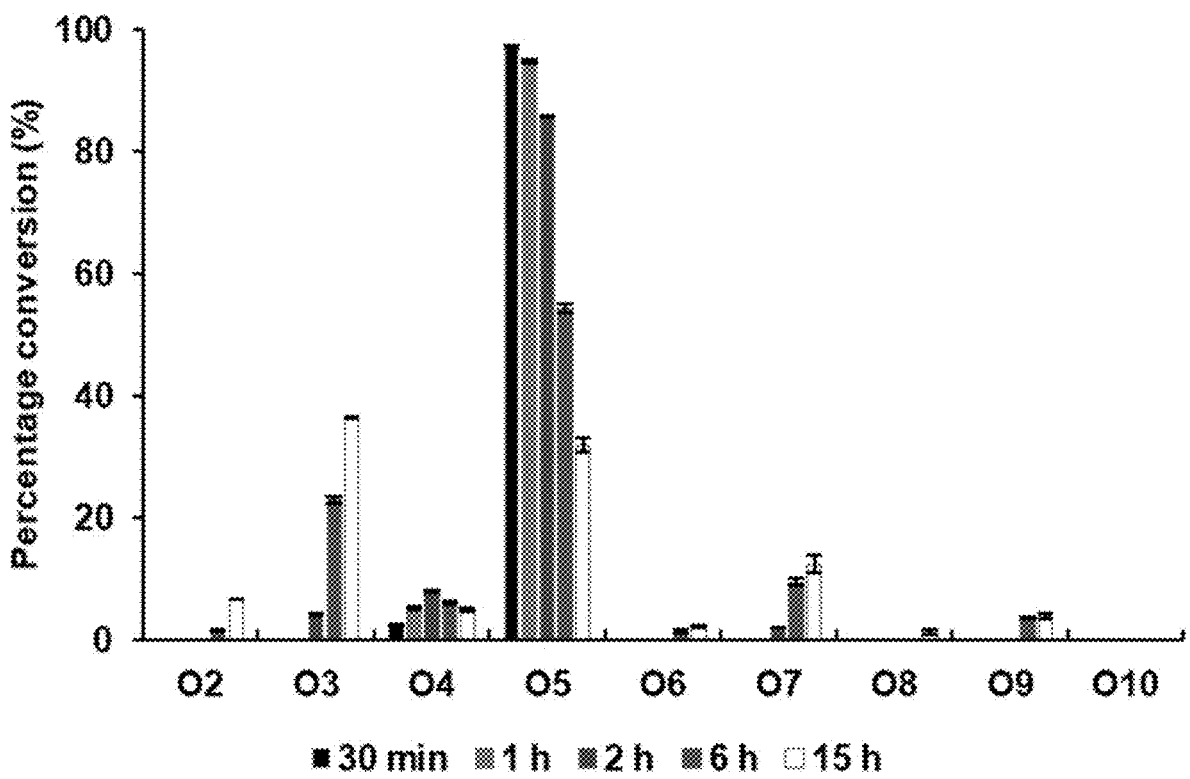
FIG. 23 shows time-course results for the reverse glycosylation activity of $His_6$-Δ80PmHS2 (15 µM) in the presence of pentasaccharide O5 (1 mM) and UDP (10 mM) at 37° C. in MES buffer (100 mM, pH 6.5).

Time course studies using GlcNAc-terminated O6 as the substrate for His$_6$-Δ80PmHS2 (FIG. 22) showed that longer incubation times led to a continuous decrease of O6 concentration and increased dispersity of oligosaccharide products with a preference toward the accumulation of GlcNAc-terminated oligosaccharides (O2, O4, O8, and O10). The production of oligosaccharides of different sizes indicated that both αl-4-GlcNAcT and β1-4-GlcAT activities of His$_6$-Δ80PmHS2 have the corresponding reverse glycosylation activities. Indeed, incubating His$_6$-Δ80PmHS2 with GlcA-terminated pentasaccharide O5 in the presence of UDP (FIG. 23) also showed a time-dependent increase of the product dispersity although GlcA-terminated oligosaccharide products (O3, O7, and O9) dominated. Increased product dispersity with the increase of time was also observed previously in His$_6$-PmHS2-catalyzed polymerization reactions,[15, 43] although reverse glycosylation was not realized as a likely major contributor.

Figure 24:
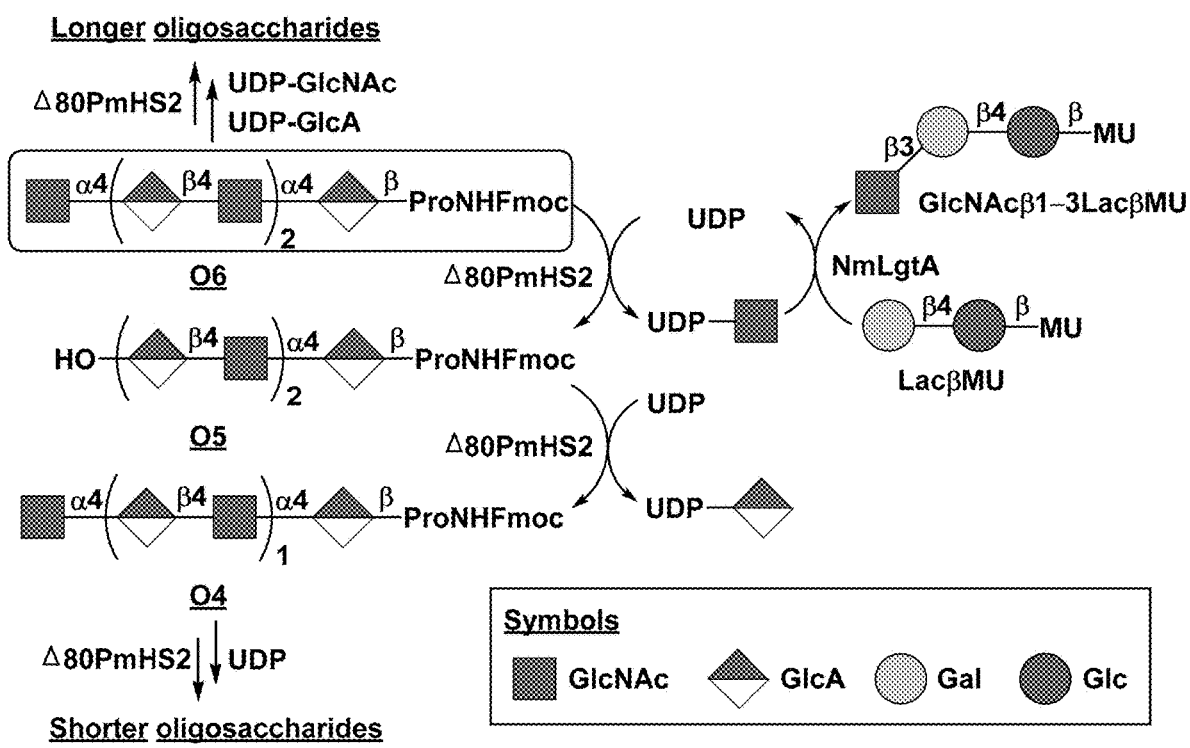
FIG. 24 shows schematic illustration for indirectly detecting UDP-GlcNAc formed in the reverse glycosylation reaction of $His_6$-Δ80PmHS2 in the presence of UDP and hexasaccharide O6 using a coupled enzyme assay with NmLgtA and LacβMU.
Figure 25A:
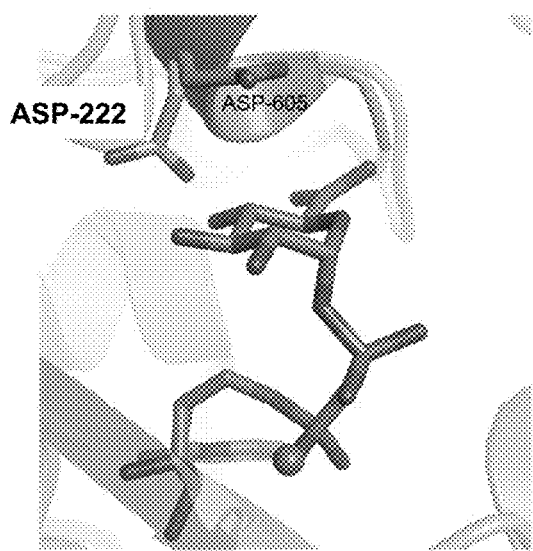
FIGS. 25A-25D show structure alignements of the β1-4-GlcAT domain of the $His_6$-Δ80PmHS2 I-TASSER model with the crystal structures of the EcKfoC GlcA-transferase (PDB ID: 2Z86) (A and C) and GalNAc-transferase (PDB ID: 2Z87) (B and D) domains. D222 of $His_6$-Δ80PmHS2 was superimposed with D605 and D362, the catalytic bases of the GlcA-transferase (A) and the GalNAc-transferase (B) domains of EcKfoC, respectively. Color code: cyan, EcKfoC; yellow, the GlcA-T domain of $His_6$-Δ80PmHS2 I-TASSER model.
Figure 25B:
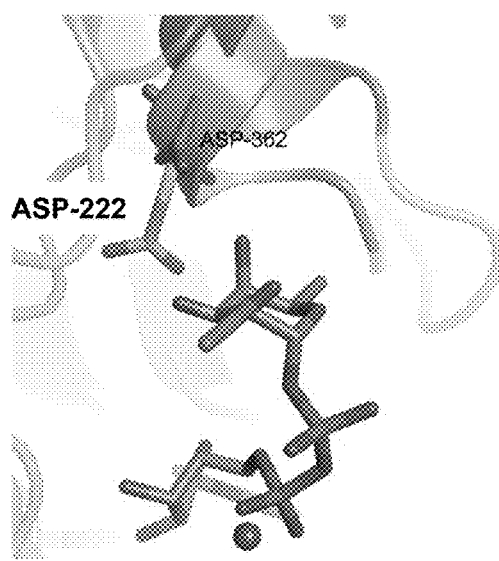
Figure 25C:
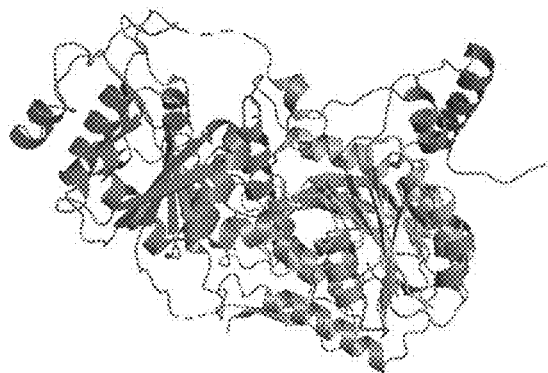
Figure 25D:
Figure 26A:
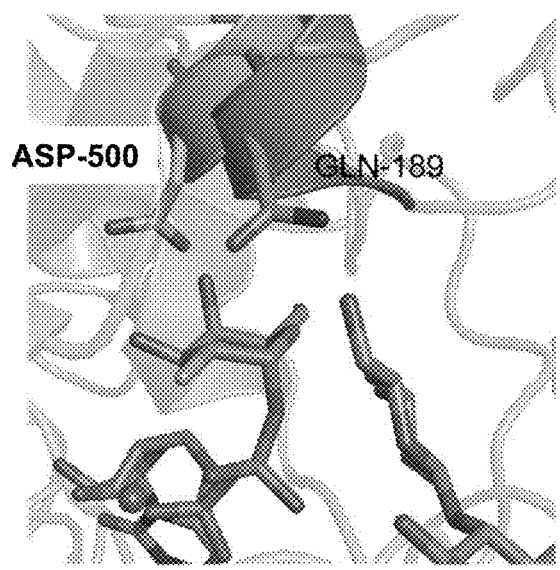
FIGS. 26A-26D show structure alignment of the α1-4-GlcNAcT domain of $His_6$-Δ80PmHS2 I-TASSER model with the crystal structures of NmLgtC (PDB ID: 1GA8) (A and C) and bovine α3GalT (PDB ID: 2VFZ) (B and D). D500 of $His_6$-Δ80PmHS2 was superimposed with Q189 (A) and E317 (B), the catalytic residues in NmLgtC and bovine α3GalT, respectively. Color code: cyan, UDP-2FGal and NmLgtC or UDP-2FGal and bovine α3GalT; yellow, the GlcNAc-T domain of $His_6$-Δ80PmHS2 I-TASSER model.
Figure 26B:
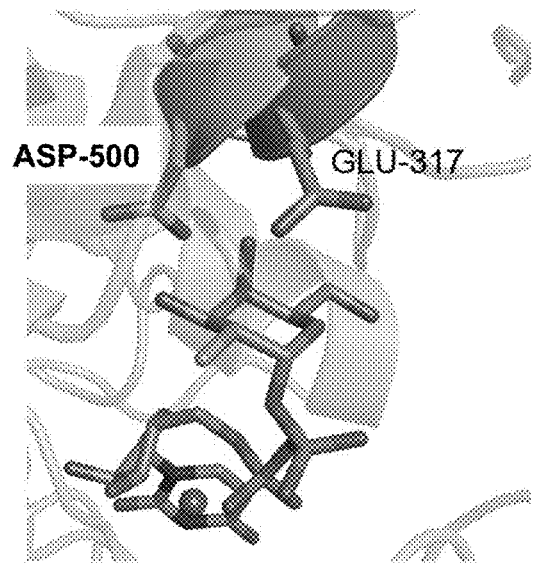
Figure 26C:
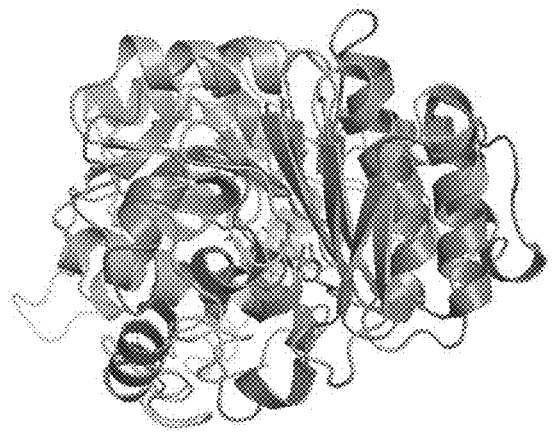
Figure 26D:
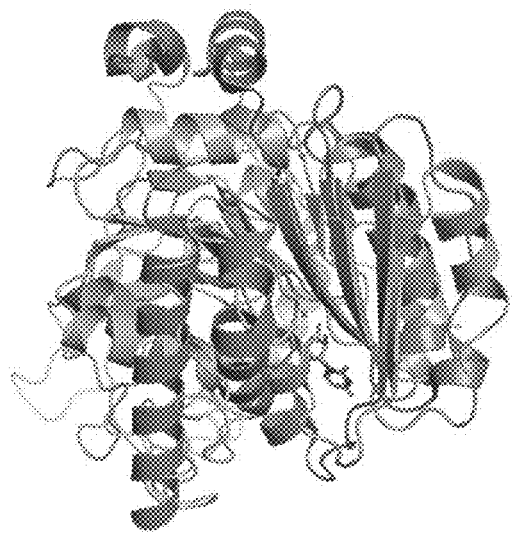

The formation of UDP-GlcNAc by reverse glycosylation of O6 using His$_6$-Δ80PmHS2 in the presence of UDP was further confirmed by a coupled enzyme assay (FIG. 24) inspired by Mehr et al. for indirectly detecting CMP-sialic acid formed in a reverse-sialyltransferase reaction.[41] To do this, an additional glycosyltransferase *Neisseria meningitidis* P1-3-N-acetylglucosaminyltransferase (NmLgtA)[44] and its acceptor 4-methylumberliferyl β-lactoside (LacβMU)[45] were added to the reaction of His$_6$-Δ80PmHS2 in the presence of O6 and UDP. As expected (Table 4), GlcNAcP1-3LacPMU formed by NmLgtA-catalyzed reaction was observed only in the reaction containing all components including NmLgtA, His$_6$-Δ80PmHS2, and UDP (Reaction 1 in Table 4) but not in the one lacking NmLgtA (Reaction 2 in Table 4), His$_6$-Δ80PmHS2 (Reaction 3 in Table 4), or UDP (Reaction 4 in Table 4).

Table 4 shows HPLC-based indirect detection of UDP-GlcNAc formed from the reverse glycosylation activity of His$_6$-Δ80PmHS2 from O6 and UDP by a coupled enzymatic assay with NmLgtA in the presence of LacβMU (Reaction 1). The production of other oligosaccharide by-products from the reversed glycosylation activities of His$_6$-Δ80PmHS2 was also shown. Negative controls include reactions lacking NmLgtA (Reaction 2), His$_6$-Δ80PmHS2 (Reaction 3), or UDP (Reaction 4). As shown below, GlcNAcβ1-3LacβMU, the expected product of NmLgtA-catalyzed glycosylation of LacβMU, was produced only in Reaction 1 containing all required components. The positive control reaction (Reaction 5) for NmLgtA (6 μM) with UDP-GlcNAc (1 mM) and LacβMU (1 mM) converted LacβMU completely to the glycosylated product GlcNAcβ1-3LacβMU.

TABLE 4

| Reaction | NmLgtA | His$_6$-Δ80PmHS2 | UDP | UDP-GlcNAc | LacβMU (%) | GlcNAcβ1-3LacβMU (%) | O2 (%) | O3 (%) |
|---|---|---|---|---|---|---|---|---|
| 1 | + | + | + | − | 90.3 ± 0.6 | 9.7 ± 0.6 | 9.3 ± 1.3 | 1.0 ± 0.1 |
| 2 | − | + | + | − | 100 | ND | 11.4 ± 1.6 | 0.7 ± 0.2 |
| 3 | + | − | + | − | 100 | ND | ND | ND |
| 4 | + | + | − | − | 100 | ND | ND | ND |
| 5 | + | − | − | + | ND | 100 | | |

| Reaction | O4 (%) | O5 (%) | O6 (%) | O7 (%) | O8 (%) | O9 (%) | O10 (%) | O11 (%) | O12 (%) |
|---|---|---|---|---|---|---|---|---|---|
| 1 | 16.2 ± 0.3 | 4.4 ± 0.3 | 36.2 ± 3.2 | 3.0 ± 0.5 | 20.4 ± 0.4 | 0.6 ± 0.1 | 7.3 ± 0.5 | ND | 1.7 ± 0.5 |
| 2 | 23.7 ± 7.3 | 5.1 ± 2.9 | 35.1 ± 4.3 | 1.2 ± 0.3 | 15.8 ± 1.5 | 0.5 ± 0.2 | 5.1 ± 0.3 | ND | 1.2 ± 0.1 |
| 3 | ND | ND | 100 | ND | ND | ND | ND | ND | ND |
| 4 | ND | ND | 100 | ND | ND | ND | ND | ND | ND |
| 5 | | | | | | | | | |

ND: not detected.

Example 5 Mutagenesis of His$_6$-Δ80PmHS2

Since reverse α1-4-GlcNAcT and β1-4-GlcAT activities of His$_6$-Δ80PmHS2 cause challenges in size-controlled enzymatic synthesis and purification of longer oligosaccharide products, mutagenesis studies of His$_6$-Δ80PmHS2 were planned to generate single-function glycosyltransferases by mutating the key catalytic base residues of the other glycosyltransferase domains. The previously reported strategy of generating single-functional glycosyltransferases of PmHS2[14] and PmHS1[23] by mutating the glycosyltransferase DXD motifs was not adopted due to the significant decrease of the stability of the PmHS2 mutants[14] which would adversely affect their application in synthesis. In the absence of known PmHS2 crystal structures, a Δ80PmHS2 I-TASSER[46-47] model was generated. The β1-4-GlcAT domain in Δ80PmHS2 I-TASSER model aligned well with the GalNAcT and GlcAT domains of *Escherichia coli* K4 chondroitin polymerase (EcKfoC) (PDB ID: 2Z86 and 2Z87)[48] (FIGS. 25A-25D), identifying D291 as a possible catalytic base. Similarly, a potential key catalytic residue (D569) in the Δ80PmHS2 α1-4-GlcNAcT domain was identified by aligning its I-TASSER model with the structures of *Neisseria meningitidis* lipopolysaccharyl-α1,4-galactosyltransferase (NmLgtC)[49-51] and bovine α1-3-galactosyltransferase (α3GalT)[52] (FIGS. 26A-26D).

Figure 27:
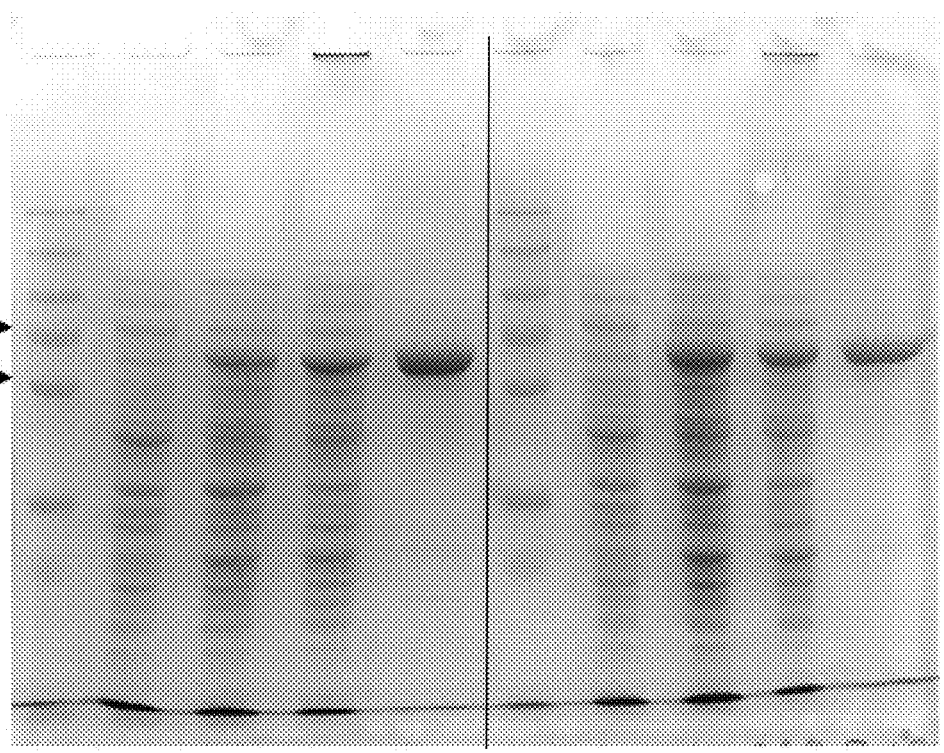
FIG. 27 SDS-PAGE analysis for the expression and purification of $His_6$-Δ80PmHS2 mutants D222N (left) and D500N (right). Lanes: BI, whole cell extract before induction; AI, whole cell extract after induction; L, lysate after induction; PP, $Ni^{2+}$-NTA column purified protein; M, protein markers (Bio-Rad precision Plus Protein Standards, 10-250 kDa).
Figure 28A:
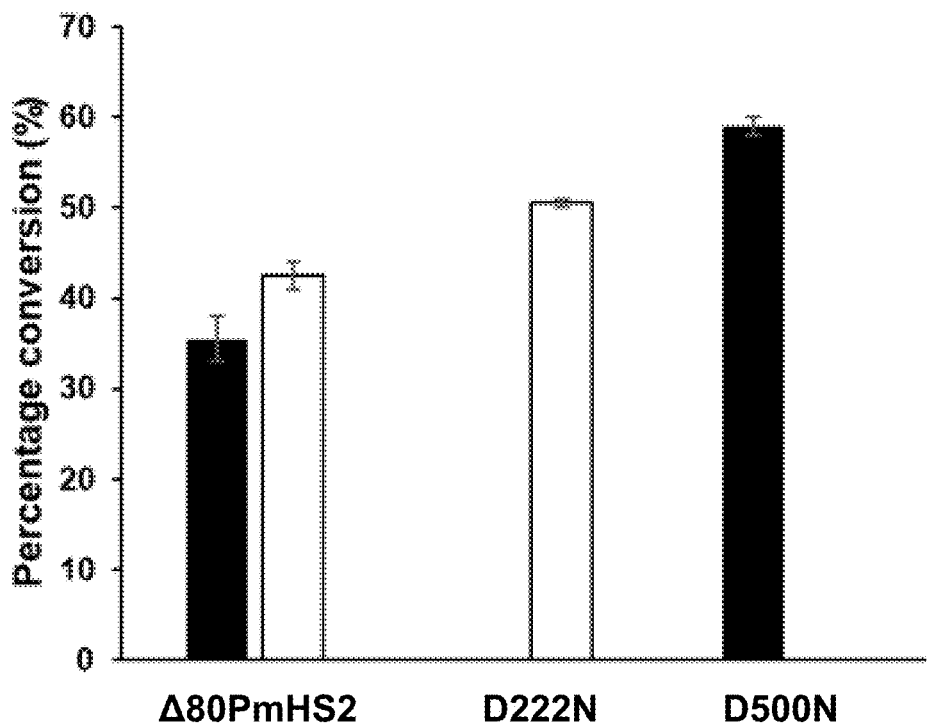
FIGS. 28A and 28B show relative α1-4-GlcNAcT (white columns) and β1-4-GlcAT (black columns) activities of $His_6$-Δ80PmHS2 and its D222N and D500N mutants when (A) the concentration of enzyme used was 0.68 uM and the reaction was carried out for 30 minutes or (B) the concentration of enzyme used was 30 µM and the reaction was carried out for 60 minutes. While the D291N mutant retained the α1-4-GlcNAcT activity of $His_6$-Δ80PmHS2 but completely removed its β1-4-GlcAT activity, the D500N mutant retained the β1-4-GlcAT activity of $His_6$-Δ80PmHS2 while decreased its α1-4-GlcNAcT activity by 548-fold.
Figure 28B:
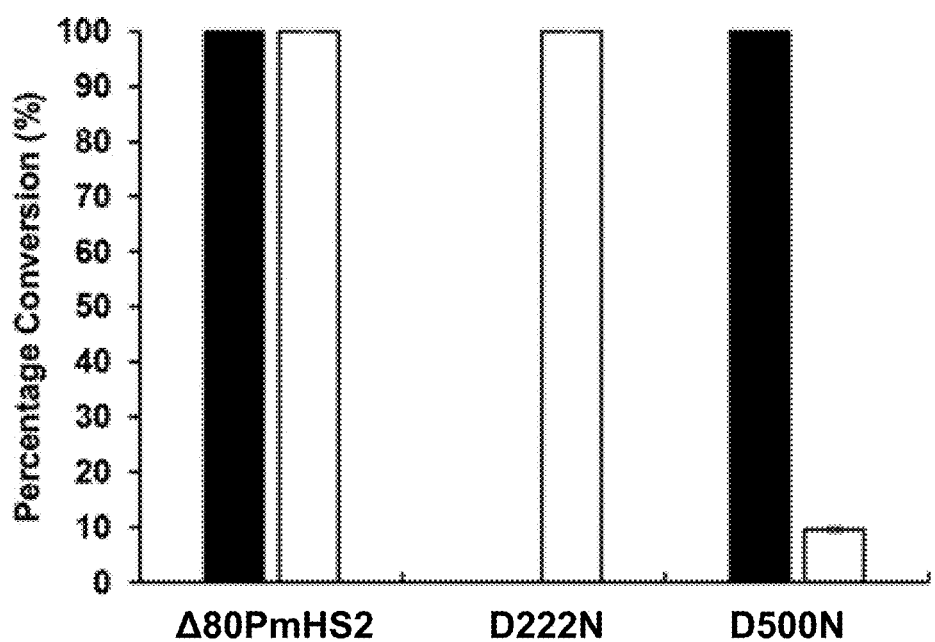
Figure 29A:
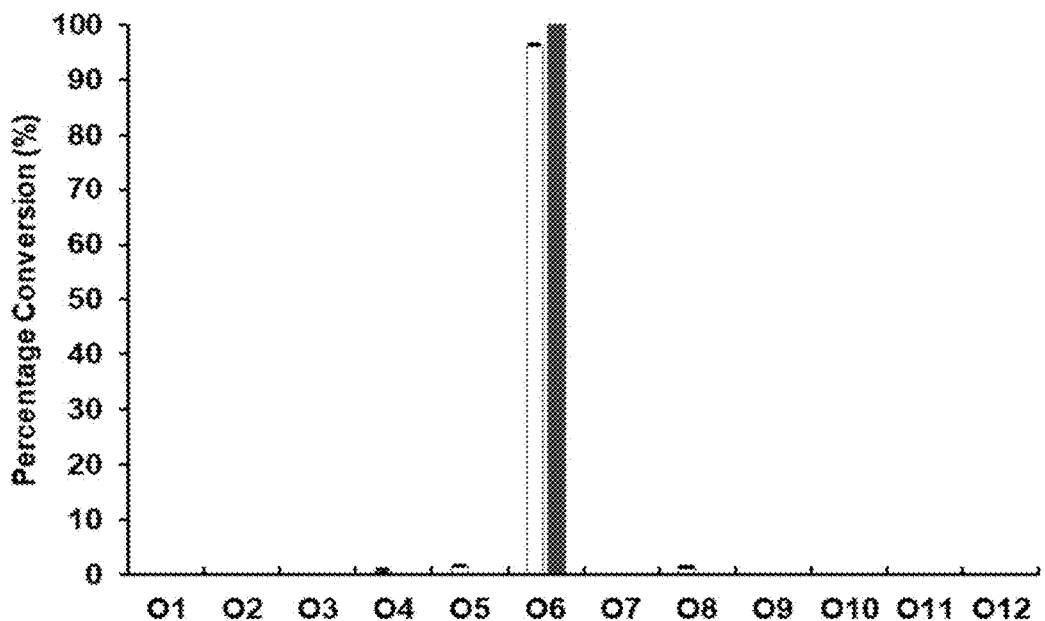
FIGS. 29A and 29B show reverse α1-4-GlcNAcT activity comparison of $His_6$-Δ80PmHS2 (white columns) and $His_6$-Δ80PmHS2-D500N (red columns) with hexasaccharide O6 (20 mM) in the presence of 30 mM (A); as well as reverse β1-4-GlcAT activity comparison of $His_6$-Δ80PmHS2 (white columns) and $His_6$-Δ80PmHS2-D222N (blue columns) with pentasaccharide O5 (20 mM) in the presence of 30 mM (B).
Figure 29B:
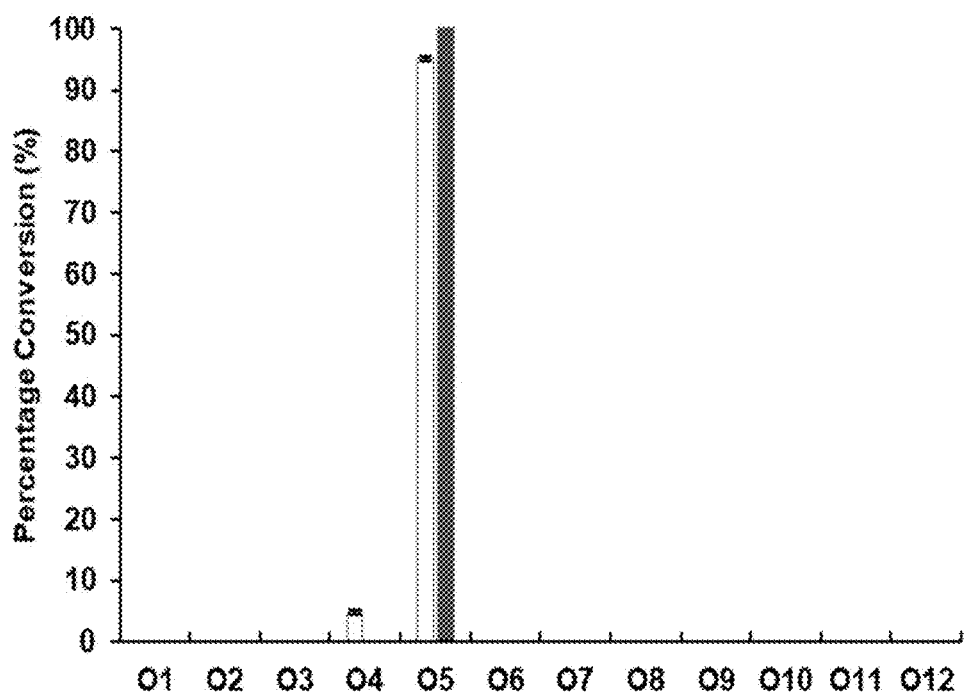

D222N and D500N (in SEQ ID NO:3) mutants of His$_6$-Δ80PmHS2 were generated (FIG. 27). Their expression levels (50-60 and 60-70 mg/L culture, respectively) were comparable to that of His$_6$-Δ80PmHS2 (60-80 mg/L culture). The D222N mutant retained the α1-4-GlcNAcT activity and lost the β1-4-GlcAT activity of His$_6$-Δ80PmHS2. In contrast, the D500N mutant retained His$_6$-Δ80PmHS2 β1-4-GlcAT activity while its α1-4-GlcNAcT activity decreased 548-fold (FIGS. 28A and 28B). The corresponding reverse glycosylation activities of His$_6$-Δ80PmHS2 also decreased significantly in the mutants. As shown in FIGS. 29A and 29B, under conditions mimicking synthetic reactions with 30 mM UDP (FIGS. 29A and 29B), no reverse glycosylation oligosaccharide products were observed for either mutants, demonstrating the efficiency of the mutants in blocking the cascade chain reactions shown in FIG. 21 and avoiding the generation of multiple oligosaccharide byproducts.

Figure 30:
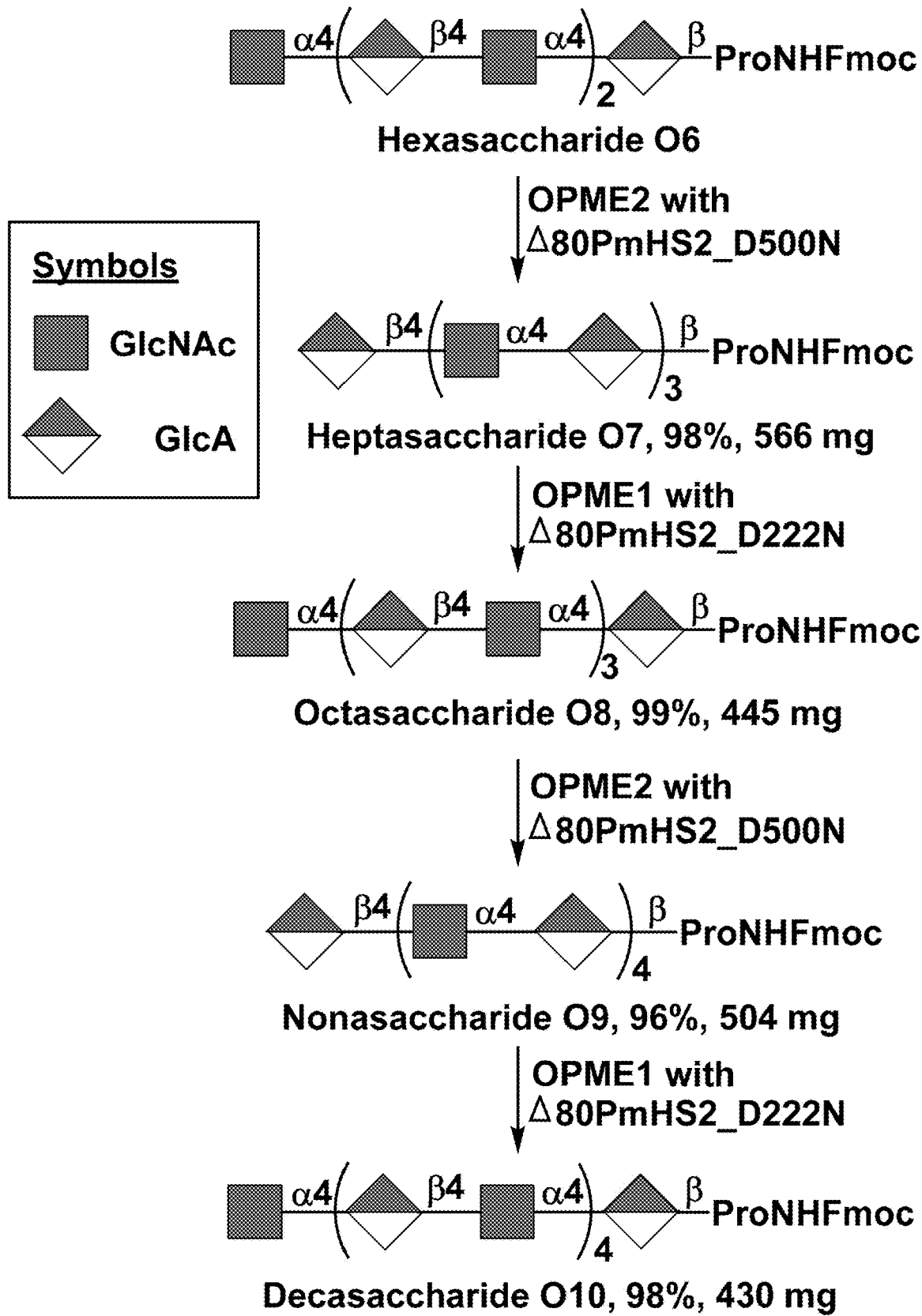
FIG. 30 shows sequential OPME synthesis of heparosan oligosaccharides O7-O10.

His$_6$-Δ80PmHS2 _D500N mutant was used as a single function β1-4-GlcAT (lacking both forward and reverse α1-4-GlcNAcT activities) in high-yield OPME synthesis (OPME2) (FIG. 30) of longer GlcA-terminated heparosan oligosaccharides including heptasaccharide O7 (566 mg, 98%) and nonasaccharide O9 (445 mg, 96%), respectively, from the corresponding GlcNAc-terminated His$_6$-Δ80PmHS2 _D500N oligosaccharide acceptors O6 and O8. His$_6$-Δ80PmHS2 _D222N mutant was used as a single function α1-4-GlcNAcT (lacking both forward and reverse β1-4-GlcAT activities) for high-yield OPME (OPME1) synthesis of longer GlcNAc-terminated oligosaccharides including octasaccharide O8 (504 mg, 99%) and decasaccharide O10 (430 mg, 98%), respectively, from the corresponding GlcA-terminated His$_6$-Δ80PmHS2 _D222N oligosaccharide acceptors O7 and O9. In these preparative-scale OPME reactions, unwanted oligosaccharide byproducts were not observed.

Various NMR experiments for O1-O10 including $^1$H and $^{13}$C NMR, HSQC, and HSQC-TOCSY (90 ms and 10 ms) enabled signal assignments and the observation of key correlations. HSQC spectra provided CH coupling information, and HSQC-TOCSY with 90 ms and 10 ms mixing times indicated independent coupling correlations of terminal and internal GlcA or GlcNAc residues. In the example of O3 containing two GlcA residues, the chemical shifts of the internal GlcA are more downfield for H3 (differ by 0.30 ppm), H4 (differ by 0.17 ppm), H5 (differ by 0.07 ppm), C1 (differ by 0.11 ppm), C2 (differ by 0.73 ppm), C3 (differ by 0.34 ppm), C4 (differ by 4.95 ppm), and C5 (differ by 3.18 ppm), but more upfield for H-1 (differ by 0.18 ppm) than that of the terminal GlcA.

In conclusion, N-terminal truncated His$_6$-Δ80PmHS2 with improved expression level and stability was shown to be an efficient catalyst for gram-scale sequential OPME synthesis of heparosan oligosaccharides up to hexasaccharide O6. Reverse glycosylation activities of His$_6$-Δ80PmHS2 were characterized and shown to be responsible for poor yields and complications in His$_6$-Δ80PmHS2-involved OPME synthesis of longer oligosaccharides. Key catalytic base residues for the β1-4-GlcAT and the α1-4-GlcNAcT activities of His$_6$-Δ80PmHS2 were identified. His$_6$-Δ80PmHS2 D500N and His$_6$-Δ80PmHS2 D222N mutants were generated as single functional β1-4-GlcAT and α1-4-GlcNAcT with significantly decreased reverse α1-4-GlcNAcT and reverse β1-4-GlcAT glycosyltransferase activities, respectively. They have been used as efficient catalysts for sequential OPME synthesis of longer length heparosan oligosaccharides (O7-O10). The study draws attention to the consideration of reverse glycosylation activities of glycosyltransferases including polysaccharide synthases when applying them in the synthesis of oligosaccharides and polysaccharides. The mutagenesis strategy has the potential to be extended to other multifunctional polysaccharide synthases with reverse glycosylation activities, especially those use sugar nucleotides containing the same nucleotide component, to generate catalysts with improved synthetic efficiency.

Example 6-[0085] Designing His$_6$-Δ80PmHS2 Mutants to Accommodate UDP-GlcNAc Derivatives This example describes the design of His$_6$-Δ80PmHS2 mutants to accommodate UDP-GlcNAc derivatives with modification at C-6 of GlcNAc, such as UDP-6-O-sulfo-GlcNAc (UDP-GlcNAc6OS) and/or UDP-6-N-sulfo-GlcNAc (UDP-GlcNAc6NS).

Residues (S496, G497, M498 in SEQ ID NO:3) of His$_6$-Δ80PmHS2 were chosen for mutagenesis to better accommodate C-6-modification at the GlcNAc in UDP-GlcNAc. The mutant deleting G497 was shown by high-resolution mass spectrometry to be able to catalyze the formation of GlcNAc6OSα1-4GlcAr3proNHFmoc from GlcAβproNHFmoc and UDP-GlcNAc6OS. It retains both β1-4GlcA-transferase and α1-4GlcNAc-transferase activities.

Example 7—Designing His$_6$-Δ80PmHS2 Mutants to Accommodate UDP-GlcA Derivatives This example describes the design of His$_6$-Δ80PmHS2 mutants to accommodate UDP-GlcA derivatives with modification at C-2 of GlcA such as UDP-GlcA2N3.

Residues of His$_6$-Δ80PmHS2 located at a β-strand (Y176 in SEQ ID NO:3), a loop (R195, L196, F198, I199, T200 in SEQ ID NO:3), and N248 in SEQ ID NO:3 near the C-2 position of GlcA in UDP-GlcA were chosen for mutagenesis. Mutants including Y176A, R195A, L196A, I199A, or T200A retained the β1-4GlcA-transferase activity.

Example 8—Designing His$_6$-Δ80PmHS2 Mutants to Accommodate UDP-GlcNAc Derivatives This example describes the design of His$_6$-Δ80PmHS2 mutants to accommodate UDP-GlcNAc derivatives with modification at C-3 of GlcNAc, such as UDP-3-O-sulfo-GlcNAc (UDP-GlcNAc3OS), UDP-3-azido-GlcNAc (UDP-GlcNAc3N3), and/or UDP-3-N-sulfo-GlcNAc (UDP-GlcNAc3NS).

Residues (K390, L473, T475, T477, and V478 in SEQ ID NO:3) of His$_6$-Δ80PmHS2 were chosen for mutagenesis to better accommodate C-3-modification at the GlcNAc in UDP-GlcNAc. T475A and T477A mutants retained α1-4-GlcNAc-transferase activity.

Example 9—DXD Motif Mutation

The triple mutant His$_6$-Δ80PmHS2 _D410N-D412N-D500N in SEQ ID NO:3 was generated. It was shown to reduce the forward and the reverse α1-4-GlcNAc-transferase activities while retained the β1-4GlcA-transferase activity of His$_6$-Δ80PmHS2.

Example 10 Experimental Methods

Materials and general methods. Chemicals were purchased and used without further purification. $^1$H NMR and $^{13}$C NMR spectra were recorded on 800 MHz Bruker Avance III spectrometers. High resolution electrospray ionization (ESI) mass spectra were obtained using Thermo Electron LTQ-Orbitrap Hybrid MS at the Mass Spectrometry Facility in the University of California, Davis. Silica gel 60 Å (230-400 mesh, Sorbent Technologies) was used for flash column chromatography. Discover® C18 cartridges were bought from Sigma. Thin-layer chromatography (TLC, Sorbent Technologies) was performed on silica gel plates using anisaldehyde sugar staining or 5% sulfuric acid in ethanol staining for detection. *Bifidobacterium longum* strain ATCC55813 N-acetylhexosamine-1-kinase (BL-NahK),[2] *Pasteurella multocida* N-acetylglucosamine uridyltransferase (PmGlmU),[3] *Pasteurella multocida* inorganic pyrophosphatase (PmPpA),[4] *Arabidopsis thaliana* glucuronokinase (AtGlcAK),[5] and *Bifidobacterium longum* UDP-sugar pyrophosphorylase (BLUSP)[6] were expressed and purified as described previously. GlcAβ2AA[7] was synthesized as reported previously.

Bacterial strains, plasmids, and materials. Nickel-nitrilotriacetic acid agarose ($Ni^{2+}$-NTA agarose) was purchased from Qiagen (Valencia, Calif., USA). Vector pET-15b was from EMD Millipore (Billerica, Mass., USA). Chemically competent DH5α and BL21 (DE3) cells were purchased from Invitrogen (Carlsbad, Calif., USA).

$His_6$-Δ80PmHS2 cloning. $His_6$-Δ80PmHS2 was cloned into pET15b vector using $His_6$-PmHS2 in pET-15b vector[7] as a template. Primers used were: forward 5'-ATCACAGCTTTGAAAAAATATATACCT ATAATCAAGCATTAGAAGC-3' (SEQ ID NO: 8) and reverse 5'-GATGATGATGATGGCTGCTACCC-3' (SEQ ID NO: 9). Polymerase chain reactions (PCRs) were performed in a reaction mixture of 50 μL containing the $His_6$-PmHS2-pET15b gene (72 ng), forward and reverse primers (1 μM each), 5×Phusion HF reaction buffer (10 μL), dNTP mixture (2 mM), and Phusion DNA polymerase (1 U, 0.5 μL). PCR procedure included an initial denaturing at 98° C. for 30 s, followed by 35 cycles of 10 s at 98° C., 20 s at 60° C., and 3 min at 72° C. For the final extension, the reaction was held at 72° C. for 10 min. The resulting PCR product was treated with DPN1 enzyme for 3 h at 37° C. The digested and purified PCR product was ligated, and transformed into Z-Competent™ *E. coli* DH5α cells. Positive plasmids (determined by DNA sequencing) were selected and transformed into *E. coli* BL21 (DE3) chemical competent cells.

Cloning of $His_6$-A80PmHS2 D291N and D569N mutants. $His_6$-Δ80PmHS2-pET-15b was used as a template for mutagenesis. The primers used for D291N mutant were: forward 5'-TAAAGGCTCAAACGATGAGTTTTTC-3' (SEQ ID NO: 10) and reverse 5'-GTCGTACAATTGAAGAAAC-3' (SEQ ID NO: 11). The primers used for D291N mutant were: forward 5'-TCAGGCATGGCTAATATCTATTTCTCTCTTGTG-3' (SEQ ID NO: 12) and reverse 5'-ATGGGTAAAGTCAGAAAGAGAAAATTGATTAAAGAGAC-3' (SEQ ID NO: 13). Polymerase chain reactions (PCRs) were performed in a reaction mixture of 50 μL including the $His_6$-Δ80PmHS2 pET-15b gene (10 ng), forward and reverse primers (0.5 μM each), 5×Phusion HF reaction buffer (10 μL), dNTP mixture (2 mM), and Phusion DNA polymerase (1 U, 0.5 μL). The PCR procedure included an initial denaturing at 98° C. for 30 s, followed by 30 cycles of 10 s at 98° C., 30 s at 63° C., and 4 min at 72° C. For the final extension, the reaction was held at 72° C. for 10 min. The linearized purified PCR product was subjected to Kinase-Ligase-Dpn1 (KLD) enzyme reactions followed by transformation into chemical competent *E. coli* DH5α cells. Positive plasmids were selected and transformed into *E. coli* BL21 (DE3) chemical competent cells.

Protein expression and purification. The plasmid-bearing *E. coli* BL21(DE3) cells were cultured in 1 L of LB-rich media (10 g/L tryptone, 5 g/L yeast extract and 10 g/L NaCl) supplemented with ampicillin (100 μg/mL). Expression of the target protein was achieved by inducing the *E. coli* culture with 0.1 mM of isopropyl-1-thio-β-D-galactopyranoside (IPTG) when $OD_{600\,nm}$ reached 0.8-1.0, followed by incubating at 20° C. for 20 h with shaking at 250 rpm in a C25KC incubator shaker (New Brunswick Scientific, Edison, N.J.). Histidine-tagged target proteins were purified from cell lysate. To obtain the cell lysate, cell pellet harvested by centrifugation at 2,795 g for 50 min was resuspended (25 mL/L cell culture) in lysis buffer (Tris-HCl, 100 mM, pH 8.0 with 0.1% Triton X-100). Sonication protocol was 2 s (sonication)/3 s (rest) for a total of 6 min on ice. Lysed cells were centrifuged at 5,000 g for 50 min and the supernatant (lysate) was collected. Purification of histidine-tagged proteins from the lysate was achieved using a Ni'-resin column. The column was pre-equilibrated with 10 column volumes of binding buffer (5 mM imidazole, 0.5 M NaCl, 50 mM Tris-HCl, pH 7.5). The lysate was then loaded, and the column was washed with 10 column volumes of binding buffer and 10 column volumes of washing buffer (16 mM imidazole, 0.5 M NaCl, 50 mM Tris-HCl, pH 7.5). The target protein was eluted with Tris-HCl buffer (50 mM, pH 7.5) containing imidazole (200 mM) and NaCl (0.5 M). The fractions containing the purified enzymes were collected, and stored at 4° C.

Relative activity comparison of $His_6$-PmHS2 and $His_6$-Δ80PmHS2 using GlcAβProNHFmoc (O1) or GlcNAcαProNHFmoc as an acceptor to form the corresponding disaccharide product GlcNAcα1-4GlcAβProNHFmoc or GlcAβ1-4GlcNAcαProNHFmoc. Reactions were carried out in triplicate at 37° C. for 30 min in a reaction mixture (20 μL) containing MES buffer (100 mM, pH 6.5), $MnCl_2$ (10 mM), a donor substrate (UDP-GlcA or UDP-GlcNAc, 1 mM), a monosaccharide acceptor (GlcAβProNHFmoc O1 or GlcNAcαProNHFmoc, 1 mM, see below for their synthesis), and enzyme $His_6$-PmHS2 or $His_6$-Δ80PmHS2 (0.06 or 1.5 mg/mL). Reactions were stopped by heating reaction mixtures at 70° C. for 10 min, followed by incubation on ice for 30 min and centrifugation at 11,337 g for 15 min. Chromatographic separation and detection were achieved with an Infinity 1290 II HPLC equipped with 1260 Infinity II Diode Array Detector WR (monitored at 254 nm, Agilent Technologies, CA) with a ZORBAX Eclipse Plus C18 Rapid Resolution HD column (1.8 μm particle, 2.1×50 mm, Agilent Technologies, CA) and an isocratic flow (0.7 mL/min) of a mixed solvent (27% acetonitrile/73% of water with 0.1% TFA).

Kinetics studies of $His_6$-PmHS2 and $His_6$-Δ80PmHS2 using GlcAβ2AA as the acceptor substrate. All kinetics reactions were performed in triplicates at 37° C. for 30 min in MES buffer (200 mM, pH 6.5) containing UDP-GlcNAc (1 mM), $MnCl_2$ (10 mM), GlcAβ2AA (0, 0.2, 0.5, 1.0, 2.0, 4.0, 100, 15.0 mM for $His_6$-PmHS2; and 0, 0.2, 0.5, 1.0, 2.0, 4.0, 8.0, 10.0, 15.0 mM for $His_6$-Δ80PmHS2), and enzyme $His_6$-PmHS2 (175 nM) or $His_6$-Δ80PmHS2 (164 nM). Reactions were stopped by heating reaction mixtures at 70° C. for 10 min, followed by incubation on ice for 30 min and centrifugation at 11,337 g for 15 min. Reactions were stopped and assayed similarly to that described above for relative activity comparison studies using two different monosaccharide acceptors except for an isocratic flow (0.5 mL/min) of a mixed solvent (19% acetonitrile/81% of water with 0.1% TFA) was used for UHPLC assays. Apparent kinetic parameters for reactions with a fixed concentration (1 mM) of UDP-GlcNAc and varying GlcAβ2AA concentrations were determined in GraFit 5.0 by non-linear regression. Data for repeated experiments were obtained.

Thermostability assays. $His_6$-PmHS2 (0.6 μM) or $His_6$-Δ80PmHS2 (0.5 μM) was incubated at different temperatures ranging from 25° C. to 50° C. for 30 min followed by incubation on ice for 10 min before the samples were centrifuged and the supernatants were used for activity assays at 37° C. for 30 min in duplicate in a reaction mixture containing the enzyme, UDP-GlcNAc (1 mM), GlcAβ2AA (1 mM), $MnCl_2$ (10 mM) in MES buffer (200 mM, pH 6.5). UHPLC detection was carried out similarly as described above for kinetics studies.

Survival of lyophilization assays. Purified $His_6$-Δ80PmHS2 samples were dialyzed against Tris-HCl buffer (20 mM, pH 7.5) at 4° C. and lyophilized. The resulting powders were stored at −80° C. for 3 days. For activity assays, the dried powder was dissolved in water. The activity assays were carried out in duplicate at 37° C. for 10 min in a total volume of 20 μL containing MES buffer (100 mM, pH 6.5), UDP-GlcNAc (1 mM), GlcAβProNHFmoc O1 (1 mM), $MnCl_2$ (10 mM), and $His_6$-Δ80PmHS2 (3 μg). Chromatographic separation and detection were achieved similarly as described above for the kinetics studies except that an isocratic flow (0.3 mL/min) of a mixed solvent (32% acetonitrile/68% water with 0.1% TFA) was used for elution.

pH Profile assays. The assays were performed in duplicate in a reaction mixture (20 μL) containing a buffer (200 mM) with a pH in the range of 3.0-11.0, UDP-GlcNAc (1 mM), GlcAβ2AA (1 mM), $MnCl_2$ (10 mM), and $His_6$-Δ80PmHS2 (0.5 μg). Buffers used were: citrate, pH 3.0-4.0; ammonium acetate, pH 4.5; MES, pH 5.0-6.5; Tris-HCl, pH 7.0-9.0; N-cyclohexyl-3-aminopropanesulfonic acid (CAPS), pH 9.5-11.0. Reactions were allowed to proceed for 30 min at 37° C. and were stopped by adding 20 μL of cold methanol to each reaction mixture. Chromatographic separation and detection were achieved similarly to that described above for kinetics studies.

Donor substrate specificity assays. All reactions were performed in duplicate in a reaction mixture (20 μL) containing MES buffer (200 mM, pH 6.5), a UDP-GlcNAc derivative (1 mM), GlcAβ2AA (1 mM), $MnCl_2$ (10 mM), and an enzyme (16 μM) at 37° C. for 1 h and 13 h, respectively. Chromatographic separation and detection were achieved similarly to that described above for kinetics studies.

The effect of UDP concentration on the reverse glycosylation activities of $His_6$-PmHS2 and $His_6$-Δ80PmHS2. Reactions were carried out in triplicate at 37° C. for 15 h in reaction mixtures (20 μL) containing MES buffer (100 mM, pH 6.5), $MnCl_2$ (10 mM), O6 (1 mM), UDP with a concentration varying from 0, 1, 5, and 10 mM, and enzyme ($His_6$-PmHS2 or $His_6$-Δ80PmHS2, 15 μM). Reactions were stopped by heating reaction mixtures at 70° C. for 10 min followed by incubation on ice for 30 min, and centrifugation at 11,337 g for 15 min. Supernatants were analyzed using an Infinity 1290 II HPLC equipped with 1260 Infinity II Diode Array Detector WR (monitored at 254 nm, Agilent Technologies, CA). An AdvanceBio Glycan Mapping column (1.8 μm particle, 2.1×150 mm, Agilent Technologies, CA) was used with a gradient (13 min) of 0.5 mL/min for 90% to 70% acetonitrile and a solution of water with 0.1% TFA for analysis.

Coupled-enzyme reverse glycosylation assay. Reactions (20 μL) were carried out in triplicate at 37° C. for 15 h in MES buffer (100 mM, pH 6.5) containing $MnCl_2$ (10 mM), O6 (1 mM), UDP (10 mM), Lac MU (1 mM), NmLgtA (2 μM), and $His_6$-Δ80PmHS2 (15 μM). Negative control reactions without NmLgtA, $His_6$-Δ80PmHS2, or UDP and a positive control reaction for NmLgtA (6 μM) with UDP-GlcNAc (1 mM) and Lac MU (1 mM) were carried out at the same time. Reactions were stopped by heating reaction mixtures at 70° C. for 10 min followed by incubation on ice for 30 min and centrifuged at 11,337 g for 15 min. Supernatants were analyzed similarly to that described above for the effect of UDP concentration on reverse glycosylation activity of $His_6$-Δ80PmHS2. Fmoc-containing compounds (O6 and oligosaccharides formed by reverse glycosylation reaction of $His_6$-Δ80PmHS2) and MU-containing compounds were monitored at 254 nm and 315 nm, respectively.

Time-course reverse glycosylation assays. Reactions were carried out in duplicate at 37° C. for 15 h in reaction mixtures (120 μL) containing MES buffer (100 mM, pH 6.5), $MnCl_2$ (10 mM), O6 or O5 (1 mM), UDP (10 mM), and $His_6$-Δ80 PmHS2 (15 μM). An aliquot of reaction mixture (20 μL) was withdrawn at different reaction times (30 min, 1 h, 2 h, 6 h, and 13 h, respectively), heated at 70° C. for 10 min, incubated on ice for 30 min, centrifuged at 11,337 g for 15 min, and the supernatants were analyzed similarly to that described above for the effect of UDP concentration on reverse glycosylation activity of Δ80PmHS2 except that a 9 min gradient was used for HPLC analysis.

α1-4-GlcNAcT activity comparison of $His_6$-Δ80PmHS2 and its D222N and D500N mutants. Reactions were carried out in duplicate at 37° C. for 30 min (when 0.68 μM enzyme was used) or 1 h (when 30 μM enzyme was used) in reaction mixtures (20 μL) containing MES buffer (100 mM, pH 6.5), $MnCl_2$ (10 mM), GlcAβProNHFmoc O1 (1 mM), UDP-GlcNAc (1 mM), and an enzyme ($His_6$-Δ80PmHS2, $His_6$-Δ80PmHS2 _D222N, $His_6$-Δ80PmHS2 _D500N, 0.68 μM or 30 μM). Reactions were stopped by heating reaction mixture at 70° C. for 10 min, followed by incubation on ice for 30 min and centrifugation at 11,337 g for 15 min. Supernatants were analyzed similarly to that described above for survival of lyophilization assays.

β1-4-GlcAT activity comparisons of $His_6$-Δ80PmHS2 and its D222N and D500N mutants. Reactions were carried out in duplicate at 37° C. for 30 min (when 0.68 μM enzyme was used) or 1 h (when 30 μM enzyme was used) in a reaction mixture (20 μL) containing MES buffer (100 mM, pH 6.5), $MnCl_2$ (10 mM), disaccharide O2 (1 mM), UDP-GlcA (1 mM), and an enzyme ($His_6$-Δ80PmHS2, $His_6$-Δ80PmHS2 _D222N, or $His_6$-Δ80PmHS2 D500N, 0.68 μM or 30 μM). Reactions were stopped by heating reaction mixtures at 70° C. for 10 min, followed by incubation on ice for 30 min and centrifugation at 11,337 g for 15 min. Supernatants were analyzed similarly to that described above for the coupled-enzyme reverse glycosylation assay.

Reverse glycosylation assay comparison for $His_6$-Δ80PmHS2 and its D222N or D500N mutants mimicking synthetic conditions (with 30 mM UDP) and in the presence of a higher concentration of UDP (100 mM). Reactions were carried out in triplicate at 37° C. for 15 h in a reaction mixture (20 μL) containing Tris-HCl buffer (100 mM, pH 7.5), $MgCl_2$ (20 mM), hexasaccharide O6 or pentasaccharide O5 (20 mM), UDP (30 mM or 100 mM), and an enzyme ($His_6$-Δ80PmHS2 _D291N, $His_6$-Δ80PmHS2 _D569N, or $His_6$-Δ80PmHS2, 4.5 μM). Reactions were stopped by heating reaction mixtures at 70° C. for 10 min, followed by incubation on ice for 30 min and centrifugation at 11,337 g for 15 min. Supernatants were analyzed similarly to that described above for time-course reverse glycosylation assays.

Synthesis of GlcAβProNHFmoc (O1).

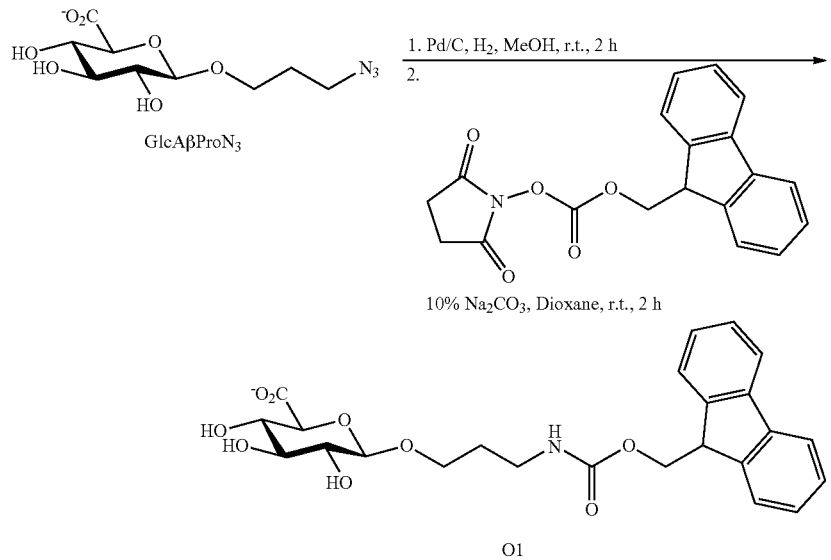

1-O-(3-Azidoopropyl)-β-D-glucopyranuronic acid (GlcAβProN3)[7] (1.05 g, 4.58 mmol) was dissolved in MeOH (100 mL) and Pd/C (200 mg) was added. The mixture was stirred at room temperature under an $H_2$ atmosphere for 2 h, then filtered and concentrated. The obtained amine residue was dissolved in aqueous 10% $Na_2CO_3$ (40 mL) and dioxane (30 mL). Fmoc-OSu (1 eq., 1.7 g, 5.04 mmol) was dissolved in dioxane (30 mL) and added dropwisely to the mixture at 0° C. The resulting mixture was stirred at room temperature for 2 h before it was concentrated. The resulting residue was purified by silica gel chromatography (EtOAc:MeOH:$H_2O$=8:2:1, by volume) to produce O1 as a white solid (1.88 g, 83%). $^1$H NMR (800 MHz, MeOD) δ 7.70 (d, J=7.2 Hz, 2H), 7.57 (dd, J=7.2 Hz, 1H), 7.56 (dd, J=7.2 Hz, 1H), 7.29 (t, J=7.2 Hz, 2H), 7.22 (t, J=7.2 Hz, 1H), 7.21 (t, J=7.2 Hz, 1H), 4.24 (d, J=7.2 Hz, 2H, CH—C$\underline{H}_2$O$_{Fmoc}$), 4.17 (t, J=7.2 Hz, 1H, H$_{GlcA}$-1), 4.11 (t, J=7.2 Hz, 1H, C$\underline{H}$—CH$_2$O$_{Fmoc}$), 3.93-3.90 (m, 1H, —OC$\underline{H}_2$—CH$_2$—CH$_2$N—), 3.50-3.47 (m, 1H, —OC$\underline{H}_2$—CH$_2$—CH$_2$N—), 3.48 (d, J=8.8 Hz, 1H, H$_{GlcA}$-5), 3.34 (t, J=8.8 Hz, 1H, H$_{GlcA}$-4), 3.32 (t, J=8.8 Hz, 1H, H$_{GlcA}$-3), 3.20-3.11 (m, 3H, —OCH$_2$—CH$_2$—C$\underline{H}_2$N—, H$_{GlcA}$-2), 1.71-1.66 (m, 2H, —OCH$_2$—C$\underline{H}_2$—CH$_2$N—); $^{13}$C NMR (200 MHz, MeOD) δ 175.45, 157.52, 143.91, 143.86, 141.11, 141.10, 127.26, 126.67, 124.76, 124.72, 119.51, 119.40, 102.77 (C$_{GlcA}$-1), 76.37(C$_{GlcA}$-3), 74.36(C$_{GlcA}$-5), 73.44(C$_{GlcA}$-2), 72.22(C$_{GlcA}$-4), 66.39 (—OC$\underline{H}_2$—CH$_2$—CH$_2$N—), 66.11 (CH—$\underline{C}$H$_2$O$_{Fmoc}$), 47.10 ($\underline{C}$H—CH$_2$O$_{Fmoc}$), 36.96 (—OCH$_2$—CH$_2$—$\underline{C}$H$_2$N—), 29.29 (—OCH$_2$—$\underline{C}$H$_2$—CH$_2$N—). HRMS (ESI) m/z: [M−H]$^−$ calculated for $C_{24}H_{26}NO_9$ 472.1613; found 472.1608.

Synthesis of GlcNAcαProNHFmoc.

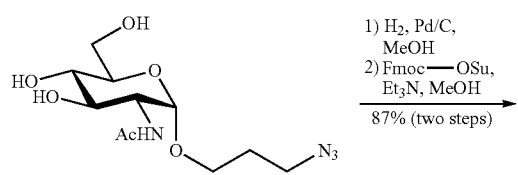

GlcNAcαProN$_3$[4] (110 mg, 0.36 mmol) was dissolved in MeOH (7 mL) and Pd/C (15 mg) was added. The mixture was stirred at room temperature under an $H_2$ atmosphere for overnight. The reaction mixture was then filtered and concentrated. The obtained amine residue was dissolved in MeOH (10 mL). Et$_3$N (101 μL, 0.72 mmol) and Fmoc-OSu (182 mg, 0.54 mmol) was added and the resulting mixture was stirred at room temperature for overnight. After concentration, the resulting residue was purified by silica gel chromatography (EtOAc:MeOH=4:1, by volume) to produce the product GlcNAcαProNHFmoc as a white solid (157 mg, 87%). $^1$HNMR (800 MHz, MeOD) δ 7.67 (d, J=7.2 Hz, 2H), 7.52 (dd, J=7.2 Hz, 2H), 7.27 (t, J=7.2 Hz, 2H), 7.19 (t, J=7.2 Hz, 2H), 4.66 (d, J=3.2 Hz, 1H, H$_{GlcNAc}$-1), 4.25 (d, J=7.2 Hz, 2H, CH—C$\underline{H}_2$O$_{F\_moc}$), 4.11 (t, J=7.2 Hz, 1H, C$\underline{H}$—CH$_2$O$_{Fmoc}$), 3.82 (dd, J=4.0 and 11.2 Hz, 1H), 3.74 (dd, J=2.4 and 12.0 Hz, 1H), 3.65-3.48 (m, 4H), 3.31-3.08 (m, 4H), 1.90 (s, 3H); 1.68-1.65 (m, 2H); $^{13}$C NMR (200 MHz, MeOD) δ 173.60, 172.46, 157.59, 143.96, 143.90, 141.19, 127.41, 126.77, 124.76, 124.75, 119.58, 97.16, 72.48, 71.65, 70.97, 66.18, 64.44, 61.36, 47.11, 37.25, 29.33, 24.93, 21.34. HRMS (ESI) m/z: [M+H]$^+$ calculated for $C_{26}H_{33}N_2O_8$ 501.2237; found 501.2242.

General procedures for adding GlcNAc via the one-pot four-enzyme GlcNAc-glycosylation system. Reactions were carried out in an incubator shaker at 30° C. for 1-2 days with agitation at 100 rpm. Reaction mixtures contain Tris-HCl buffer (100 mM, pH 7.5), MgCl$_2$ (20 mM), an acceptor substrate (O1, O3, O5, O7, or O9, 20 mM), D-GlcNAc (1.5 equiv.), ATP (1.5 equiv.), UTP (1.5 equiv.), BLNahK (0.25 mg/mL), PmGlmU (0.20 mg/mL), PmPpA (0.20 mg/mL), and a glycosyltransferase (0.30 mg/mL) selected from His$_6$-

Δ80PmHS2 (for O1, O3, or O5) and His$_6$-Δ80PmHS2_D222N (for O7 or O9). The product formation was monitored by mass spectrometry. When an optimal yield was achieved, the reaction was quenched by adding a same volume of ice-cold ethanol followed by incubating the mixture at 4° C. for 30 min. The mixture was centrifuged and the precipitates were removed. The supernatant was concentrated and the residue was purified using an ODS-SM column (51 g, 50 μm, 120 Å, Yamazen) on a CombiFlash® Rf 200i system. After loading the sample, the column was washed with water for 5 min and the product was eluted with a gradient (25 min) of 0-100% acetonitrile in water (v/v). The glycan-containing fractions were analyzed by TLC and MS and the fractions containing pure products were collected and lyophilized to obtain the desired product as a white powder.

General procedures for adding GlcA via the one-pot four-enzyme GlcA-glycosylation system. Reactions were carried out in an incubator shaker at 30° C. for 24 h with agitation at 100 rpm. Reaction mixtures contain Tris-HCl buffer (100 mM, pH 8.0), MgCl$_2$ (20 mM), an acceptor substrate (O2, O4, O6, or O8, 20 mM), D-GlcA (1.4 equiv.), ATP (1.5 equiv.), UTP (1.5 equiv.), AtGlcAK (0.5 mg/mL), BLUSP (0.6 mg/mL), PmPpA (0.20 mg/mL), and a glycosyltransferase (0.25 mg/mL) selected from His$_6$-Δ80PmHS2 (for O2, or O4) and His$_6$-Δ80PmHS2 D500N (for O6 or O8). The product formation was monitored by mass spectrometry. When an optimal yield was achieved, the reaction was quenched by adding a same volume of ice-cold ethanol followed by incubating the mixture at 4° C. for 30 min. The mixture was centrifuged and the precipitates were removed. The supernatant was concentrated and the residue was purified using an ODS-SM column (51 g, 50 μm, 120 Å, Yamazen) on a CombiFlash® Rf 200i system. After loading the sample, the column was washed with water for 5 min and the product was eluted with a gradient (25 min) of 0-100% acetonitrile in water (v/v). The glycan-containing fractions were analyzed by TLC and MS and the fractions containing pure products were collected and lyophilized to obtain the desired product as a white powder.

GlcNAcα1-4GlcAβProNHFmoc (O2). 2.12 g, 96%. $^1$H NMR (800 MHz, MeOD) δ 7.68 (d, J=7.2 Hz, 2H), 7.54 (dd, J=8.0 Hz, 2H), 7.28 (t, J=7.2 Hz, 2H), 7.21 (t, J=7.2 Hz, 2H), 5.29 (d, J=4.0 Hz, 1H, H$_{GlcNAc}$-1), 4.24 (d, J=7.2 Hz, 2H, CH—CH$_2$O$_{-Fmoc}$), 4.16 (d, J=7.2 Hz, 1H, H$_{GlcA}$-1), 4.09 (t, J=7.2 Hz, 1H, CH—CH$_2$O$_{-Fmoc}$), 3.81-3.78 (m, 3H, H$_{GlcNAc}$-2, H$_{GlcNAc}$-6a, —OCH$_2$—CH$_2$—CH$_2$N—), 3.69 (t, J=8.0 Hz, 1H, H$_{GlcA}$-4), 3.67-3.65 (m, 1H, H$_{GlcNAc}$-5), 3.61 (d, J=9.6 Hz, 1H, H$_{GlcA}$-5), 3.58-3.54 (m, 2H, H$_{GlcNAc}$-6b, H$_{GlcNAc}$-3), 3.51 (t, J=8.0 Hz, 1H, H$_{GlcA}$-3), 3.45-3.42 (m, 1H, —OCH$_2$—CH$_2$—CH$_2$N—), 3.19-3.08 (m, 4H, H$_{GlcA}$-2, H$_{GlcNAc}$-4, —OCH$_2$—CH$_2$—CH$_2$N—), 1.91 (s, 3H), 1.68-1.64 (m, 2H, —OCH$_2$-CH$_2$—CH$_2$N—); $^{13}$C NMR (200 MHz, MeOD) δ 174.93, 172.30, 157.46, 143.87, 143.85, 141.11, 127.28, 126.67, 124.73, 124.69, 119.43, 102.83 (C$_{GlcA}$-1), 96.97 (C$_{GlcNAc}$-1), 77.13 (C$_{GlcA}$-5), 76.61 (C$_{GlcA}$-3), 76.52 (C$_{GlcA}$-4), 73.93 (C$_{GlcA}$-2), 72.37 (C$_{GlcNAc}$-5), 71.60 (C$_{GlcNAc}$-3), 71.18 (C$_{GlcNAc}$-4), 66.51 (—OCH$_2$—CH$_2$—CH$_2$N—), 66.10 (CH—CH$_2$O$_{-Fmoc}$), 61.41 (C$_{GlcNAc}$-6), 54.04 (C$_{GlcNAc}$-2), 47.03 (CH—CH$_2$O$_{-Fmoc}$), 37.10 (—OCH$_2$—CH$_2$—CH$_2$N—), 29.33 (—OCH$_2$—CH$_2$—CH$_2$N—), 21.39 (CH$_3$). HRMS (ESI) m/z: [M–H]$^-$ calculated for C$_{32}$H$_{39}$N$_2$O$_{14}$ 675.2407; found 675.2411.

GlcAβ1-4GlcNAcα1-4GlcAβProNHFmoc (O3). 1.94 g, 99%. $^1$H NMR (800 MHz, MeOD) δ 7.74 (d, J=7.2 Hz, 2H), 7.60 (d, J=7.2 Hz, 2H), 7.34 (t, J=7.2 Hz, 2H), 7.27 (t, J=7.2 Hz, 2H), 5.35 (d, J=4.0 Hz, 1H, H'-1), 4.40 (d, J=8.0 Hz, 1H, H"-1), 4.30 (d, J=7.2 Hz, 2H, CH—CH$_2$O$_{-Fmoc}$), 4.22 (d, J=7.2 Hz, 1H, H-1), 4.15 (t, J=7.2 Hz, 1H, CH—CH$_2$O$_{-Fmoc}$), 3.90 (dd, J=4.0 and 12.0 Hz, 1H, H'-2), 3.87-3.83 (m, 4H, H'-5, H'-6a, H'-6b, —OCH$_2$—CH$_2$—CH$_2$N—), 3.74 (t, J=9.6 Hz, 2H, H-3, H'-3), 3.66 (d, J=9.6 Hz, 1H, H-5), 3.61 (t, J=9.6 Hz, 1H, H'-4), 3.59 (d, J=9.6 Hz, 1H, H"-5), 3.57 (t, J=8.8 Hz, 1H, H-4), 3.51-3.48 (m, 1H, —OCH$_2$—CH$_2$—CH$_2$N—), 3.41 (t, J=8.8 Hz, 1H, H"-3), 3.39 (t, J=8.8 Hz, 1H, H"-4), 3.26-3.14 (m, 4H, H"-2, H-2, —OCH$_2$—CH$_2$—CH$_2$N—), 1.98 (s, 3H), 1.74-1.70 (m, 2H, —OCH$_2$—CH$_2$—CH$_2$N—); $^{13}$C NMR (200 MHz, MeOD) δ 175.09, 174.67, 172.45, 157.46, 143.87, 143.85, 141.12, 141.11, 127.27, 126.67, 124.73, 124.69, 119.42, 102.82 (C-1), 102.72 (C"-1), 96.95 (C'-1), 77.66 (C'-4), 77.05 (C-5), 76.89 (C-4), 76.21 (C-3), 75.86 (C"-3), 73.94 (C-2), 73.87 (C"-5), 73.22 (C"-2), 71.94 (C"-4), 71.18 (C'-5), 69.87 (C'-3), 66.41 (—OCH$_2$—CH$_2$—CH$_2$N—), 66.09 (CH—CH$_2$O$_{-Fmoc}$), 59.66 (C'-6), 53.91 (C'-2), 47.03 (CH—CH$_2$O$_{-Fmoc}$), 37.08 (—OCH$_2$—CH$_2$—CH$_2$N—), 29.31 (—OCH$_2$—CH$_2$—CH$_2$N—), 21.41 (CH$_3$). HRMS (ESI) m/z: [M–2H]$^{2-}$ calculated for C$_{38}$H$_{46}$N$_2$O$_{20}$ 425.1327; found 425.1321; [M–H]$^-$ calculated for C$_{38}$H$_{47}$N$_2$O$_{20}$ 851.2721; found 851.2711.

GlcNAcα1-4GlcAβ1-4GlcNAcα1-4GlcAβProNHFmoc (O4). 1.87 g, 98%. $^1$H NMR (800 MHz, MeOD) δ 7.69 (d, J=7.2 Hz, 2H), 7.55 (dd, J=7.2 Hz, 2H), 7.29 (t, J=7.2 Hz, 2H), 7.21 (t, J=7.2 Hz, 2H), 5.35 (d, J=4.0 Hz, 1H, H'''-1), 5.31 (d, J=4.0 Hz, 1H, H'-1), 4.33 (d, J=8.0 Hz, 1H, H"-1), 4.24 (d, J=7.2 Hz, 2H, CH—CH$_2$O$_{-Fmoc}$), 4.15 (d, J=8.0 Hz, 1H, H-1), 4.10 (t, J=7.2 Hz, 1H, CH—CH$_2$O$_{-Fmoc}$), 3.82-3.74 (m, 6H, H'-2, H'''-2, H'-6a, H'-6b, H"-6a, —OCH$_2$—CH$_2$—CH$_2$N—), 3.72-3.62 (m, 5H, H'-5, H'''-5, H-3, H'-3, H"-4), 3.60-3.53 (m, 5H, H-5, H"-5, H"-2, H"-3, H"-6b), 3.50-3.46 (m, 2H, H'-4, H-4), 3.44-3.41 (m, 1H, —OCH$_2$—CH$_2$—CH$_2$N—), 3.22 (t, J=8.8 Hz, 1H, H"-3), 3.17-3.07 (m, 4H, H"-4, H-2, —OCH$_2$—CH$_2$—CH$_2$N—), 1.92 (s, 6H), 1.68-1.64 (m, 2H, —OCH$_2$—CH$_2$—CH$_2$N—); $^{13}$C NMR (200 MHz, MeOD) δ 174.63, 172.28, 157.45, 143.87, 143.85, 141.12, 127.28, 126.67, 124.72, 124.69, 119.42, 102.81 (C-1), 102.71 (C"-1), 96.85 (C'-1), 96.57 (C'''-1), 77.01, 76.19, 73.90, 73.67, 72.41, 71.51, 71.12, 70.82, 66.42 (—OCH$_2$—CH$_2$—CH$_2$N—), 66.09 (CH—CH$_2$O$_{-Fmoc}$), 61.41, 59.59, 53.97, 53.66, 47.02 (CH—CH$_2$O$_{-Fmoc}$), 37.10 (—OCH$_2$—CH$_2$—CH$_2$N—), 29.28 (—OCH$_2$—CH$_2$—CH$_2$N—), 21.36 (2×CH3). HRMS (ESI) m/z: [M–2H]$^{2-}$ calculated for C$_{46}$H$_{59}$N$_3$O$_{25}$ 526.6724; found 526.6712; [M–H]$^-$ calculated for C$_{46}$H$_{60}$N$_3$O$_{25}$ 1054.3521; found 1054.3501.

GlcAβ1-(4GlcNAcα1-4GlcAβ1)$_2$-ProNHFmoc (O5). 1.52 g, 87%. $^1$H NMR (800 MHz, MeOD) δ 7.70 (d, J=8.0 Hz, 2H), 7.55 (dd, J=7.2 Hz, 2H), 7.29 (t, J=7.2 Hz, 2H), 7.22 (t, J=7.2 Hz, 2H), 5.35 (d, J=3.2 Hz, 1H, H'''-1), 5.30 (d, J=3.2 Hz, 1H, H'-1), 4.33-4.32 (m, 2H, H"-1, H''''-1), 4.25 (d, J=7.2 Hz, 2H, CH—CH$_2$O$_{-Fmoc}$), 4.15 (d, J=8.0 Hz, 1H, H-1), 4.10 (t, J=7.2 Hz, 1H, CH—CH$_2$O$_{-Fmoc}$), 3.85-3.32 (m, 23H), 3.24-3.08 (m, 5H), 1.92 (s, 3H), 1.91 (s, 3H), 1.68-1.64 (m, 2H, —OCH$_2$—CH$_2$—CH$_2$N—); $^{13}$C NMR (200 MHz, MeOD) δ 175.17, 174.81, 174.37, 172.43, 172.27, 157.45, 143.88, 143.86, 141.12, 127.27, 126.67, 124.72, 124.69, 119.41, 102.80 (C-1), 102.73 (C"-1, C''''-1), 96.85 (C'-1), 96.68 (C'''-1), 78.45, 77.69, 77.17, 76.94, 76.46, 76.28, 75.87, 75.57, 73.94, 73.90, 73.74, 73.22, 71.97, 71.19, 70.82, 69.75, 69.68, 66.37 (—OCH$_2$—CH$_2$—CH$_2$N—), 66.08 (CH—CH$_2$O$_{-Fmoc}$), 59.82, 59.77, 53.86, 53.66, 47.03 (CH—CH$_2$O$_{-Fmoc}$), 37.09

(—OCH$_2$—CH$_2$—CH$_2$N—), 29.29 (—OCH$_2$—CH$_2$—CH$_2$N—), 21.39 (CH$_3$), 21.35 (CH$_3$). HRMS (ESI) m/z: [M−2H]$^{2-}$ calculated for C$_{52}$H$_{67}$N$_3$O$_{31}$ 614.6885; found 614.6872; [M−H]$^-$ calculated for C$_{52}$H$_{68}$N$_3$O$_{31}$ 1230.3842; found 1230.3837.

GlcNAcα1-(4GlcAβ1-4GlcNAcα1)$_2$-4GlcAβProNHFmoc (O6). 1.60 g, 99%. $^1$H NMR (800 MHz, MeOD) δ 7.69 (d, J=8.0 Hz, 2H), 7.55 (dd, J=8.0 Hz, 2H), 7.29 (t, J=7.2 Hz, 2H), 7.21 (t, J=7.2 Hz, 2H), 5.34 (d, J=3.2 Hz, 2H, H'''-1, H''''-1), 5.30 (d, J=4.0 Hz, 1H, H'-1), 4.33-4.32 (m, 2H, H''-1, H'''''-1), 4.25 (d, J=6.4 Hz, 2H, CH—CH$_2$O$_{\_Fmoc}$), 4.15 (d, J=7.2 Hz, 1H, H-1), 4.10 (t, J=7.2 Hz, 1H, CH—CH$_2$O$_{\_Fmoc}$), 3.83-3.41 (m, 28H), 3.24-3.08 (m, 6H), 1.92 (s, 3H), 1.91 (s, 3H), 1.90 (s, 3H), 1.68-1.64 (m, 2H, —OCH$_2$—CH$_2$—CH$_2$N—); $^{13}$C NMR (200 MHz, MeOD) δ 174.79, 174.55, 174.40, 172.36, 172.32, 172.30, 157.46, 143.88, 143.86, 141.12, 141.11, 127.27, 126.72, 126.67, 124.73, 124.69, 119.42, 102.80 (C-1)_, 102.63 (C-1''), 102.54 (C-1'''), 96.85 (C'-1), 96.59 (C'''-1), 96.51 (C'''''-1), 78.22, 77.15, 76.90, 76.40, 76.30, 76.13, 75.63, 73.92, 73.74, 72.39, 71.53, 71.19, 70.94, 70.88, 69.76, 69.66, 66.41 (—OCH$_2$—CH$_2$—CH$_2$N—), 66.09 (CH—CH$_2$O$_{\_Fmoc}$), 61.43, 59.83, 59.73, 53.98, 53.71, 53.68, 47.03 (CH—CH$_2$O$_{\_Fmoc}$), 37.08 (—OCH$_2$—CH$_2$—CH$_2$N—), 29.30 (—OCH$_2$—CH$_2$—CH$_2$N—), 21.39, 21.38. HRMS (ESI) m/z: [M−2H]$^{2-}$ calculated for C$_{60}$H$_{80}$N$_4$O$_{36}$ 716.2281; found 716.2260.

GlcAβ1-(4GlcNAcα1-4GlcAβ1)3ProNHFmoc (O7). 566 mg, 98%. $^1$H NMR (800 MHz, D$_2$O/MeOD) δ 7.80 (d, J=8.0 Hz, 2H), 7.64 (dd, J=7.2 Hz, 2H), 7.40 (t, J=7.2 Hz, 2H), 7.32 (t, J=7.2 Hz, 2H), 5.44-5.43 (m, 2H, H'''-1, H'''''-1), 5.41 (d, J=3.2 Hz, 1H, H'-1), 4.44-4.43 (m, 3H, H''-1, H'''-1, H'''''-1), 4.35 (d, J=7.2 Hz, 2H, CH—CH$_2$O$_{\_Fmoc}$), 4.29 (d, J=8.0 Hz, 1H, H-1), 4.19 (t, J=7.2 Hz, 1H, CH—CH$_2$O$_{\_Fmoc}$), 3.94-3.44 (m, 32H), 3.35-3.16 (m, 6H), 2.03 (s, 3H), 2.02 (s, 3H), 2.01 (s, 3H), 1.77-1.74 (m, 2H, —OCH$_2$—CH$_2$—CH$_2$N—); $^{13}$C NMR (200 MHz, D$_2$O/MeOD) δ 175.23, 174.79, 174.49, 174.48, 173.04, 172.96, 172.92, 157.73, 143.85, 143.82, 141.13, 134.34, 127.54, 126.93, 124.84, 124.81, 120.07, 119.60, 102.69 (C-1), 102.64 (C''-1, C''''-1, C''''''-1), 96.69 (C'-1), 96.65 (C'''-1), 96.61 (C'''''-1), 78.61, 78.52, 78.23, 77.11, 76.96, 76.57, 76.54, 76.48, 76.47, 75.89, 75.66, 75.51, 75.47, 74.33, 73.88, 73.73, 73.21, 72.01, 71.06, 70.88, 70.85, 69.60, 69.51, 69.46, 66.83 (—OCH$_2$—CH$_2$—CH$_2$N—), 66.27 (CH—CH$_2$O$_{\_Fmoc}$), 61.43, 59.78, 59.58, 53.73, 53.58, 53.55, 47.03 (CH—CH$_2$O$_{\_Fmoc}$), 37.20 (—OCH$_2$—CH$_2$—CH$_2$N—), 29.26 (—OCH$_2$—CH$_2$—CH$_2$N—), 21.67, 21.63. HRMS (ESI) m/z: [M−2H]$^{2-}$ calculated for C$_{64}$H$_{88}$N$_4$O$_{42}$ 804.2442; found 804.2420.

GlcNAcα1-(4GlcAβ1-4GlcNAcα1)$_3$-4GlcAβProNHFmoc (O8). 504 mg, 99%. $^1$H NMR (800 MHz, D$_2$O/MeOD) δ 7.79 (d, J=7.2 Hz, 2H), 7.61 (dd, J=8.0 Hz, 2H), 7.40 (t, J=7.2 Hz, 2H), 7.32 (t, J=7.2 Hz, 2H), 5.41 (d, J=4.0 Hz, 1H), 5.39 (d, J=3.2 Hz, 2H), 5.37 (d, J=4.0 Hz, 1H), 4.43 (d, J=7.2 Hz, 1H), 4.42 (d, J=7.2 Hz, 1H), 4.35 (d, J=7.2 Hz, 2H, CH—CH$_2$O$_{\_Fmoc}$), 4.30 (d, J=7.2 Hz, 1H, H-1), 4.17 (t, J=7.2 Hz, 1H, CH—CH$_2$O$_{\_Fmoc}$), 3.87-3.52 (m, 37H), 3.24-3.08 (m, 7H), 2.01 (s, 3H), 2.00 (s, 9H), 1.73-1.71 (m, 2H, —OCH$_2$—CH$_2$—CH$_2$N—); $^{13}$C NMR (200 MHz, D$_2$O/MeOD) δ 174.71, 174.60, 174.50, 174.48, 173.51, 173.45, 173.41, 157.91, 143.81, 143.79, 141.10, 127.70, 127.09, 124.87, 124.85, 119.74, 102.55, 102.52, 102.51, 96.68 (C'-1), 96.63 (C'''-1, C''''-1, C''''''-1), 78.79, 78.76, 77.07, 76.86, 76.63, 76.39, 76.30, 75.94, 75.74, 75.48, 73.75, 73.63, 72.23, 71.06, 70.78, 70.76, 70.43, 69.38, 69.34, 67.17 (—OCH$_2$—CH$_2$—CH$_2$N—), 66.29 (CH—CH$_2$O$_{\_Fmoc}$), 61.49, 60.83, 59.76, 59.52, 53.90, 53.46, 53.43, 47.04 (CH—CH$_2$O$_{\_Fmoc}$), 37.23 (—OCH$_2$—CH$_2$—CH$_2$N—), 29.15 (—OCH$_2$—CH$_2$—CH$_2$N—), 21.81, 21.79. HRMS (ESI) m/z: [M−2H]$^{2-}$ calculated for C$_{74}$H$_{103}$N$_5$O$_{47}$ 905.7838; found 905.7812.

GlcAβ1-(4GlcNAcα1-4GlcAβ1)$_4$-ProNHFmoc (O9). 445 mg, 96%. $^1$H NMR (800 MHz, D$_2$O/MeOD) δ 7.78 (d, J=7.2 Hz, 2H), 7.59 (dd, J=8.0 Hz, 2H), 7.39 (t, J=7.2 Hz, 2H), 7.31 (t, J=7.2 Hz, 2H), 5.34 (d, J=4.0 Hz, 3H), 5.33 (d, J=3.2 Hz, 1H), 4.41 (d, J=8.0 Hz, 1H), 4.40 (d, J=8.0 Hz, 3H), 4.35 (d, J=6.4 Hz, 2H, CH—CH$_2$O$_{\_Fmoc}$), 4.29 (d, J=8.0 Hz, 1H, H-1), 4.16 (t, J=6.4 Hz, 1H, CH-CH$_2$O$_{\_Fmoc}$), 3.88-3.42 (m, 41H), 3.30-3.07 (m, 7H), 1.98 (s, 3H), 1.97 (s, 9H), 1.69-1.66 (m, 2H, —OCH$_2$—CH$_2$—CH$_2$N—); $^{13}$C NMR (200 MHz, D20/MeOD) δ 174.99, 174.59, 174.35, 173.23, 173.18, 173.14, 157.82, 143.81, 143.78, 141.12, 127.63, 127.01, 124.86, 124.83, 119.66, 102.61, 102.57, 96.67 (C'-1), 96.62 (C'''-1, C''''-1, C''''''-1), 78.78, 78.70, 78.64, 76.96, 76.90, 76.52, 76.42, 75.85, 75.62, 75.59, 75.55, 73.79, 73.67, 73.16, 71.98, 70.89, 70.79, 69.49, 69.35, 69.32, 66.99 (—OCH$_2$—CH$_2$—CH$_2$N—), 66.28 (CH-CH$_2$O$_{\_Fmoc}$), 62.77, 61.46, 59.72, 59.49, 53.59, 53.48, 53.45, 47.03 (CH—CH$_2$O$_{\_Fmoc}$), 37.20 (—OCH$_2$—CH$_2$—CH$_2$N—), 29.19 (—OCH$_2$—CH$_2$—CH$_2$N—), 21.72, 21.69. HRMS (ESI) m/z: [M−2]$^{2-}$ calculated for C$_{80}$H$_{109}$N$_5$O$_{53}$ 993.7999; found 993.7973.

GlcNAcα1-(4GlcAβ1-4GlcNAcα1)$_4$-4GlcAβProNHFmoc (O10). 430 mg, 98%. $^1$H NMR (800 MHz, D$_2$O) δ 7.88 (d, J=8.0 Hz, 2H), 7.66 (dd, J=8.0 Hz, 2H), 7.46 (t, J=8.0 Hz, 2H), 7.39 (t, J=8.0 Hz, 2H), 5.38 (d, J=4.0 Hz, 1H), 5.36 (d, J=4.0 Hz, 3H), 5.35 (d, J=3.2 Hz, 1H), 4.61-4.55 (m, 6H), 4.33 (d, J=8.0 Hz, 1H, H-1), 4.26 (t, J=6.4 Hz, 1H, CH—CH$_2$O$_{\_Fmoc}$), 3.90-3.62 (m, 46H), 3.47 (t, J=11.4 Hz, 1H), 3.44-3.40 (m, 1H), 3.36-3.32 (m, 3H), 3.24 (t, J=8.8 Hz, 1H), 3.06-3.29 (m, 2H), 2.04-2.00 (m, 15H), 1.61-1.55 (m, 2H, —OCH$_2$—CH$_2$—CH$_2$N—); $^{13}$C NMR (200 MHz, D$_2$O) δ 174.39, 174.32, 174.29, 174.05, 174.00, 173.92, 143.83, 141.00, 127.98, 127.41, 124.95, 120.08, 118.85, 102.27, 102.22, 97.07, 96.86, 78.27, 76.34, 76.17, 76.07, 76.04, 76.02, 75.90, 75.72, 75.67, 73.38, 73.34, 73.26, 71.97, 70.68, 70.59, 69.53, 68.92, 67.51 (—OCH$_2$—CH$_2$—CH$_2$N—), 65.70 (CH—CH$_2$O$_{\_Fmoc}$), 61.41, 59.96, 59.27, 59.25, 53.59, 53.25, 53.20, 47.31 (CH—CH$_2$O$_{\_Fmoc}$), 36.77 (—OCH$_2$—CH$_2$—CH$_2$N—), 28.52 (—OCH$_2$—CH$_2$—CH$_2$N—), 21.86. HRMS (ESI) m/z: [M−3H]$^{3-}$ calculated for C$_{88}$H$_{121}$N$_6$O$_{58}$ 729.8901; found 729.8904; [M−2H]$^{2-}$ calculated for C$_{88}$H$_{122}$N$_6$O$_{58}$ 1095.3391; found 1095.3393.

REFERENCES (1) Xu, D.; Esko, J. D. Demystifying Heparan Sulfate-Protein Interactions. *Annu. Rev. Biochem.* 2014, 83, 129-257.

(2) Lindahl, U.; Couchman, J.; Kimata, K.; Esko, J. D. Proteoglycans And Sulfated Glycosaminoglycans. In *Essentials of Glycobiology*, 3$^{rd}$ Ed.; Varki, A.; Cummings, R. D.; Esko, J. D.; Stanley, P.; Hart, G. W.; Aebi, M.; Darvill, A. G.; Kinoshita, T.; Packer, N. H.; Prestegard, J. H.; Schnaar, R. L.; Seeberger, P. H. Eds. Cold Spring Harbor (N.Y.), 2015; pp 207-221.

(3) Yu, H.; Chen, X. Carbohydrate Post-Glycosylational Modifications. *Org. Biomol. Chem.* 2007, 5, 865-872.

(4) Chavaroche, A. A.; van den Broek, L. A.; Eggink, G. Production Methods for Heparosan, A Precursor of Heparin And Heparan Sulfate. *Carbohydr. Polym.* 2013, 93, 38-47.

(5) Li, P.; Sheng, J.; Liu, Y.; Li, J.; Liu, J.; Wang, F. Heparosan-Derived Heparan Sulfate/Heparin-Like Compounds: One Kind of Potential Therapeutic Agents. *Med. Res. Rev.* 2013, 33, 665-692.

(6) Lanzi, C.; Cassinelli, G. Heparan Sulfate Mimetics in Cancer Therapy: The Challenge to Define Structural Determinants and the Relevance of Targets for Optimal Activity. *Molecules* 2018, 23, 2915.

(7) Maciej-Hulme, M. L.; Skidmore, M. A.; Price, H. P. The Role of Heparan Sulfate in Host Macrophage Infection by Leishmania species. *Biochem Soc Trans* 2018, 46, 789-796.

(8) Sinay, P.; Jacquinet, J.-C.; Petitou, M.; Duchaussoy, P.; Lederman, I.; Choay, J.; Torri, G. Total Synthesis of A Heparin Pentasaccharide Fragment Having High Affinity for Antithrombin III. *Carbohydr. Res.* 1984, 132, C5-C9.

(9) Zong, C.; Venot, A.; Li, X.; Lu, W.; Xiao, W.; Wilkes, J. L.; Salanga, C. L.; Handel, T. M.; Wang, L.; Wolfert, M. A.; Boons, G. J. Heparan Sulfate Microarray Reveals That Heparan Sulfate-Protein Binding Exhibits Different Ligand Requirements. *J. Am. Chem. Soc.* 2017, 139, 9534-9543.

(10) Hung, S. C.; Lu, X. A.; Lee, J. C.; Chang, M. D.; Fang, S. L.; Fan, T. C.; Zulueta, M. M.; Zhong, Y. Q. Synthesis of Heparin Oligosaccharides And Their Interaction with Eosinophil-Derived Neurotoxin. *Org. Biomol. Chem.* 2012, 10, 760-772.

(11) Huang, T. Y.; Irene, D.; Zulueta, M. M.; Tai, T. J.; Lain, S. H.; Cheng, C. P.; Tsai, P. X.; Lin, S. Y.; Chen, Z. G.; Ku, C. C.; Hsiao, C. D.; Chyan, C. L.; Hung, S. C. Structure of The Complex Between A Heparan Sulfate Octasaccharide And Mycobacterial Heparin-Binding Hemagglutinin. *Angew. Chem., Int. Ed.* 2017, 56, 4192-4196.

(12) Hu, Y.-P.; Lin, S.-Y.; Huang, C.-Y.; Zulueta, M. M. L.; Liu, J.-Y.; Chang, W.; Hung, S.-C. Synthesis of 3-O-Sulfonated Heparan Sulfate Octasaccharides That Inhibit The Herpes Simplex Virus Type 1 HostCell Interaction. *Nat. Chem.* 2011, 3, 557-563.

(13) Liu, J.; Linhardt, R. J. Chemoenzymatic Synthesis of Heparan Sulfate And Heparin. *Nat. Prod. Rep.* 2014, 31, 1676-1685.

(14) Chavaroche, A. A.; van den Broek, L. A.; Springer, J.; Boeriu, C.; Eggink, G. Analysis of The Polymerization Initiation And Activity of *Pasteurella multocida* Heparosan Synthase PmHS2, An Enzyme with Glycosyltransferase And UDP-Sugar Hydrolase activity. *J. Biol. Chem.* 2011, 286, 1777-1785.

(15) Chavaroche, A. A.; Springer, J.; Kooy, F.; Boeriu, C.; Eggink, G. In vitro Synthesis of Heparosan Using Recombinant *Pasteurella multocida* Heparosan Synthase PmHS2. *Appl. Microbiol. Biotechnol.* 2010, 85, 1881-1891.

(16) Xu, Y.; Masuko, S.; Takieddin, M.; Xu, H.; Liu, R.; Jing, J.; Mousa, S. A.; Linhardt, R. J.; Liu, J. Chemoenzymatic Synthesis of Homogeneous Ultralow Molecular Weight Heparins. *Science* 2011, 334, 498-501.

(17) Liu, R.; Xu, Y.; Chen, M.; Weiwer, M.; Zhou, X.; Bridges, A. S.; DeAngelis, P. L.; Zhang, Q.; Linhardt, R. J.; Liu, J. Chemoenzymatic Design of Heparan Sulfate Oligosaccharides. *J. Biol. Chem.* 2010, 285, 34240-34249.

(18) Chen, Y.; Li, Y.; Yu, H.; Sugiarto, G.; Thon, V.; Hwang, J.; Ding, L.; Hie, L.; Chen, X. Tailored Design and Synthesis of Heparan Sulfate Oligosaccharide Analogues Using Sequential One-Pot Multienzyme Systems. *Angew. Chem., Int. Ed.* 2013, 52, 11852-11856.

(19) Vann, W. F.; Schmidt, M. A.; Jann, B.; Jann, K. The Structure of The Capsular Polysaccharide (K5 Antigen) of Urinary-Tract-Infective *Escherichia coli* 010:K5:H4. A Polymer Similar to Desulfo-Heparin. *Eur. J. Biochem.* 1981, 116, 359-364.

(20) DeAngelis, P. L.; White, C. L. Identification And Molecular Cloning of A Heparosan Synthase from *Pasteurella multocida* Type D. *J. Biol. Chem.* 2002, 277, 7209-7213.

(21) Wu, J. R.; Chen, P. Y.; Shien, J. H.; Shyu, C. L.; Shieh, H. K.; Chang, F.; Chang, P. C. Analysis of The Biosynthesis Genes And Chemical Components of The Capsule of *Avibacterium paragallinarum*. *Vet. Microbiol.* 2010, 145, 90-99.

(22) DeAngelis, P. L.; White, C. L. Identification of A Distinct, Cryptic Heparosan Synthase from *Pasteurella multocida* Types A, D, and F. *J. Bacteriol.* 2004, 186, 8529-8532.

(23) Kane, T. A.; White, C. L.; DeAngelis, P. L., Functional Characterization of PmHS1, A *Pasteurella multocida* Heparosan Synthase. *J. Biol. Chem.* 2006, 281, 33192-33197.

(24) Sismey-Ragatz, A. E.; Green, D. E.; Otto, N. J.; Rejzek, M.; Field, R. A.; DeAngelis, P. L. Chemoenzymatic Synthesis with Distinct *Pasteurella heparosan* Synthases: Monodisperse Polymers And Unnatural Structures. *J. Biol. Chem.* 2007, 282, 28321-28327.

(25) Wu, B.; Wei, N.; Thon, V.; Wei, M.; Yu, Z.; Xu, Y.; Chen, X.; Liu, J.; Wang, P. G.; Li, T. Facile Chemoenzymatic Synthesis of Biotinylated Heparosan Hexasaccharide. *Org. Biomol. Chem.* 2015, 13, 5098-5101.

(26) DiGabriele, A. D.; Lax, I.; Chen, D. I.; Svahn, C. M.; Jaye, M.; Schlessinger, J.; Hendrickson, W. A. Structure of A Heparin-Linked Biologically Active Dimer of Fibroblast Growth Factor. *Nature* 1998, 393, 812-817.

(27) Xu, D.; Young, J. H.; Krahn, J. M.; Song, D.; Corbett, K. D.; Chazin, W. J.; Pedersen, L. C.; Esko, J. D. Stable RAGE-Heparan Sulfate Complexes Are Essential for Signal Transduction. *ACS Chem. Biol.* 2013, 8, 1611-1620.

(28) Ricard-Blum, S.; Beraud, M.; Raynal, N.; Farndale, R. W.; Ruggiero, F. Structural Requirements for Heparin/Heparan Sulfate Binding to Type V Collagen. *J. Biol. Chem.* 2006, 281, 25195-25204.

(29) Vanpouille, C.; Denys, A.; Carpentier, M.; Pakula, R.; Mazurier, J.; Allain, F. Octasaccharide Is The Minimal Length Unit Required for Efficient Binding of Cyclophilin B to Heparin And Cell Surface Heparan Sulphate. *Biochem. J.* 2004, 382 (Pt 2), 733-740.

(30) Smith, R. A. A.; Murali, S.; Rai, B.; Lu, X.; Lim, Z. X. H.; Lee, J. J. L.; Nurcombe, V.; Cool, S. M. Minimum Structural Requirements for BMP-2-Binding of Heparin Oligosaccharides. *Biomaterials* 2018, 184, 41-55.

(31) Slabinski, L.; Jaroszewski, L.; Rodrigues, A. P.; Rychlewski, L.; Wilson, I. A.; Lesley, S. A.; Godzik, A. The Challenge of Protein Structure Determination-Lessons from Structural Genomics. *Protein Sci.* 2007, 16, 2472-2482.

(32) Li, Y.; Yu, H.; Thon, V.; Chen, Y.; Muthana, M. M.; Qu, J.; Hie, L.; Chen, X. Donor Substrate Promiscuity of The N-Acetylglucosaminyltransferase Activities of *Pasteurella multocida* Heparosan Synthase 2 (PmHS2) and *Escherichia coli* K5 KfiA. *Appl. Microbiol. Biotechnol.* 2014, 98, 1127-1134.

(33) Lau, K.; Thon, V.; Yu, H.; Ding, L.; Chen, Y.; Muthana, M. M.; Wong, D.; Huang, R.; Chen, X. Highly Efficient Chemoenzymatic Synthesis of beta1-4-Linked Galactosides with Promiscuous Bacterial beta1-4-Galactosyltransferases. *Chem. Commun.* 2010, 46, 6066-6068.
(34) Li, Y.; Yu, H.; Chen, Y.; Lau, K.; Cai, L.; Cao, H.; Tiwari, V. K.; Qu, J.; Thon, V.; Wang, P. G.; Chen, X. Substrate Promiscuity of N-Acetylhexosamine 1-Kinases. *Molecules* 2011, 16, 6396-6407.
(35) Chen, Y.; Thon, V.; Li, Y.; Yu, H.; Ding, L.; Lau, K.; Qu, J.; Hie, L.; Chen, X. One-Pot Three-Enzyme Synthesis of UDP-GlcNAc Derivatives. *Chem. Commun.* 2011, 47, 10815-10817.
(36) Muthana, M. M.; Qu, J.; Xue, M.; Klyuchnik, T.; Siu, A.; Li, Y.; Zhang, L.; Yu, H.; Li, L.; Wang, P. G.; Chen, X. Improved One-Pot Multienzyme (OPME) Systems for Synthesizing UDP-Uronic Acids And Glucuronides. *Chem. Commun.* 2015, 51, 4595-4598.
(37) Muthana, M. M.; Qu, J.; Li, Y.; Zhang, L.; Yu, H.; Ding, L.; Malekan, H.; Chen, X. Efficient One-Pot Multienzyme Synthesis of UDP-Sugars Using A Promiscuous UDP-Sugar Pyrophosphorylase from *Bifidobacterium longum* (BLUSP). *Chem. Commun.* 2012, 48, 2728-2730.
(38) Zhang, C.; Griffith, B. R.; Fu, Q.; Albermann, C.; Fu, X.; Lee, I. K.; Li, L.; Thorson, J. S. Exploiting The Reversibility of Natural Product Glycosyltransferase-Catalyzed Reactions. *Science* 2006, 313, 1291-1294.
(39) Gantt, R. W.; Peltier-Pain, P.; Cournoyer, W. J.; Thorson, J. S. Using Simple Donors to Drive The Equilibria of Glycosyltransferase-Catalyzed Reactions. *Nat. Chem. Biol.* 2011, 7, 685-691.
(40) Chandrasekaran, E. V.; Xue, J.; Xia, J.; Locke, R. D.; Matta, K. L.; Neelamegham, S. Reversible Sialylation: Synthesis of Cytidine 5'-Monophospho-N-Acetylneuraminic Acid from Cytidine 5'-Monophosphate with alpha2,3-Sialyl O-Glycan-, Glycolipid-, And Macromolecule-Based Donors Yields Diverse Sialylated Products. *Biochemistry* 2008, 47, 320-330.
(41) Mehr, K.; Withers, S. G. Mechanisms of The Sialidase And Trans-Sialidase Activities of Bacterial Sialyltransferases from Glycosyltransferase Family 80. *Glycobiology* 2016, 26, 353-359.
(42) McArthur, J. B.; Yu, H.; Tasnima, N.; Lee, C. M.; Fisher, A. J.; Chen, X. Alpha2-6-Neosialidase: A Sialyltransferase Mutant as A Sialyl Linkage-Specific Sialidase. *ACS Chem. Biol.* 2018, 13, 1228-1234.
(43) Chavaroche, A. A.; van den Broek, L. A.; Boeriu, C.; Eggink, G. Synthesis of Heparosan Oligosaccharides by *Pasteurella multocida* PmHS2 Single-Action Tansferases. *Appl. Microbiol. Biotechnol.* 2012, 95, I199-1210.
(44) Li, Y.; Xue, M.; Sheng, X.; Yu, H.; Zeng, J.; Thon, V.; Chen, Y.; Muthana, M. M.; Wang, P. G.; Chen, X. Donor Substrate promiscuity of bacterial beta1-3-N-acetylglucosaminyltransferases and acceptor substrate flexibility of beta1-4-galactosyltransferases. *Bioorg. Med. Chem.* 2016, 24, 1696-1705.
(45) Yu, H.; Chokhawala, H.; Karpel, R.; Yu, H.; Wu, B.; Zhang, J.; Zhang, Y.; Jia, Q.; Chen, X. A Multifunctional *Pasteurella multocida* Sialyltransferase: A Powerful Tool for The Synthesis of Sialoside Libraries. *J. Am. Chem. Soc.* 2005, 127, 17618-17619.
(46) Yang, J.; Yan, R.; Roy, A.; Xu, D.; Poisson, J.; Zhang, Y. The I-TASSER Suite: Protein Structure And Function Prediction. *Nat. Meth.* 2015, 12, 7-8.
(47) Roy, A.; Kucukural, A.; Zhang, Y. I-TASSER: A Unified Platform for Automated Protein Structure And Function Prediction. *Nat. Protoc.* 2010, 5, 725-738.
(48) Osawa, T.; Sugiura, N.; Shimada, H.; Hirooka, R.; Tsuji, A.; Shirakawa, T.; Fukuyama, K.; Kimura, M.; Kimata, K.; Kakuta, Y. Crystal Structure of Chondroitin Polymerase from *Escherichia coli* K4. *Biochem. Biophys. Res. Commun.* 2009, 378, 10-14.
(49) Persson, K.; Ly, H. D.; Dieckelmann, M.; Wakarchuk, W. W.; Withers, S. G.; Strynadka, N. C. Crystal Structure of The Retaining Galactosyltransferase LgtC from *Neisseria meningitidis* in Complex with Donor And Acceptor Sugar Analogs. *Nat. Struct. Biol.* 2001, 8, 166-175.
(50) Lairson, L. L.; Chiu, C. P.; Ly, H. D.; He, S.; Wakarchuk, W. W.; Strynadka, N. C.; Withers, S. G. Intermediate Trapping on A Mutant Retaining Alpha-Galactosyltransferase Identifies An Unexpected Aspartate Residue. *J. Biol. Chem.* 2004, 279, 28339-28344.
(51) Gomez, H.; Polyak, I.; Thiel, W.; Lluch, J. M.; Masgrau, L. Retaining Glycosyltransferase Mechanism Studied by QM/MM Methods: Lipopolysaccharyl-Alpha-1,4-Galactosyltransferase C Transfers Alpha-galactose via An Oxocarbenium Ion-Like Transition State. *J. Am. Chem. Soc.* 2012, 134, 4743-4752.
(52) Jamaluddin, H.; Tumbale, P.; Withers, S. G.; Acharya, K. R.; Brew, K. Conformational Changes Induced by Binding UDP-2F-Galactose to Alpha-1,3 Galactosyltransferase-Implications for Catalysis. *J. Mol. Biol.* 2007, 369, 1270-1281.

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

What is claimed is:

1. A *Pasteurella multocida* heparosan synthase 2 (PmHS2) variant consisting essentially of a polypeptide having at least 90% identity to the amino acid sequence set forth in SEQ ID NO:1, which comprises a mutation at one or more positions corresponding to Y165, R184, L185, F187, I188, T189, D211, N237, K379, L462, T464, T466, V467, S485, G486, M487, and D489 in SEQ ID NO:1.

2. The PmHS2 variant of claim 1, which consists of the polypeptide having at least 95% identity to the amino acid sequence set forth in SEQ ID NO:1.

3. A *Pasteurella multocida* heparosan synthase 2 (PmHS2) variant consisting essentially of a polypeptide having at least 90% identity to the amino acid sequence set forth in SEQ ID NO:3, which comprises a mutation at one or more positions corresponding to Y176, R195, L196, F198, I199, T200, D222, N248, K390, L473, T475, T477, V478, S496, G497, M498, and D500 in SEQ ID NO:3.

4. The PmHS2 variant of claim 3, which consists of the polypeptide having at least 95% identity to the amino acid sequence set forth in SEQ ID NO:3.

5. The PmHS2 variant of claim 3, which comprises one or more mutations corresponding to Y176A, R195A, L196A, F198A, I199A, T200A, D222N, N248A, K390A, L473A, T475A, T477A, V478A, S496N, S496A, G497 deletion, M498A, and D500N in SEQ ID NO:3.

6. The PmHS2 variant of claim 5, which comprises the mutation D222N or D500N in SEQ ID NO:3.

7. The PmHS2 variant of claim 5, which comprises the mutations D410N, D412N, and D500N in SEQ ID NO:3.

8. The PmHS2 variant of claim 5, which comprises the mutation with G497 deletion in SEQ ID NO:3.

9. The PmHS2 variant of claim 5, which comprises the mutations Y176A, R195A, L196A, F198A, I199A, T200A, and/or N248A in SEQ ID NO:3.

10. The PmHS2 variant of claim 5, which comprises the mutations K390A, L473A, T475A, T477A, and/or V478A in SEQ ID NO:3.

11. The PmHS2 variant of claim 5, which comprises the mutations S496N, S496A, and/or M498A in SEQ ID NO:3.

12. A method of preparing an oligosaccharide, the method comprising:

forming a mixture comprising (i) PmHS2 variant of claim 1, (ii) an acceptor sugar, and (iii) a nucleotide sugar comprising a nucleotide moiety and a donor sugar moiety, and maintaining the mixture under conditions sufficient to transfer the donor sugar moiety to the acceptor sugar.

13. The method of claim 12, wherein the nucleotide sugar in the mixture is formed by converting a sugar starting material to the nucleotide sugar.

14. The method of claim 12, wherein the acceptor sugar is selected from the group consisting of a monosaccharide, a disaccharide, a trisaccharide, a tetrasaccharide, a pentasaccharide, a hexasaccharide, a heptasaccharide, an octasaccharide, and a nonasaccharide.

15. A method of preparing an oligosaccharide, the method comprising:

forming a mixture comprising (i) PmHS2 variant of claim 3, (ii) an acceptor sugar, and (iii) a nucleotide sugar comprising a nucleotide moiety and a donor sugar moiety, and maintaining the mixture under conditions sufficient to transfer the donor sugar moiety to the acceptor sugar.

16. The method of claim 15, wherein the nucleotide sugar in the mixture is formed by converting a sugar starting material to the nucleotide sugar.

17. The method of claim 15, wherein the acceptor sugar is selected from the group consisting of a monosaccharide, a disaccharide, a trisaccharide, a tetrasaccharide, a pentasaccharide, a hexasaccharide, a heptasaccharide, an octasaccharide, and a nonasaccharide.

\* \* \* \* \*